US005691177A

United States Patent [19]

Guber et al.

[11] Patent Number: 5,691,177
[45] Date of Patent: Nov. 25, 1997

[54] RECOMBINANT RETROVIRUSES EXPRESSING A PROTEIN THAT CONVERTS A PRO-DRUG INTO A CYTOTOXIC AGENT

[76] Inventors: Harry E. Guber, 13083 Maritime Pl., San Diego, Calif. 92130; Douglas J. Jolly, 3050 Via Alicante Dr., La Jolla, Calif. 92037; James G. Respess, 4966 Lamont St., San Diego, Calif. 92109; Paul K. Laikind, 12433 Caminito Mira Del Mar, San Diego, Calif. 92130

[21] Appl. No.: 460,996

[22] Filed: Jun. 5, 1995

Related U.S. Application Data

[62] Division of Ser. No. 136,739, Oct. 12, 1993, which is a continuation of Ser. No. 395,932, Aug. 18, 1989, abandoned, which is a continuation-in-part of Ser. No. 170,515, Mar. 21, 1988, abandoned.

[51] Int. Cl.$^6$ ................................ C12N 5/08; C12N 5/10
[52] U.S. Cl. ...................... 435/172.3; 435/69.1; 435/372
[58] Field of Search .............................. 435/69.1, 172.3, 435/372

[56] References Cited

U.S. PATENT DOCUMENTS

| | | | |
|---|---|---|---|
| 4,405,712 | 9/1983 | Vande Woude et al. | 435/5 |
| 4,650,764 | 3/1987 | Temin et al. | 435/240.1 |
| 4,663,281 | 5/1987 | Gillies et al. | 435/69.1 |
| 4,708,818 | 11/1987 | Montagnier et al. | 435/5 |
| 4,725,669 | 2/1988 | Essex et al. | 530/322 |
| 4,738,922 | 4/1988 | Haseltine et al. | 435/69.1 |
| 4,861,719 | 8/1989 | Miller | 435/236 |
| 4,868,116 | 9/1989 | Morgan et al. | 435/240.2 |
| 4,980,286 | 12/1990 | Morgan et al. | 435/172.3 |
| 4,980,289 | 12/1990 | Temin et al. | 435/235.1 |
| 5,026,635 | 6/1991 | Ferguson et al. | 435/5 |
| 5,192,553 | 3/1993 | Boyse et al. | 424/529 |
| 5,246,924 | 9/1993 | Fox et al. | 514/50 |
| 5,304,489 | 4/1994 | Rosen | 435/320.1 |
| 5,306,631 | 4/1994 | Harrison et al. | 435/172.3 |
| 5,399,346 | 3/1995 | Anderson et al. | 424/93.21 |

FOREIGN PATENT DOCUMENTS

| | | |
|---|---|---|
| 0 178 220 A2 | 4/1986 | European Pat. Off. . |
| 0 243 204 A2 | 10/1987 | European Pat. Off. . |
| 0 288 163 A2 | 10/1988 | European Pat. Off. . |
| 0 293 181 A1 | 11/1988 | European Pat. Off. . |
| 0 334 301 A1 | 9/1989 | European Pat. Off. . |
| 0 361 749 A1 | 4/1990 | European Pat. Off. . |
| 0 386 882 A1 | 9/1990 | European Pat. Off. . |
| 2 559 159 | 2/1984 | France . |
| 2 606 030 | 6/1988 | France . |
| 0 273 782 A1 | 7/1988 | France . |
| WO8505629 | 12/1985 | WIPO . |
| WO86/00922 | 2/1986 | WIPO . |
| WO86/00930 | 2/1986 | WIPO . |
| WO89/02468 | 3/1989 | WIPO . |
| WO89/05345 | 6/1989 | WIPO . |
| WO89/05349 | 6/1989 | WIPO . |
| WO89/07150 | 8/1989 | WIPO . |
| WO90/01870 | 3/1990 | WIPO . |
| WO90/02806 | 3/1990 | WIPO . |
| WO90/11092 | 10/1990 | WIPO . |
| WO93/02556 | 2/1993 | WIPO . |

OTHER PUBLICATIONS

Nelson et al. "Gene replacment therapy for inborn errors of purine metabolism", Cold Spring Harbor Symp. Quant. Biol., 51(2): 1065–1071, 1986.

Besnard et al., "Selection against expression of the *Escherichia coil* gene gpt in hprt+ mouse teratocarcinoma and hybrid cells", Mol. Cell. Biol., 7(11): 4139–4141, Nov. 1987.

Borrelli et al., "Targeting of inducible toxic phenotype in animal cells", Proc. Nat. Acad. Sci. USA, 85: 7572–7576, Oct. 1988.

Trucco, "Molecular mechanisms involved in the etiology and pathogenesis of autoimmune diseases", Clin. Investig., 70:756–765, 1992.

Crystal, R. G., "Transfer of Genes to Humans: Early Lessons and Obstacles to Success," *Science*, 270:404–410 (Oct. 20, 1995).

Barinaga, M., "Step Taken Toward Improved Vectors for Gene Transfer," *Science*, 266:1326 (Nov. 25, 1994).

Jolly, D., "Viral Vector Systems For Gene Therapy," *Cancer Gene Therapy*, 1(1):51–64 (1994).

Marshall, E., "Gene Therapy's Growing Pains," *Science*, 269:1050–1055 (Aug. 25, 1995).

Orkin et al., "Report and Recommendations of the Panel to Assess the NIH Investment in Research on Gene Therapy," (Dec. 7, 1995).

Bachmann, et al., "In Vivo versus In Vitro Assays for Assessment of T–and B–cell Function," *Immunological Techniques*, 6:320–326 (1994).

Jolly, et al., "Variable Stability of a Selectable Provirus After Retroviral Vector Gene Transfer Into Human Cells," *Molecular and Cellular Biology*, 6(4):1141–1147 (Apr. 1986).

Willis, et al., "Partial Phenotypic Correction of Human Lesch–Nyhan (Hypoxanthine–Guanine Phosphoribosyltransferase–deficient) Lymphoblasts with a Transmissible Retroviral Vector," *The Journal of Biological Chemistry*, 259(12):7842–7849 (Jun. 25, 1984).

(List continued on next page.)

*Primary Examiner*—George G. Elliott
*Assistant Examiner*—Johnny F. Railey, II
*Attorney, Agent, or Firm*—Norman J. Kruse; Donald J. Pochopien; Robert P. Blackburn

[57] ABSTRACT

Recombinant retroviruses carrying a vector construct capable of preventing, inhibiting, stabilizing or reversing infectious, cancerous or auto-immune diseases are disclosed. More specifically, the recombinant retroviruses of the present invention are useful for (a) stimulating a specific immune response to an antigen or a pathogenic antigen; (b) inhibiting a function of a pathogenic agent, such as a virus; and (c) inhibiting the interaction of an agent with a host cell receptor. In addition, eucaryotic cells infected with, and pharmaceutical compositions containing such a recombinant retrovirus are disclosed. Various methods for producing recombinant retroviruses having unique characteristics, and methods for producing transgenic packaging animals or insects are also disclosed.

24 Claims, 27 Drawing Sheets

OTHER PUBLICATIONS

Klein, G., "Tumor Antigens," *Ann. Rev. Microbiol.* 20:223–252 (1966).

Hellström and Hellström, "Cellular Immunity Against Tumor Antigens," *Adv. Cancer Res.* 12:167–223 (1969).

Bishop, J.M., "Cancer Genes Come Of Age," *Cell* 32:1018–1020 (1983).

Hellström and Hellström, "Oncogene–associated Tumor Antigens as Targets for Immunotherapy," *FASEB J.* 3:1715–1722, (1989).

Miller, et al., "Treatment of B–Cell Lymphoma With Monoclonal Anti–Idiotype Antibody," *New England J. Med.* 306:517–522, (1982).

Bartram et al., "Translocation of c–abl Oncogene Correlates with the Presence of a Philadelphia Chromosome in chronic Myelocytic Leukaemia," *Nature* 306:277–280 (1983).

Yasukawa and Zarling, "Human Cytotoxic T Cell Clones Directed Against Herpes Simplex Virus–Infected Cells. III. Analysis of Viral Glycoproteins Recognized by CTL Clones by Using Recombinant Herpes Simplex Viruses," *J. Immunol.* 134(4):2679–2682, 1985.

Zarling, et al., "Human Cytotoxic T Cell Clones Directed Against Herpes Simplex Virus–Infected Cells. IV. Recognition and Activation by Cloned Glycoproteins gB and gD," *J. Immunol.* 136(12):4669–4673 (1986).

Zarling, et al., "Herpes Simplex Virus (HSV)–Specific Human T–Cell Clones Recognize HSV Glycoprotein D Expressed by a Recombinant Vaccinia Virus," *J. Virol.* 59(2):506–509 (1986).

Torseth, et al., "Native and Recombinant Herpes Simplex Virus Type 1 Envelope Protein Induce Human Immune T–Lymphocyte Responses," *J. Virol.* 61(5):1532–1539 (1987).

Kuriyama et al., "Gene therapy for the treatment of hepatoma by retroviral–mediated gene–transfer of the herpes–simplex virus thymidine kinase gene," *Int. Hepatol. Commun.* 1(5):253–259 (1993).

Kuriyama et al. (b), "A potential approach for gene therapy targeting hepatoma using a liver–specific promoter on a retroviral vector," *Cell Struct. Func.*, 16:503–510 (1991).

Pizer et al., "A mammalian cell line designed to test the mutagenic activity of anti–herpes nucleosides," *Int. J. Cancer,* 40:114–121 (1987).

Adam et al., "Identification of a Signal in a Murine Retrovirus That Is Sufficient for Packaging of Nonretroviral RNA into Virions," *J. Virology,* 62(10):3802–3806 (Oct., 1988).

Anderson F.W., "Human Gene Therapy," *Science,* 256:808–813 (May 8, 1992).

Cone et al., "Regulated Expression of a Complete Human β–Globin Gene Encoded by a Transmissible Retrovirus Vector," *Mol. & Cell. Biol,* 7(2):887–897 (Feb., 1987).

Cournoyer et al., "Gene Therapy of the Immune System," *Ann. Rev. Immunol.,* 11:297–329 (1993).

Danos et al., "Safe and Efficient Generation of Recombinant Retroviruses With Amphotropic and Ecotropic Host Ranges," *Proc. Nat'l Acad. Sci., USA,* 85:6460–6464 (Sep., 1988).

Dayton et al., "The Trans–Activator Gene of the Human T Cell Lymphotropic Virus Type III Is Required for Replication," *Cell,* 44:941–947 (Mar. 28, 1986).

Dzierzak et al., "Lineage–Specific Expression of A Human β–Globin Gene In Murine Bone Marrow Transplant Recipients Reconstituted With Retrovirus–transduced Stem Cells," *Nature,* 331:35–41 (Jan. 7, 1988).

Felber et al., "A Quantitative Bioassay For HIV–1 Based On Trans–Activation," *Science,* 239:184–187 (Jan. 8, 1988).

Felgner et al., "Lipofection: A Highly Efficient, Lipid–Mediated DNA–Transfection Procedure," *Proc. Nat'l Acad. Sci., USA,* 84:7413–7417 (Nov., 1987).

Frankel et al., "Dimerization of the Tat Protein from Human Immunodeficiency Virus: A Cysteine–Rich Peptide Mimics the Normal Metal–Linked Dimer Interface," *Proc. Nat'l Acad. Sci., USA,* 85:6297–6300 (Sep., 1988).

Frankel et al., "Tat Protein From Human Immunodeficiency Virus Forms A Metal–Linked Dimer," *Science,* 240:70–73 (Apr., 1988).

Friedman et al., "Expression Of A Truncated Viral Trans–Activator Selectively Impedes Lytic Infection By Its Cognate Virus," *Nature,* 335:452–454 (Sep. 29, 1988).

Furman et al., "Inhibition of Herpes Simplex Virus–Induced DNA Polymerase Activity and Viral DNA Replication by 9–(2–Hydroxyethoxymethyl)guanine and Its Triphosphate," *J. Virology,* 32(1):72–77 (Oct., 1979).

Ganz et al., "Defensins Natural Peptide Antibiotics of Human Neutrophils," *J. Clin. Invest.,* 76:1427–1435 (Oct., 1985).

Goelz, S.E., "Hypomethylation of DNA from Benign and Malignant Human Colon Neoplasms," *Science,* 228:187–190 (Apr. 12, 1985).

Graham et al., "A New Technique for the Assay of Infectivity of Human Adenovirus 5 DNA," *J. Virology,* 52:456–467 (1973).

Guild et al., "Development of Retrovirus Vectors Useful for Expressing Genes in Cultured Murine Embryonal Cells and Hematopoietic Cells In Vivo," *J. Virol.,* 62(10):3795–3801 (1988).

Hirsch, M.S., "Aids Commentary: Azidothymidine," *J. Infect. Dis.,* 157(3):427–431 (1988).

Ho et al., "A T–Cell–Specific Transcriptional Enhancer Element 3' of $C_\alpha$ in the Human T–Cell Receptor a Locus," *Proc. Nat'l Acad. Sci., USA,* 86:6714–6718 (Sep., 1989).

Kantoff et al., "Correction of Adenosine Dearninase Deficiency in Cultured Human T and B Cells by Retrovirus–mediated Gene Transfer," *Proc. Nat'l Acad. Sci., USA,* 83:6563–6567 (Sep., 1986).

Kriegler et al., "Transformation Mediated by the SV40 T Antigens: Separation of the Overlapping SV40 Early Genes with a Retroviral Vector," *Cell,* 38:483–491 (Sep., 1984).

Malim et al., "The HIV–I rev trans–activator Acts Through a Structured Target Sequence to Activate Nuclear Export of Unspliced Viral mRNA," *Nature,* 338:254–257 (1989).

Maniatis et al., *Molecular Cloning: A Laboratory Manual,* Cold Spring Harbor Laboratory, Cold Spring Harbor Press, pp. 22–26 (1982).

Maniatis et al., "Regulation of Inducible and Tissue–Specific Gene Expression," *Science,* 236:1237–1245 (Jun. 5, 1987).

Mansour et al., "Disruption Of The Proto–Oncogene int–2 In Mouse Embryo–Derived Stem Cells: A General Strategy For Targeting Mutations To Non–Selectable Genes," *Nature,* 336:348–352 (Nov., 1988).

Mariman, E.C.M., "New Strategeoies for AIDS therapy and Prophylaxis," Nature, 318:414 (1985).

Mitsuya et al., "Strategies for Antiviral Therapy in AIDS," *Nature,* 325:773–778 (Feb. 26, 1987).

Moolten, F.L., "An Alternative to the Magic Bullet Paradigm for Specific Cancer Therapy," *Medical Hypotheses,* 24:43–51 (1987).

Moolten, F.L., "Tumor Chemosensitivity Conferred by Inserted Herpes Thymidine Kinase Genes: Paradigm for a Prospective Cancer Control Strategy," *Cancer Research*, 46:5276–5281 (Oct., 1986).

Muesing et al., "Regulation of mRNA Accumulation by a Human Immunodeficiency Virus Trans–Activator Protein," *Cell*, 48:691–701 (1987).

Nabel et al., "Alternative Mechanisms for Activation of Human Immunodeficiency Virus Enhancer in T Cells," *Science*, 239:1299–1302 (1988).

Overhauser et al., "Generation of Glucoconicoid–Responsive Moloney Murine Leukemia Virus by Insertion of Regulatory Sequences from Murine Mammary Tumor Virus into the Long Terminal Repeat," *J. Virol.*, 54(1):133–144 (1985).

Palmiter et al., "Cell Lineage Ablation In Transgenic Mice By Cell–Specific Expression Of A Toxin Gene," *Cell*, 80:435–443 (1987).

Patarca et al., "rpt–1, An Intracellular Protein From Helper/Inducer T Cells That Regulates Gene Expression of Interleukin 2 Receptor and human Immunodeficiency Virus Type 1," *Proc. Nat'l Acad. Sci.*, 85:2733–2737 (1988).

Peterlin et al., "Elevated Levels of mRNA Can Account for the Trans–activation of Human Immunodeficiency Virus," *Proc. Nat'l Acad. Sci., USA*, 83:9734–9738 (Dec., 1986).

Phelps et al., "The Human Papillomavirus Type 16 E7 Gene Encodes Transactivation and Transformation Functions Similar to Those of Adenovirus EIA," *Cell*, 53:539–547 (May 20, 1988).

Piatak et al., "Expression of Soluble and Fully Functional Ricin A Chain in *Escherichia coli* is Temperature–Sensitive," *J. Biol. Chem.*, 263(10):4837–4843 (1988).

Selsted et al., "Primary Structures of Three Human Neutrophil Defensins," *J. Clin. Invest.*, 76:1436–1439 (Oct., 1985).

Shinnick et al., "Nucleotide Sequence of Moloney Murine Leukaemia Virus," *Nature*, 293:543–548 (1981).

Smith et al., "Blocking of HIV–I Infectivity by a Soluble, Secreted Form of the Antigen," *Science*, 238:1704–1707 (Dec. 18, 1987).

Sodroski et al., "Trans–Acting Transcriptional Regulation of Human T–Cell Leukemia Virus Type III Long Terminal Repeat," *Science*, 22:171–173 (Jan. 11, 1985).

Sodroski et al., "Location Of The Trans–Activating Region On The Genome of Human T–Cell Lymphotropic Virus Type III," *Science*, 229:74–77 (Jul. 5, 1985).

Treisman, "Identification of a Protein–Binding Site That Mediates Transcriptional Response of the C–fos Gene to Serum Factors," *Cell*, 46:567–574 (Aug. 15, 1986).

Van Beveran et al., "Nucleotide Sequence of the Genome of a Murine Sarcoma Virus," *Cell*, 27:97–108 (1981).

Walbot et al., "Plant Development and Ribozymes for Pathogens," *Nature*, 334:196–197 (Jul. 21, 1988).

Wasmoen et al., "Biochemical and Amino Acid Sequence Analysis of Human Eosinophil Granule Major Basic Protein," *J. Biol. Chem.*, 263:12559–12563 (1988).

Yee et al., "Gene Expression From Transcriptionally Disabled Retroviral Vectors," *Proc. Nat'l Acad. Sci., USA*, 84:5197–5201 (Aug., 1987).

Yu et al., "Self–Inactivating Retroviral Vectors Designed for Transfer of Whole Genes into Mammalian Cells," *Proc. Nat'l Acad. Sci., USA*, 83:3194–3198 (May, 1986).

Maxwell et al., "Regulated Expression of a Diptheria Toxin A–Chain Gene Transfected Into Human Cells: Possible Strategy For Inducing Cancer Cell Suicide," *Cancer Research*, 46:4660–4664 (1986).

Maxwell et al., "Regulated Expression of a Transfected Toxin Gene," *J. Cell. Biochem., Supplement* 10D:39 (Abstract N93) (1986).

Maxwell et al., "HTLV–Regulated Expression of a Transfected Diphtheria Toxin Gene," *J. Cell. Biochem., Supplement* 11D:67 (Abstract P314) (1987).

Harrison et al., "Toward HIV–Regulated Expression of a Diptheria Toxin A Gene In Transfected Cells," *J. Cell. Biochem., Supplement* 13B:302 (Abstract G418) (Jan. 21, 1989).

Verma et al., "Expression and Regulation of Rat Growth Hormone Gene in Mouse Fibroblasts," In: *Eukaryotic Viral Vectors*, Gluzman, Y. (Ed.), Cold Spring Harbor Laboratory, pp. 159–164 (1982).

Arnold et al., "Vaccine Development for Aids Through Molecular Surgery of a Human Common Cold Virus Surface," *J. Cell. Biochem.*, L401:145 (1990).

Buseyne et al., "Detection of HIV–Specific Cell–mediated Cytotoxicity in the Peripheral Blood from Infected Children," *J. Immunology*, 150(8):3569–3581 (1993).

Carmichael et al., "Quantitative Analysis of the Human Immunodeficiency Virus Type 1 (HIV–1)–Specific Cytotoxic T Lymphocyte (CTL) Response at Different Stages of HIV–1 Infection: Differential CTL Responses to HIV–1 and Epstein–Barr Virus in Late Disease," *J. Exp. Med.*, 177:249–256 (1993).

Chada et al., "Cross–Reactive Lysis of Human Targets Infected with Prototypic and Clinical Human Immunodeficiency Virus Type 1 (HIV–1) Strains by Murine Anti–HIV–1 IIIB env–Specific Cytotoxic T Lymphocytes," *J. Virol.* 67(6):3409–3417 (1993).

Dadaglio et al., "Enhancement of HIV–specific Cytotoxic T Lymphocytes Responses by Zidovudine (AZT) Treatment," *Clin. Ex. Immunol.*, 87:7–14 (1992).

De Baetselier et al., "Differential Expression of H–2 Gene Products in Tumour Cells is Associated with Their Metastatogenic Properties," *Nature*, 288:179–181 (1980).

Doherty et al., "Recombinant Vaccinia Viruses and the Development of Immunization Strategies Using Influenza Virus," *J. Inf. Disease*, 159(6):1119–1122 (1989).

Ellrodt et al., "The Hidden Dangers of AIDS Vaccination," *Nature*, 325:765 (1987).

Fauci et al., "Development and Evaluation of a Vaccine for Human Immunodeficiency Virus (HIV) Infection," *Ann. Intern. Med.*, 110:373–385 (1989).

Fisher–Hoch et al., "Protection of Rhesus Monkeys From Fatal Lassa Fever by Vaccination With a Recombinant Vaccinia Virus Containing the Lassa Virus Glycoprotein," *Proc. Nat'l Acad. Sci., USA*, 86:317–321 (1989).

Holt et al., "Inducible Production of c–fos Antisense RNA Inhibits 3T3 Cell Proliferation," *Proc. Nat'l Acad. Sci., USA*, 83:4794–4798 (1986).

Hu et al., "Effect of Immunization with a Vaccinia–HIV env Recombinant on HIV Infection of Chimpanzees," *Nature*, 328:721–723 (1987).

Hussey et al., "A Soluble CD4 Protein Selectively Inhibits HIV Replication and Syncytium Formation," *Nature*, 331:78–81 (1988).

Izant & Weintraub, "Constitutive and Conditional Suppression of Exogenous and Endogenous Genes by Anti–Sense RNA," *Science*, 229:345–352 (1985).

Joly et al., "Cell–Mediated Suppression of HIV–Specific Cytotoxic T Lymphocytes," *J. Immunol.*, 143(7):2193–2201 (1989).

Lathe et al., "Tumour Prevention and Rejection With Recombinant Vaccinia," *Nature*, 326:878–880 (1987).

Ledley et al., "Retroviral–mediated Gene Transfer of Human Phenylalanine Hydroxylase into NIH 3T3 and Hepatoma Cells," *Proc. Nat'l Acad. Sci.*, 83:409–413 (Jan., 1986).

Lotze et al., "Recent Advances in Cellular Immunology: Implication for Immunity to Cancer," *Immunology*, 11:190–193 (1990).

McCormick, D., "Human Gene Therapy: The First Round," *BioTechnology*, 3(8):689–693 (1985).

McCune et al., "Endoproteolytic Cleavage of gp160 Is Required for the Activation of Human Immunodeficiency Virus," *Cell*, 53:55–67 (1988).

Mercola et al., "Insertion of a New Gene of Viral Origin into Bone Marrow Cells of Mice," *Science*, 208:1033–1035 (1980).

Miedema et al., "Maintenance of High Level Cytotoxic T–Cell (CTL) Response in Long–Term Survivors of HIV Infection," *J. Cell. Biochem.*, Supplement 17D:75 (Abstract N350) (1993).

Mulligan, R.C., "Construction of Highly Transmissible Mammalian Cloning Vehicles Derived from Murine Retroviruses," *Experimental Manipulation of Gene Expression*, 8:155–173 (1983).

Mosier et al., "Resistance to Human Immunodeficiency Virus 1 Infection of SCID Mice Reconstituted With Peripheral Blood Leukocytes from Donors Vaccinated With Vaccinia gp160 and Recombinant gp160," *Proc. Nat'l Acad. Sci., USA*, 90:2443–2447 (1993).

Newell et al., "Herpes Simplex Virus–Induced Stromal Keratitis: Role of T–Lymphocyte Subsets in Immunopathology," *J. Virol.*, 63(2):769–775 (1989).

Salk, J., "Prospects for the Control of AIDS by Immunizing Seropositive Individuals," *Nature*, 327:473–476 (1987).

Shinitzky et al., "Cancer Immunotherapy With Autologous and Allogeneic Vaccines: A Practical Overview," *EORTC Gentitourinary Group Monograph Basic Research and Treatment of Renal Cell Carcinoma Metastasis*, 9:95–125 (1990).

Strebel et al., "The HIV 'A' (sor) Gene Product is Essential for Virus Infectivity," *Nature*, 358:728–730 (1987).

Temin, H.M., "Retrovirus Vectors: Promise and Reality," *Science*, 246:983 (1989).

Torpey, III et al., "Effects of Adoptive Immunotherapy with Autologous CD8+ T Lymphocytes on Immunologic Parameters: Lymphocytes Subsets and Cytotoxic Activity," *Clinical Immunol. & Immunopath.*, 68(5):263–272 (1993).

Voss et al., "Potential Significance of the Cellular Immune Response against the Macaque Strain of Simian Immunodeficiency Virus ($SIV_{MAC}$) in Immunized and Infected Rhesus Macaques," *J. Gen. Virology*, 73:2273–2281 (1992).

Yasutomi et al., "Simian Immunodeficiency Virus–Specific CD8+ Lymphocyte Response in Acutely Infected Rhesus Monkeys," *J. Virol.*, 67(3):1707–1711 (1993).

Zagury et al., "Immunization Against AIDS in Humans," *Nature*, 326:249–250 (1987).

Czarniecki et al., "Synergistic Antiviral and Antiproliferative Activities of *Escherichia coli*–Derived Human Alpha, Beta, and Gamma Interferon," *J. of Virology*, 49(2):490–496 (Feb., 1984).

Davison et al., "The Complete DNA Sequence of Varicella–Zoster Virus," *J. Gen. Virol.*, 67:1759–1816 (1986).

Deen et al., "A Soluble Form of CD4 (T4) Protein Inhibits AIDS Virus Infection," *Nature*, 331:82–84 (Jan. 7, 1988).

Howell et al., "Gene Therapy for Thioguanine–resistant Human Leikemia," *Mol. Biol. Med.*, 4:157–168 (1987).

Katoh et al., "Inhibition of Retroviral Protease Activity by an Aspartyl Proteinase Inhibitor," *Nature*, 329:654–656 (Oct. 15, 1987).

Rein et al., "Myristylation Site in $Pr65^{gag}$ is Essential for Virus Particle Formation by Moloney Murine Leukemia Virus," *Proc. Nat'l Acad. Sci., USA*, 83:7246–7250 (Oct., 1986).

Sleckman et al., "Expression and Function of CD4 in a Murine T–Cell Hybridoma," *Nature*, 328:351–353 (Jul. 23, 1987).

Stratowa et al., "Recombinant Retroviral DNA Yielding High Expression of Hepatitis B Surface Antigen," *EMBO J.*, 1(12):1573–1578 (1982).

Tabin et al., "Adaptation of a Retrovirus as a Eucaryotic Vector Transmitting the Herpes Simplex Virus Thymidine Kinase Gene," *Mol. & Cell. Biology*, 2(4):426–436 (Apr., 1982).

Temin, H.M., "Retrovirus Vectors for Gene Transfer: Efficient Integration Into and Expression of Exogenous DNA in Vertebrate Cell Genomes," In: *Gene Transfer*, Kucherlapati (Ed.), Plenum Press, New York, pp. 149–187 (1986).

Wachsman et al., "HTLV×Gene Mutants Exhibit Novel Transcriptional Regulatory Phenotypes," *Science*, 235:674–677 (Feb. 6, 1987).

Lang et al., "Expression of a Hemopoietic Growth Factor cDNA in a Factor–Dependnet Cell Line Results in Autonomous Growth and Tumorigenicity," *Cell*, 43:531–542 (1985).

Aldovini et al., *Nature* 351:479–482, 1991.

Altmann, *Nature* 338:512–514, 1989.

Ameisen et al., *Immunology Today* 12:102–105, 1991.

Anderson et al., *Som. Cell and Mol. Genetics* 15:215–227, 1989.

Anderson, *Science* 226:401–409, 1984.

Armentano et al., *J. Virology* 61:1647–1650, 1987.

Baltimore, *Nature* 335:395–396, 1988.

Barnd et al., *PNAS* 86:7159–7163, 1989.

Berkner, *Biotechniques* 6:616–629, 1988.

Bernards et al., *Cell* 47:667–674, 1986.

Bernards et al., *PNAS* 84:6854–6858, 1987.

Bix et al., *Nature* 349:329–331, 1991.

Bolognesi et al., *Cancer Research (Suppl.)* 45:4700s–4705s, 1985.

Braakman et al., *Int. J. Cancer* 46:475–480, 1990.

Braciale et al., *Immunology Reviews* 98:95–114, 1987.

Bubenik et al., *Immunology Letters* 19:279–282, 1988.

Butini et al., *J Cell. Biochem. Suppl.* 18B: 147, Abstract J306, 1994.

Carey, *Business Week*, pp. 133, 136, May 1, 1989.

Carr et al., *Blood* 62:180–185, 1983.

Cepko et al., *Cell* 37:1053–1062, 1984.

Cepko, *Neuron* 1:345–353, 1988.

Chakrabarti et al., *Nature* 320:535–537, 1986.

Chan et al., *J. Natl. Cancer Inst.* 52(2):473–481, 1974.

Cline et al., *Nature* 284:422–425, 1980.

Collins et al., *J. Cell. Physiology* 137:293–298, 1988.

Cone et al., *Endocrinology* 123:2067–2074, 1988.

Cone et al., *PNAS* 81:6349–6353, 1984.

Cortes et al., *J. Surg. Onco.* 25:289–295, 1984.

Crowley et al., *Cancer Research* 50:492–498, 1990.

Culliton, News and Comment, *Science* 246:746–751, 1989.

Dallo et al., *Virology* 173:323–329, 1989.

Donner et al., *J. Virol* 41(2):489–500, 1982.

Earl et al., *J. Virology* 65:31–41, 1991.
Embretson et al., *J. Virology* 60:662–668 1986.
Episkopou et al., *PNAS* 81:4657–4661, 1984.
Estin et al., *PNAS* 85:1052–1056, 1988.
Evans et al., *Nature* 339:385–388, 1989.
Faraji–Shadan et al., *Medical Hypothesis* 32:81–84, 1990.
Flexner et al., *Virology* 166:339–349, 1988.
Fox, *Bio/Technology* 12:128, 1994.
Friedmann, *Ann. N.Y. Acad. Sci.* 265:141–152, 1975.
Friedmann, *Science* 244:1275–1281, 1989.
Gansbacher et al., *Cancer Research* 50:7820–7825, 1990.
Gattoni–Celli et al., *PNAS* 85:8543–8547, 1988.
Gilboa et al., *Trends in Genetics* 10(4):139–144, 1994.
Gilboa, *The Biology of Hematopoiesis*, pp. 301–311, 1990.
Gruber et al., *Science* 230:1057–1061, 1985.
Guarini et al., *Cancer Immunol. Immunother.* 30:262–268, 1989.
Hatzoglou et al., *J. Biol. Chem.* 263:17798–17808, 1988.
Haynes, *Science* 260:1279–1286, 1993.
Hellerman et al., *PNAS* 81:5340–5344, 1984.
Hester et al., *J Nat. Cancer Inst.* 82:1209–1214, 1990.
Hoffenbach et al., *J. Immunol.* 142:452–462, 1989.
Holzman, *Genetic Engineering News* 15(15):1, 21, 1995.
Hu et al., *Virology* 179:321–329, 1990.
Hunt et al., *J. Virology* 62:3014–3019, 1988.
Isobe et al., *J. Nat. Cancer Inst.* 81: 1823–1828, 1989.
Jaroff, *Time*, pp. 74–76, Sep. 24, 1990.
Johnston et al., *Science* 260:1286–1293, 1993.
Jolly et al., *Biotechnology Therapeutics* 2(12):179–193, 1990–1991.
Joyner et al., *Developmental Biology Using Purified Genes*, Academic Press, 1981.
Joyner et al., *Nature* 305:556–558, 1983.
Kantoff et al., *J. Exp. Med.* 166:219–234, 1987.
Kasid et al., *PNAS* 87:473–477, 1990.
Kast et al., *Cell* 59:603–614, 1989.
Keller et al., *Nature* 318:149–154, 1985.
Klavinskis et al., *J. Virol.* 63(10):4311–4316, 1989.
Koenig et al., *J. Immunol.* 145:127–135, 1990.
Kohn, *Blood Cells* 13:285–298, 1987.
Korman et al., *PNAS* 84:2150–2154, 1987.
Kourilsky et al., *Adv. in Immunol.* 45:107–193, 1989.
Ledley, *J. Pediatrics* 110:1–8, 1987.
Lee, *Can. Med. Assoc. J.* 134:311–313, 1986.
Levy, *Microbiological Reviews* 57(1):183–289, 1993.
Lewis, *Genetic Engineering News* 15(7):1, 17, 25, 1995.
Linial et al., *Cell* 15:1371–1381, 1978.
Linial, *J. Virology* 38:380–382, 1981.
Lotteau et al., *J. Exp. Med.* 169:351–356, 1989.
Luytjes et al., *Cell* 59:1107–1113, 1989.
Mason et al., *Science* 234:1372–1378, 1986.
McAleer et al., *Nature* 307:178–180, 1984.
McCune et al., *Cancer Immunol. Immunother.* 32:62–66, 1990.
McMichael et al., *The New England J. Med.* 309:13–17, 1983.
Merz, *JAMA* 257:150–151, 1987.
Michel et al., *Eur. J. Immunol.* 18:1917–1924, 1988.
Miller et al., *Mol. And Cell. Biol.* 5:431–437, 1985.
Miller et al., *Mol. And Cell. Biol.* 6:2895–2902, 1986.
Miller et al., *PNAS* 80:4709–4713, 1983.
Miller et al., *Science* 225:630–632, 1984.
Miller, *Human Gene Therapy* 1:5–14, 1990.
Morgan et al., *Science* 237:1476–1479, 1987.

Morrow; *Ann N.Y. Acad Sci.* 265 13–21 1975.
Nabel et al., *Science* 244:1342–1344, 1989.
Nixon et al., *Nature* 336:484–487, 1988.
Overell et al., *Mol. And Cell. Biol.* 8:1803–1808, 1988.
Palmer et al., *PNAS* 88:1330–1334, 1991.
Panicali et al., *PNAS* 80:5364–5368, 1983.
Plata et al., *Nature* 328:348–351, 1987.
Quinnan, Jr. et al., *New Eng. J. Med.* 307:7–13, 1982.
Redfield et al., *The New England J. Med.* 324:1677–1684, 1991.
Reif, *Cancer Research* 45:25–31, 1985.
Reimann et al., *J. Immunol. Methods* 89:93–101, 1986.
Rosenberg et al., *The New England J. Med.* 323:570–578, 1990.
Rosenfeld et al., *Science* 252:431–434, 1991.
Rota et al., *Virus Research* 16:83–93, 1990.
Rouse et al., *Rev. Infect. Dis.* 10:16–33, 1988.
Rubenstein et al., *PNAS* 81:7137–7140, 1984.
Ruprecht et al., *PNAS* 87:5558–5562, 1990.
Ruscetti et al., *J. Virol.* 35(1):259–264, 1980.
Sabin et al., *J. Biol. Standardization* 1:115–118, 1973.
Saito et al., *Immunological Reviews* 101:81–193, 1988.
Shimotohno et al., *Cell* 26:67–77, 1981.
Siu et al., *J. Immunology* 143:3813–3820, 1989.
Smith et al., *PNAS* 86:5557–5561, 1989.
St. Louis et al., *PNAS* 85:3150–3154, 1988.
Stover et al., *Nature* 351:456–460, 1991.
Strair et al., *J. Virology* 62:4756–4759, 1988.
Stuhlmann et al., *PNAS* 81:7151–7155, 1984.
Suter et al., *Veterinary Immunology and Immunopathology* 7:131–138, 1984.
Takahashi et al., *PNAS* 85:3105–3109, 1988.
Takahashi et al., *Science* 246:118–121, 1989.
Tellier and Weber, *Nature* 318:414, 1985.
Thomason and Booth, *Amer. J Physiology* 258:C578–C581, 1990.
Townsend et al., *Cell* 42:457–467, 1985.
Traversari et al., *J. Immunol.* 142:2887–2894, 1989.
Van Den Eynde et al., *Int. J. Cancer* 44:634–640, 1989.
Verma, *Scientific American* 262:68–72, 81–84, 1990.
Walker et al., *Nature* 328:345–348, 1987.
Walker et al., *Science* 240:64–66, 1988.
Wallich et al., *Nature* 315:301–305, 1985.
Warner et al., *AIDS Res. And Human Retrovir.* 7(8):645–655, 1991.
Watanabe et al., *Mol. And Cell. Biol.* 3:2241–2249, 1983.
Watanabe et al., *PNAS* 79:5986–5990, 1982.
Weber and Jay, *Curr. Top. Microbiol. Immunol.* 137:140–147, 1988.
Weber et al., *J. Exp. Med* 166:1716–1733, 1987.
Wei et al., *J. Virology* 39:935–944, 1981.
Weis et al., *Mol. & Cell. Biol.* 5:1379–1384, 1985.
Weis et al., *PNAS* 81:4879–4883, 1984.
Wilson et al., *Science* 244:1344–1346, 1989.
Wilson et al., *Science* 248:1413–1416, 1990.
Wolff et al., *PNAS* 86:9011–9014, 1989.
Wong et al., *Genes Dev.* 1:358–365, 1987.
Xu et al., *Virology* 171:331–341, 1989.
Yap et al., *Nature* 273:238–239, 1978.
Zarling et al., *J. Immunol.* 139:988–990, 1987.
Zarling et al., *Nature* 323:344–346, 1986.
Zbar et al., *Cancer Research* 43:46–53, 1983.
Zinkenagel et al., *J. Exp. Med.* 145:644–651, 1977.
Zwiebel et al., *Ann. N.Y. Acad. Sci.* 618:394–404, 1990.

RECOMBINANT RETROVIRUSES EXPRESSING A PROTEIN THAT CONVERTS A PRO-DRUG INTO A CYTOTOXIC AGENT

CROSS-REFERENCE TO RELATED APPLICATION

This application is a division of U.S. patent application Ser. No. 08/136,739, filed Oct. 12, 1993; which was a continuation of U.S. patent application Ser. No. 07/395,932, filed Aug. 18, 1989, now abandoned; which was a continuation-in-part of U.S. patent application Ser. No. 07/170,515, filed Mar. 21, 1988, now abandoned.

TECHNICAL FIELD

The present invention relates generally to retroviruses, and more specifically, to recombinant retroviruses which are capable of delivering vector constructs to susceptible target cells. These vector constructs are typically designed to express desired proteins in target cells, for example, proteins which stimulate immunogenic activity or which are conditionally active in defined cellular environments.

BACKGROUND OF THE INVENTION

Although bacterial diseases are, in general, easily treatable with antibiotics, very few effective treatments or prophylactic measures exist for many viral, cancerous, and other nonbacterial diseases, including genetic diseases. Traditional attempts to treat these diseases have employed the use of chemical drugs. In general, these drugs have lacked specificity, exhibited high overall toxicity, and thus have been therapeutically ineffective.

Another classic technique for treating a number of nonbacterial diseases involves the elicitation of an immune response to a pathogenic agent, such as a virus, through the administration of a noninfectious form of the agent, such as a killed virus, thereby providing antigens from the pathogenic agent which would act as an immunostimulant.

A more recent approach for treating viral diseases, such as acquired immunodeficiency syndrome (AIDS) and related disorders, involves blocking receptors on cells susceptible to infection by HIV from receiving or forming a complex with viral envelope proteins. For example, Lifson et al. (*Science* 232:1123-1127, 1986) demonstrated that antibodies to CD4 (T4) receptors inhibited cell fusion (syncytia) between infected and noninfected CD4 presenting cells in vitro. A similar CD4 blocking effect using monoclonal antibodies has been suggested by McDougal et al. (*Science* 231:382-385, 1986). Alternatively, Pert et al. (*Proc. Natl. Acad. Sci. USA* 83:9254-9258, 1986) have reported the use of synthetic peptides to bind T4 receptors and block HIV infection of human T-cells, while Lifson et al. (*J. Exp. Med.* 164:2101, 1986) have reported blocking both syncytia and virus/T4 cell fusion by using a lectin which interacts with a viral envelope glycoprotein, thereby blocking it from being received by CD4 receptors.

A fourth, recently suggested technique for inhibiting a pathogenic agent, such as a virus, which transcribes RNA is to provide antisense RNA which complements at least a portion of the transcribed RNA, and binds thereto, so as to inhibit translation (To et al., *Mol. Cell. Biol.* 6:758, 1986).

However, a major shortcoming of the techniques described above is that they do not readily lend themselves to control as to the time, location or extent to which the drug, antigen, blocking agent or antisense RNA are utilized. In particular, since the above techniques require exogenous application of the treatment agent (i.e., exogenous to the sample in an in vitro situation), they are not directly responsive to the presence of the pathogenic agent. For example, it may be desirable to have an immunostimulant expressed in increased amounts immediately following infection by the pathogenic agent. In addition, in the case of antisense RNA, large amounts would be required for useful therapy in an animal, which under current techniques would be administered without regard to the location at which it is actually needed, that is, at the cells infected by the pathogenic agent.

As an alternative to exogenous application, techniques have been suggested for producing treatment agents endogenously. More specifically, proteins expressed from viral vectors based on DNA viruses, such as adenovirus, simian virus 40, bovine papilloma, and vaccinia viruses, have been investigated. By way of example, Panicali et al. (*Proc. Natl. Acad. Sci. USA* 80:5364, 1983) introduced influenza virus hemagglutinin and hepatitis B surface antigens into the vaccinia genome and infected animals with the virus particles produced from such recombinant genes. Following infection, the animals acquired immunity to both the vaccinia virus and the hepatitis B antigen.

However, a number of difficulties have been experienced to date with viral vectors based on DNA viruses. These difficulties include (a) the production of other viral proteins which may lead to pathogenesis or the suppression of the desired protein; (b) the capacity of the vector to uncontrollably replicate in the host, and the pathogenic effect of such uncontrolled replication; (c) the presence of wild-type virus which may lead to viremia; and (d) the transitory nature of expression in these systems. These difficulties have virtually precluded the use of viral vectors based on DNA viruses in the treatment of viral, cancerous, and other nonbacterial diseases, including genetic diseases.

Due to the nontransitory nature of their expression in infected target cells, retroviruses have been suggested as a useful vehicle for the treatment of genetic diseases (for example, see F. Ledley, *The Journal of Pediatrics* 110:1, 1987). However, in view of a number of problems, the use of retroviruses in the treatment of genetic diseases has not been attempted. Such problems relate to (a) the apparent need to infect a large number of cells in inaccessible tissues (e.g., brain); (b) the need to cause these vectors to express in a very controlled and permanent fashion; (c) the lack of cloned genes; (d) the irreversible damage to tissue and organs due to metabolic abnormalities; and (e) the availability of other partially effective therapies in certain instances.

In addition to genetic diseases, other researchers have contemplated using retroviral vectors to treat nongenetic diseases (see, for example, EP 243,204—Cetus Corporation; Sanford, *J. Theor. Biol.* 130:469, 1988; Tellier et al., *Nature* 318:414, 1985; and Bolognesi et al., *Cancer Res.* 45:4700, 1985).

Tellier et al. suggested protecting T-cell clones by apparently infecting stem cells with "defective" HIV having a genome which could express antisense RNA to HIV RNA. Bolognesi et al. have suggested the concept of generating a nonvirulent HIV strain to infect stem cells so that T4 cells generated therefrom would carry interfering, nonvirulent forms of virus and thereby protect those cells from infection by virulent HIV. However, it would appear that the "attenuated" or "defective" HIV viruses used in both of the foregoing papers could reproduce (i.e., are not replication defective) such that the resulting viruses could infect other cells, with the possibility of an increased risk of recombination with previously present HIV or other sequences, leading to loss of attenuation. Non-nonreplicative forms would necessitate a defective helper or packaging line for HIV. However, since the control of HIV gene expression is complex, such cells have to date not been constructed. Furthermore, as the infecting attenuated or defective virus is not chimeric (a "nonchimeric" retrovirus being one with substantially all of its vector from the same retrovirus species), even if they were made replication defective, for example, by deletion from their genomes of an essential element, there still exists a significant possibility for recombination within the host cells with resultant production of infectious viral particles.

Although Sanford (*J. Theor. Biol.* 130:469, 1988) has also proposed using a genetic cure for HIV, he notes that due to the potential that exists for creating novel virulent viruses via genetic recombination between natural AIDS virus and therapeutic retroviral vectors carrying anti-HIV genes, retroviral gene therapy for AIDS may not be practical. Similarly, while McCormick & Kriegler (EP 243,204 A2) have proposed using retroviral vectors to deliver genes for proteins, such as tumor necrosis factor (TNF), the techniques they describe suffer from a number of disadvantages.

SUMMARY OF THE INVENTION

Briefly stated, the present invention provides recombinant retroviruses carrying a vector construct capable of preventing, inhibiting, stabilizing or reversing infectious, cancerous, auto-immune or immune diseases. Such diseases include HIV infection, melanoma, diabetes, graft vs. host disease, Alzheimer's disease, and heart disease.

The present invention is directed, in part, toward methods for (a) stimulating a specific immune response, either humoral or cell-mediated, to an antigen or pathogenic antigen; (b) inhibiting a function of a pathogenic agent, such as a virus; and (c) inhibiting the interaction of an agent with a host cell receptor, through the use of recombinant retroviruses.

More specifically, within one aspect of the present invention, a method for stimulating a specific immune response is provided, comprising infecting susceptible target cells with recombinant retroviruses carrying a vector construct that directs the expression of an antigen or modified form thereof in infected target cells. For purposes of the present invention, the term "infecting" includes the introduction of DNA sequences through viral vectors, transfection or other means, such as microinjection, protoplast fusion, etc. Where an immune response is to be stimulated to a pathogenic antigen, the recombinant retrovirus is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogs thereof (e.g., Altmann et al., *Nature* 338:512, 1989). Cells infected with retroviral vectors are expected to do this efficiently because they closely mimic genuine viral infection.

This aspect of the invention has a further advantage over other systems that might be expected to function in a similar manner, in that the presenter cells are fully viable and healthy, and no other viral antigens (which may well be immunodominant) are expressed. This presents a distinct advantage since the antigenic epitopes expressed can be altered by selective cloning of sub-fragments of the gene for the antigen into the recombinant retrovirus, leading to responses against immunogenic epitopes which may otherwise be overshadowed by immunodominant epitopes. Such an approach may be extended to the expression of a peptide having multiple epitopes, one or more of the epitopes derived from different proteins. In addition, the present invention provides for a more efficient presentation of antigens through the augmentation or modification of the expression of presenting accessory proteins (e.g., MHC I, ICAM-1, etc.) in antigen presenting cells.

An immune response can also be achieved by transferring to an appropriate immune cell (such as a T lymphocyte) the gene for the specific T-cell receptor which recognizes the antigen of interest (in the context of an appropriate MHC molecule if necessary), for an immunoglobulin which recognizes the antigen of interest, or for a hybrid of the two which provides a CTL response in the absence of the MHC context.

In the particular cases of disease caused by HIV infection, where immunostimulation is desired, the antigen generated from the recombinant retroviral genome is of a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the antigen selected is modified to reduce the possibility of syncytia, to avoid expression of epitopes leading to a disease enhancing immune response, to remove immunodominant, but strain-specific epitopes or to present several strain-specific epitopes, and allow a response capable of eliminating cells infected with most or all strains of HIV. Antigens from other HIV genes, such as gag, pol, vif, nef, etc., may also provide protection in particular cases.

In another aspect of the present invention, methods for inhibiting a function of a pathogenic agent necessary for disease, such as diseases caused by viral infections, cancers or immunological abnormalities, are disclosed. Where the pathogenic agent is a virus, the inhibited function may be selected from the group consisting of adsorption, replication, gene expression, assembly, and exit of the virus from infected cells. Where the pathogenic agent is a cancerous cell or cancer-promoting growth factor, the inhibited function may be selected from the group consisting of viability, cell replication, altered susceptibility to external signals, and lack of production of anti-oncogenes or production of mutated forms of anti-oncogenes. Such inhibition may be provided through recombinant retro-viruses carrying a vector construct encoding "inhibitor palliatives," such as: (a) antisense RNA; (b) a mutant protein analogue to a pathogenic protein, which interferes with expression of the pathogenic state; (c) a protein that activates an otherwise inactive precursor; (d) defective interfering structural proteins; (e) peptide inhibitors of viral proteases or enzymes; (f) tumor suppressor genes; or (g) a RNA ribozyme capable of specifically cutting and degrading RNA molecules corresponding to the pathogenic state. Alternatively, such inhibition is attained by a recombinant retrovirus capable of site-specific integration into pathogenic genes, thereby disrupting them.

Such inhibition may also be accomplished through the expression of a palliative that is toxic for a diseased cell. Where a toxic palliative is to be produced by cells containing the recombinant viral genome, it is important that either the recombinant retrovirus infect only target cells or express the palliative only in target cells, or both. In either case, the final toxic agent is localized to cells in the pathogenic state. Where expression is targeted, the pathogenic agent controlling expression of the toxic palliative could be, for instance, a protein produced through transcription and translation of a pathogenic viral genome present in the cell.

It should be understood in the foregoing discussion, and throughout this application, that when reference is made to the viral construct "expressing" or "producing" any substance in a cell, or the like, this in fact refers to the action of the resulting provirus following reverse transcription of the viral RNA in the cell. In the context of a toxic palliative, the consequent killing effect may not necessarily require the permanent integration of the recombinant viral genome into the host genome, but simply a reasonably long-term expression of a toxic palliative gene, in whatever form desirable, over a reasonably long period of time (several days to one month). Thus, other nonintegrating viral vectors such as, but not limited to, adenoviral vectors may be used for this purpose. Examples of conditional toxic palliatives include recombinant retroviruses encoding (a) a toxic gene product under the control of a cell cycle-specific promoter, a tissue-specific promoter or both; (b) a gene product which is conditionally expressed and which in itself is not toxic but which processes within target cells a compound or drug from a nontoxic precursor form to an active toxic form; (c) a gene product which is not in itself toxic, but when processed by a protein, such as protease specific to a viral or other pathogen, is converted into a toxic form; (d) a conditionally expressed reporter gene product on the cell surface which identifies the pathogenic cells for attack, for example, by immunotoxins; (e) conditionally expressed gene products on the cell surface which lead to a toxic effect by interaction with extracellular factors; and (f) conditionally expressed ribozymes specific for RNA molecules essential for viability.

Within a related aspect, the present invention also provides methods for diminishing or eliminating an unwanted or deleterious immune response. Immune suppression, where appropriate, can be achieved by targeting expression of immune suppressive genes, such as the virally derived E3 gene of adenovirus.

Within another aspect of the present invention, methods are disclosed for inhibiting the interaction of viral particles with cells, cells with cells, or cells with factors. The methods generally comprise infecting susceptible cells with a recombinant, replication defective retrovirus which directs the expression of a blocking element in infected cells, the blocking element being capable of binding with a cell receptor (preferably the host cell receptor) either while the receptor is intracellular or on the cell surface, or alternatively, by binding with the agent. In either event, the interaction is blocked.

Regardless of the means by which the recombinant retrovirus exerts its immunogenic or inhibitory action as described above, it is preferred that the retroviral genome be "replication defective" (i.e., incapable of reproducing in cells infected with it). Thus, there will be only a single stage of infection in either an in vitro or in vivo application, thereby substantially reducing the possibility of insertional mutagenesis. Preferably, to assist in this end, the recombinant retrovirus lacks at least one of the gag, pol, or env genes. Further, the recombinant viral vector is preferably chimeric (that is, the gene which is to produce the desired result is from a different source than the remainder of the retrovirus). A chimeric construction further reduces the possibility of recombination events within cells infected with the recombinant retrovirus, which could produce a genome that can generate viral particles.

Within another aspect of the present invention, recombinant retroviruses which are useful in executing the above methods as well as delivering other therapeutic genes are disclosed. The present invention also provides a method for producing such recombinant retroviruses in which the retroviral genome is packaged in a capsid and envelope, preferably through the use of a packaging cell. The packaging cells are provided with viral protein-coding sequences, preferably in the form of two plasmids, which produce all proteins necessary for production of viable retroviral particles, an RNA viral construct which will carry the desired gene, along with a packaging signal which will direct packaging of the RNA into the retroviral particles.

The present invention additionally provides a number of techniques for producing recombinant retroviruses which can facilitate:

i) the production of higher titres from packaging cells;

ii) packaging of vector constructs by means not involving the use of packaging cells;

iii) the production of recombinant retroviruses which can be targeted for preselected cell lines; and iv) the integration of the proviral construct into a preselected site or sites in a cell's genome.

One technique for producing higher titres from packaging cells takes advantage of the discovery that of the many factors which can limit titre from a packaging cell, one of the most limiting is the level of expression of the packaging proteins, namely, the gag, pol, and env proteins, as well as the level of expression of the retroviral vector RNA from the proviral vector. This technique allows the selection of packaging cells which have higher levels of expression (i.e., produce higher concentrations) of the foregoing packaging proteins and vector construct RNA. More specifically, this technique allows selection of packaging cells which produce high levels of what is referred to herein as a "primary agent," which is either a packaging protein (e.g., gag, pol, or env proteins) or a gene of interest to be carried into the genome of target cells (typically as a vector construct). This is accomplished by providing in packaging cells a genome carrying a gene (the "primary gene") which expresses the primary agent in the packaging cells, along with a selectable gene, preferably downstream from the primary gene. The selectable gene expresses a selectable protein in the packaging cells, preferably one which conveys resistance to an otherwise cytotoxic drug. The cells are then exposed to a selecting agent, preferably the cytotoxic drug, which enables identification of those cells which express the selectable protein at a critical level (i.e., in the case of a cytotoxic drug, by killing those cells which do not produce a level of resistance protein required for survival).

Preferably, in the technique briefly described above, the expressions of both the selectable and primary genes is controlled by the same promoter. In this regard, it may be preferable to utilize a retroviral 5' LTR. In order to maximize titre of a recombinant retrovirus from packaging cells, this technique is first used to select packaging cells expressing high levels of all the required packaging proteins, and then is used to select which of these cells, following transfection with the desired proviral construct, produce the highest titres of the recombinant retrovirus.

Techniques are also provided for packaging of vector constructs by means not involving the use of packaging cells. These techniques make use of other vector systems based on viruses such as other unrelated retroviruses, baculovirus, adenovirus, or vaccinia virus, preferably adenovirus. These viruses are known to express relatively high levels of proteins from exogenous genes provided therein. For such DNA virus vectors, recombinant DNA viruses can be produced by in vivo recombination in tissue culture between viral DNA and plasmids carrying retroviral or retroviral vector genes. The resultant DNA viral vectors carrying either sequences coding for retroviral proteins or for retroviral vector RNA are purified into high titre stocks. Alternatively, the constructs can be constructed in vitro and subsequently transfected into cells which provide in trans viral functions missing from the DNA vectors. Regardless of the method of production, high titre ($10^7$ to $10^{11}$ units/ml) stocks can be prepared that will, upon infection of susceptible cells, cause high level expression of retroviral proteins (such as gag, pol, and env) or RNA retroviral vector genomes, or both. Infection of cells in culture with these stocks, singly or in combination, will lead to high-level production of retroviral vectors, if the stocks carry the viral protein and viral vector genes. This technique, when used with adenovirus or other mammalian vectors, allows the use of primary cells (e.g., from tissue explants or cells such as WI38 used in production of vaccines) to produce recombinant retroviral vectors.

In an alternative to the foregoing technique, recombinant retroviruses are produced by first generating the gag/pol and env proteins from a cell line infected with the appropriate recombinant DNA virus in a manner similar to the preceding techniques, except that the cell line is not infected with a DNA virus carrying the vector construct. Subsequently, the proteins are purified and contacted with the desired viral vector RNA made in vitro, transfer RNA (tRNA), liposomes, and a cell extract to process the env protein into the liposomes, such that recombinant retroviruses carrying the viral vector RNA are produced. Within this technique, it may be necessary to process the env protein into the liposomes prior to contacting them with the remainder of the foregoing mixture. The gag/pol and env proteins may also be made after plasmid mediated transfection in eukaryotic cells, in yeast, or in bacteria.

The technique for producing recombinant retroviruses which can be targeted for preselected cell lines utilizes recombinant retroviruses having one or more of the following: an env gene comprised of a cytoplasmic segment of a first retroviral phenotype, and an extracellular binding segment exogenous to the first retroviral phenotype (this binding segment is from a second viral phenotype or from another protein with desired binding properties which is selected to be expressed as a peptide which will bind to the desired target); another viral envelope protein; another ligand molecule in place of the normal envelope protein; or another ligand molecule along with an envelope protein that does not lead to infection of the target cell type.

Techniques for integrating a retroviral genome at a specific site in the DNA of a target cell involve the use of homologous recombination, or alternatively, the use of a modified integrase enzyme which will recognize a specific site on the target cell genome. Such site-specific insertion allows genes to be inserted at sites on the target cells DNA, which will minimize the chances of insertional mutagenesis, minimize interference from other sequences on the DNA, and allow insertion of sequences at specific target sites so as to reduce or eliminate the expression of an undesirable gene (such as a viral gene) in the DNA of the target cell.

It will be appreciated that any of the above-described techniques may be used independently of the others in particular situations, or can be used in conjunction with one or more of the remainder of the techniques.

These and other aspects of the present invention will become evident upon reference to the following detailed description and attached drawings.

BRIEF DESCRIPTION OF THE DRAWINGS

FIG. 4A-1 graphically depicts the results of the experimental protocol of FIG. 3 showing specific killing of BC10MEenv-29 target cells.

FIG. 4A-2 graphically depicts the results of the experimental protocol of FIG. 3 showing resistance to killing in BC10ME control cells.

FIG. 4F-1 illustrates the dose-response relationship of immunizing Balb/c mice with BCenv stimulator cells.

FIG. 4F-2 illustrates the dose-response relationship of immunizing Balb/c mice with BC target cells.

FIG. 4G-1 demonstrates the generation of CTL responses by different H-2$^d$ mouse strains as well as F1 hybrid mice against BCenv target cells.

FIG. 4G-2 demonstrates the generation of CTL responses by different H-2$^d$ mouse strains as well as F1 hybrid mice against BC target cells.

DETAILED DESCRIPTION OF THE INVENTION

I. Immunostimulation

Figure 1:
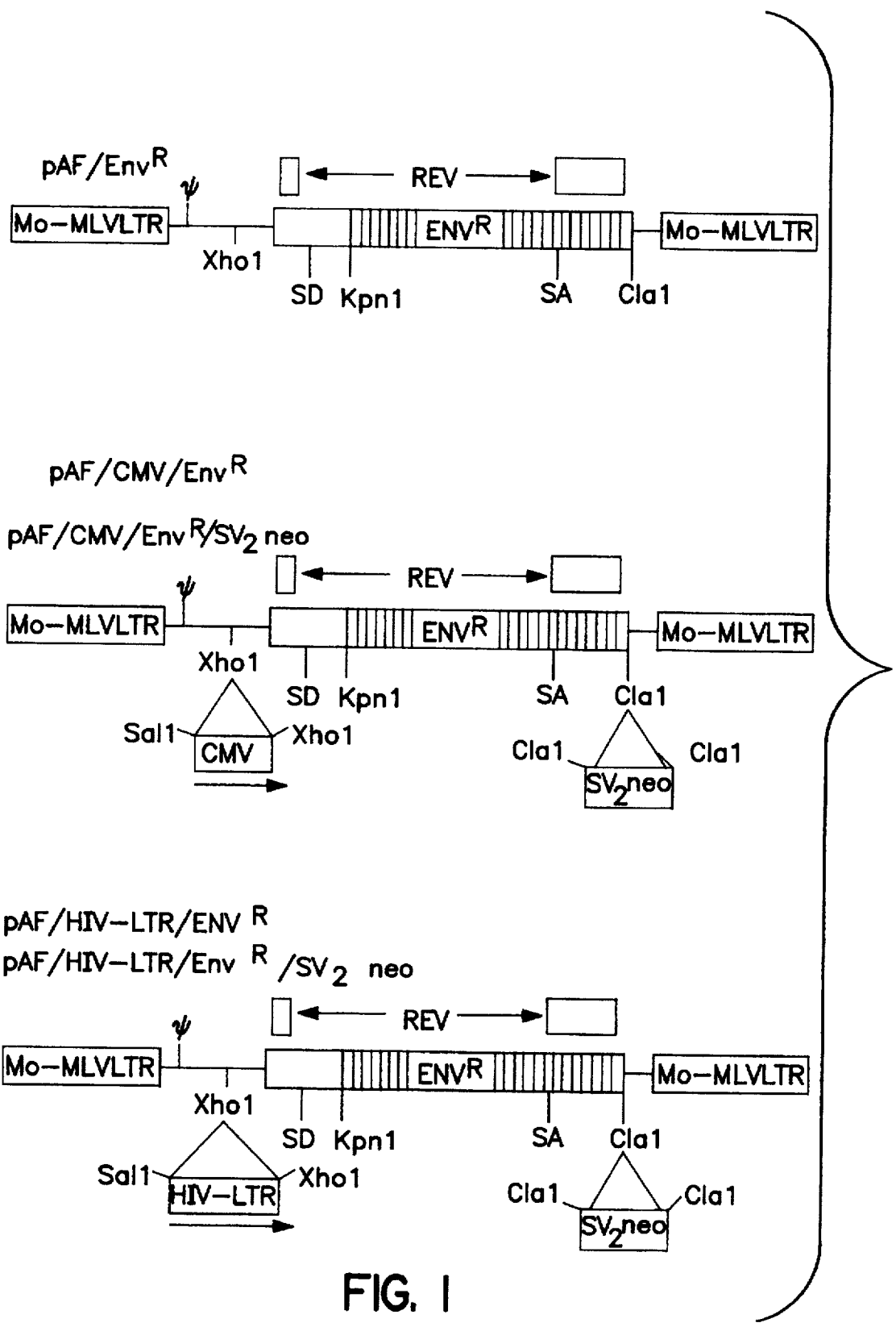
FIG. 1 depicts three different families of vectors used to produce HIV env and which may or may not have the selectable SV-Neo cassette inserted.

The ability to recognize and defend against foreign pathogens is central to the function of the immune system. This system, through immune recognition, must be capable of distinguishing "self" from "nonself" (foreign), which is essential to ensure that defensive mechanisms are directed toward invading entities rather than against host tissues. The fundamental features of the immune system are the presence of highly polymorphic cell surface recognition structures (receptors) and effector mechanisms (antibodies and cytolytic cells) for the destruction of invading pathogens.

Cytolytic T lymphocytes (CTL) are normally induced by the display of processed pathogen-specific peptides in conjunction with the MHC class I or class II cell surface proteins. Also stimulated by this type of antigen presentation are the generation and production antibodies, helper cells and memory cells. Within one embodiment of the present invention, presentation of immunogenic viral determinants in the context of appropriate MHC molecules efficiently induces optimal CTL responses without exposing the patient to the pathogen. This vector approach to immunostimulation provides a more effective means of inducing potent class I-restricted protective and therapeutic CTL responses, because the type of immunity induced by the vector more closely resembles that induced by exposure to natural infection. Based on current knowledge of several viral systems, it is unlikely that exogenously supplied, nonreplicating viral antigens, such as peptides and purified recombinant proteins, will provide sufficient stimulus to induce optimal class I-restricted CTL responses. Alternatively, vector-delivered expression of selected viral proteins or other antigens corresponding to a pathogenic condition, such as cancer, within target cells as described within the present invention provides such a stimulus.

By way of example, in the case of HIV-1 infections, patients develop antibodies specific for a variety of viral envelope-region determinants, some of which are capable of in vitro virus neutralization. Nevertheless, disease progression continues and the patients eventually succumb to the disease. Low-level CTL responses against infected patients' cells (Plata et al., *Nature* 328:348-351, 1987) and against target cells infected with recombinant vaccinia vectors expressing HIV gag, pol, or env (Walker et al., *Nature* 328:345-348, 1987; Walker et al., *Science* 240:64-66, 1988) have been detected in some HIV-1 seropositive patients. In addition, it has recently been shown that murine as well as human CTL can be induced by autologous stimulator cells expressing HIV gp 120 via transfection (Langlade-Demoyan et al., *J. Immunol.* 141:1949, 1988). Improved CTL induction could be therapeutically advantageous to infected patients and provide effective preventive therapy to individuals under noninfectious conditions. HIV infection itself may not be producing an adequate CTL response because other elements associated with HIV infection may prevent proper immune stimulation. In addition, it may be that stimulation of T-cells by infected cells is an interaction that leads to infection of the stimulated T-cells.

HIV is only one example. This approach should be effective against many virally linked diseases or cancers where a characteristic antigen (which does not need to be a membrane protein) is expressed, such as in HPV and cervical carcinoma, HTLV-I-induced leukemias, prostate-specific antigen (PSA) and prostate cancer, mutated p53 and Colon carcinoma, GD2 antigen and melanoma. Example 1 describes procedures for constructing plasmids capable of generating retroviral vectors in packaging cells, which then lead to expression of HIV viral antigens.

EXAMPLE 1

Vectors Expressing HIV Antigens

A. Env Expression Vector (See FIG. 1)

A 2.7 kb Kpn-Xho I DNA fragment was isolated from the HIV proviral clone BH10-R3 (for sequence, see Ratner et al., *Nature* 313:277, 1985) and a ≈400 bp Sal-Kpn I DNA fragment from IIIexE7deltaenv (a Bal31 deletion to nt. 5496) was ligated into the Sal I site in the plasmid SK⁺. From this clone, a 3.1 kb env DNA fragment (Xho I-Cla I) which also encodes rev, essential for env expression, was purified and ligated into a retroviral vector called pAFVXM (see Kriegler et al., *Cell* 38:483, 1984). This vector was modified in that the Bgl II site was changed by linker insertion to a Xho I site to facilitate cloning of the HIV env coding DNA fragment.

A dominant selectable marker gene comprised of a SV40 early promoter driving expression of neomycin phosphotransferase gene was inserted into the vector at the Cla I site to facilitate isolation of infected and transfected cell lines. This vector is called pAF/Env'/SV$_2$neo (see FIG. 1).

The Xho I site upstream from the ENV gene in the vector provides a convenient site to insert additional promoters into the vector construct as the RSV promoter, SV40 early or late promoter, the CMV immediate early (IE) promoter, human beta-actin promoter, and Moloney murine MLV SL3-3 promoter.

Figure 2:
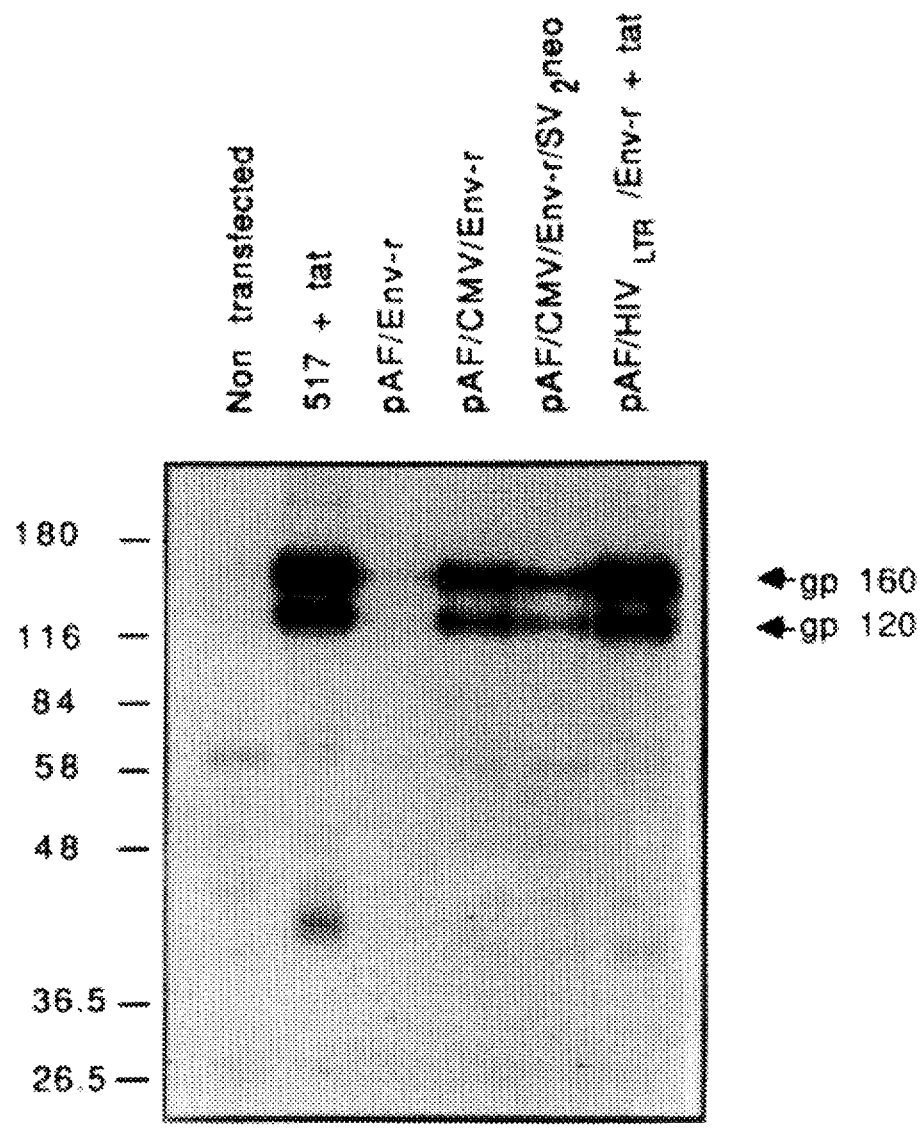
FIG. 2 illustrates the HIV env expression levels seen in polyacrylamide gel electrophoresis of HIV env-specific radioimmune precipitations of extracts of human Sup T1 cells transfected with the vectors shown. The markers are in kilodaltons. gp 160 and gp 120 mark the appropriate proteins, and 517+tat is the positive control (HIV LTR driving env in the presence of tat).

One such promoter, the CMV Immediate Early gene promoter (see FIG. 1), a 673 bp DNA fragment Hinc II to Eag I, results in a tenfold increase in ENV expression in a human T-cell line called Sup T1 when compared to the parental construct pAF/Env'/SV$_2$neo (see FIG. 2).

To improve titres of the vector one can use a recombinant retrovirus based on N2 (Armentano et al., *J. Virol.* 61:1647–1650, 1987; Eglitas et al., *Science* 230:1395–1398, 1985). This vector contains both the packaging sequences from N2 as well as the bacterial neomycin phosphotransferase gene. The above HIV env construct linked to the CMV promoter was inserted into the unique Xho I site in N2.

B. Gag Expression Vector

To efficiently express HIV gag and pol gene products in a retrovirus vector, two criteria must be met: 1) a REV response element must be added to the vector to override repressive elements buried in gag and pol; and 2) REV must be efficiently expressed to interact with the REV-responsive element inserted in the vector, thus allowing for correct transport of viral messenger RNA into the cytoplasm.

A 2.5 kb Sac I-Eco RV DNA fragment was isolated from pBH10-R3 (see Ratner et al., op. cit.) and ligated into the Sac I-Sma I site of pUC31 along with a linker coding for a universal translation termination codon. pUC31 is derived from pUC19 with additional Xho I, Bgl II, Bst II and Nco I sites inserted between the Eco R1 and Kpn I sites of the poly linker. However, this construct contained the major splice donor (SD) site from HIV and thus could be problematic in virus generation. The SD site was removed by subcloning a 70 bp Rsa I-Cla I fragment with a 2.1 kb Cla I-Bam HI DNA fragment into the Hinc II-Bam HI site of SK$^+$. The Bam HI site was converted into a Cla I site by linker insertion. This construct was designated SK$^+$ gag protease SD delta.

A gag/pol SD deletion complete construct was produced by a three-part ligation reaction in which a 757 bp Xho-Spe I fragment from SK$^+$ gag protease SD delta and a 4.3 kb Spe I-Nco I fragment from BH10 R3 were inserted into SK$^+$ XhoI-Nco I. The Xba I site in SK$^+$ was converted to a Nco I to facilitate this reaction.

In order to introduce both REV and the REV responsive elements in the vector, a 1.4 kb Ssp I deletion in the plasmid SK$^+$ HIV env was generated. This deletion removed intronic sequences which are not important for REV expression (REV expression will continue to be from a spliced mRNA.) In addition, this deletion does not effect the REV responsive element located in env. The 1.1 kb DNA fragment coding for the dominant selectable marker Neo, engineered to contain a eukaryotic translation initiation codon, was introduced into the construct at the Bgl II site in env. Insertion of neo facilitates detection of passaged virus as well as selection for virus in an unspliced state during passage. A promoter such as the CMV is inserted into the XhoI site of this construct. This construct is designated SK$^+$ CMV/REV/Neo. The final viral construct may be produced by a four-part ligation reaction. A 2.5 kb Xho I-Xba I DNA fragment from SK$^+$ gag polymerase SD delta, a 3.5 kb Spe I-Cla I DNA fragment from SK$^+$ CMV/REV/Neo and a 1.2 kb Cla I-Hind III DNA fragment from N2R3(–) (a subclone of N2 containing only the 3' LTR) are inserted into pUC N2R5 (a subclone of N$_2$ containing the 5' LTR) at the Xho I-Hind III site of this construct.

These plasmids, when placed in a suitable packaging cell, expressed a retroviral vector construct which contains a packaging signal. The packaging signal directed packaging of the vector construct into a capsid and envelope along with all further proteins required for viable retroviral particles. The capsid, envelope, and other proteins are preferably produced from one or more plasmids containing suitable genomes placed in the packaging cell. Such genomes may be proviral constructs, which in a simple case may merely have the packaging signal deleted. As a result, only the vector will be packaged. Suitable packaging or packaging cell lines, and the genome necessary for accomplishing such packaging, are described in Miller et al. (*Mol. Cell. Bio.* 6:2895, 1986), which is incorporated herein by reference. As described by Miller et al., it is preferable that further changes be made to the proviral construct other than simple deletion of the packaging signal in order to reduce the chances of recombination events occurring within the packaging cell line, which may result in production of viral particles which are not replication defective.

It will be understood that Example 1 is merely illustrative of a procedure for generating an HIV envelope glycoprotein (gp) or other viral antigen. It is also possible to provide a proviral vector construct which expresses a modified HIV envelope gp on the target cells which will likewise stimulate an immune response, but with less T-cell cytopathic effects. Envelope glycoproteins can be suitably modified using techniques well known in the art, for instance through use of the disclosure of articles such as Kowalski et al. (*Science* 237:1351, 1987), which is herein incorporated by reference. Thus, a proviral construct may be constructed by the above technique which generates retroviral constructs expressing such a suitably modified gp. This construct is then placed in a packaging cell as described above. The resulting recombinant retroviruses produced from the packaging cell lines may be used in vitro and in vivo to stimulate an immune response through the infection of susceptible target cells. It will be appreciated that other proteins expressed from the HIV genome, such as gag, pol, vif, nef, etc., may also elicit beneficial cellular responses in HIV-infected individuals. Proviral vectors such as those described below are designed to express such proteins so as to encourage a clinically beneficial immune response. It may be necessary for certain vectors to include rev coding sequences as well as a rev responsive element (Rosen et al., *Proc. Natl. Acad. Sci.* 85:2071, 1988).

The following example demonstrates the ability of this type of treatment to elicit CTL responses in mice.

EXAMPLE 2

Immune Response to Retroviral Vector-Encoded Antigens

Figure 3:
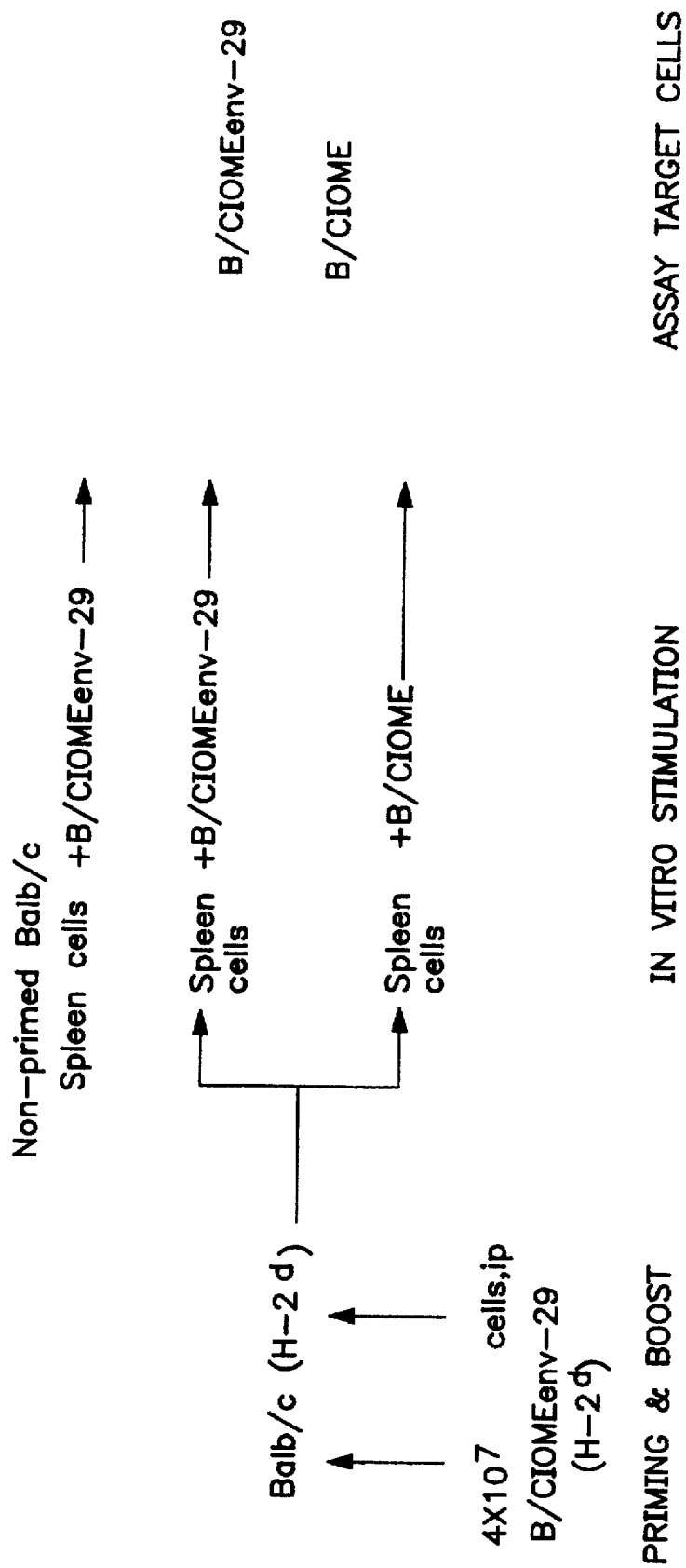
FIG. 3 depicts the protocol for testing T-cell killing induced in mice injected with syngeneic tumor cells expressing HIV env (the vector is pAF/Env$^r$/SV$_2$neo).

A murine tumor cell line (B/C10ME) (H-2$^d$) was infected with a recombinant retrovirus carrying the pAF/Env'/SV$_2$neo vector construct coding for HIV env. One cloned HIV-env expressing cell line (B/C10ME-29) was then utilized to stimulate HIV-env-specific CTL in syngeneic (i.e., MHC identical) Balb/c (H-2$^d$) mice (see FIG. 3). Mice were immunized by intraperitoneal injection with B/C10ME-29 cells (1×10$^7$ cells) and boosted on day 7–14. Responder spleen cell suspensions were prepared from these immunized mice and the cells cultured in vitro for 4 days in the presence of either B/C10ME-29 (BCenv) or B/C10ME (BC) mitomycin-C-treated cells at a stimulator:responder cell ratio of 1:50 (FIG. 3). The effector cells were harvested from these cultures, counted, and mixed with radiolabeled ($^{51}$Cr)

target cells (i.e., B/C10MEenv-29 or B/C10ME) at various effector:target (E:T) cell ratios in a standard 4–5 hr $^{51}$Cr-release assay. Following incubation, the microtiter plates were centrifuged, 100 ul of culture supernate was removed, and the amount of radiolabel released from lysed cells quantitated in a Beckman gamma spectrometer. Target cell lysis was calculated as: % Target Lysis=Exp CPM–SR CPM/MR CPM–SR CPM×100, where experimental counts per minute (Exp CPM) represents effectors plus targets; spontaneous release (SR) CPM represents targets alone; and maximum release (MR) CPM represents targets in the presence of 1M HCl.

The results (FIG. 4A) illustrate that CTL effectors were induced which specifically lysed HIV-env-expressing target cells (BCenv) significantly more efficiently than non-HIV env BC targets. Primed spleen cells restimulated in vitro with non-HIV-env-expressing control cells (B/C10ME) did not show significant CTL activity on either B/C10MEenv-29 or B/C10ME targets, particularly at lower E:T cell ratios. Spleen cells obtained from naive nonimmunized Balb/c mice which were stimulated in vitro with B/C10MEenv-29 did not generate CTL (data not shown), thus suggesting the importance of the in vivo priming and boosting event. This experiment has been repeated and similar results obtained.

In another experiment, effector cells obtained from Balb/c mice immunized, boosted and restimulated in vitro with a different H-2$^d$ HIV-env-expressing tumor cell clone (L33-41) infected with the same pAF/Env'/SV$_2$neo (HIV-env) vector construct were capable of lysing B/C10MEenv-29 target cells. This provides additional support that the CTL generated in these mice are specifically recognizing an expressed form of HIV-env rather than simply a unique tumor cell antigen on these cells. This result also suggests that the vector-delivered antigen is presented in a similar manner by the two tumor cell lines. The specificity of the CTL response was further demonstrated by testing effector cells obtained from BCenv immunized mice on BCenv target cells expressing the neo and HIV env genes, BC (non-neo, non-HIV env) parental targets and BCneo target cells expressing the neo resistance marker gene, but no HIV env. FIG. 4B indicates that the CTL responses are specific for the HIV env protein.

In another experiment, effector cells obtained from mice immunized with 1×10$^7$ BCenv cells, boosted and restimulated in vitro, were treated with T-cell-specific monoclonal antibodies (Mab) plus complement (C') in order to determine the phenotype of the induced cytotoxic effector cells. Effectors were treated with either anti-Thy 1.2 (CD3), anti-L3T4 (CD4) or anti-Lyt 2.2 (CD8) Mab for 30 minutes at 4° C., washed 1 time in Hank's balanced salt solution (HBSS), resuspended in low tox rabbit C' and incubated 30 minutes at 37° C. The treated cells were washed 3 times in RPMI 1640 complete medium, counted, and tested for their ability to lyse BCenv radio-labeled target cells as previously described. FIG. 4C shows that treatment with either anti-Thy 1.2 or anti-Lyt 2.2 Mab+C' abrogated cytotoxic activity, whereas treatment with anti-L3T4 Mab+C' or C' alone did not significantly affect cytotoxicity. These results indicate that the majority population of cytotoxic effector cells generated in this system are of the CD3$^+$ CD4$^-$ CD8$^+$ cytotoxic T-cell phenotype.

Experiments were performed to determine the MHC restriction of CTL effector cells described above. Polyclonal antibodies directed against different H-2 regions of the murine MHC (i.e., anti-H-2$^d$, anti-H-2D$^d$, anti-H-2L$^d$, anti-H-2K$^d$, anti-H-2I$^d$) were used to inhibit the CTL response on BCenv target cells. The anti-H-2$^k$ antiserum was used as a negative control. The data (FIG. 4D) indicate that the Balb/c anti-BCenv CTL response is inhibited primarily by the anti-H-2D$^d$ antiserum. This suggests that these CTL responses are restricted by MHC class I molecules, most likely encoded within the D region of the H-2 complex.

In addition to experiments in which mice were immunized with replication-competent HIV env-expressing tumor cells, tests were conducted to determine whether proliferating stimulator cells were necessary for inducing CTL in vivo. Mice were immunized with either irradiated (10,000 rads) or nonirradiated BCenv cells, and the primed spleen cells were later stimulated in vitro, as previously described. The resulting effector cells were tested for CTL activity on radiolabeled BCenv and BC target cells. FIG. 4E indicates HIV-specific CTL can be induced in vivo with either irradiated or nonirradiated stimulator cells. These data demonstrate that CTL induction by HIV env-expressing stimulator cells is not dependent upon proliferation of stimulator cells in vivo and that the presentation of HIV env antigen in the appropriate MHC context is sufficient for effective CTL induction. Formalin fixed cells also elicit an equivalent immune response. This shows that killed cells or perhaps cell membranes expressing the appropriate antigen in the proper MHC class I/II molecular context are sufficient for induction of effective CTL responses.

Additional experiments were performed to examine the optimal injection dose of BCenv cells into Balb/c mice. Mice were immunized with varying numbers of BCenv stimulator cells, restimulated in vitro as described, and tested for CTL activity. The results shown in FIG. 4F indicate that immunization of mice with 5×10$^6$ env-expressing BCenv-29 stimulator cells generated an optimal CTL response under these conditions.

Further experiments examined the ability of vector-infected HIV env-expressing BCenv stimulator cells to induce CTL responses in other H-2$^d$ mouse strains other than Balb/c, in order to provide an indication as to genetic restrictions imposed on host responsiveness. Different strains of H-2$^d$ (i.e., Balb/c, DBA/2, B10.D2), as well as H-2$^d$×H-2$^b$ F1 hybrid mice [i.e., CB6F1 (Balb/c×B6 F1); B6D2F1 (B6×DBA/2 F1)], were immunized with BCenv stimulator cells and examined for the induction of CTL responses. FIG. 4G illustrates that all strains including F1 hybrids generate CTL responses against the BCenv target cells to varying degrees. Although some strains also exhibit responses against the parental (i.e., non-HIV env) target cells, these responses are lower than those directed against the BCenv target.

Implementation of this immunostimulant application in humans requires that (1) the gene coding for the antigen of interest be delivered to cells, (2) the antigen be expressed in appropriate cells, and (3) MHC restriction requirements, i.e., class I and class II antigen interaction, are satisfied. Within a preferred embodiment, preparations of vector are made by growing the producer cells in normal medium, washing the cells with PBS plus human serum albumin (HSA) at 10 mg/ml, then growing the cells for 8–16 hours in PBS plus HSA. Titres obtained are typically 10$^4$ to 10$^6$/ml depending on the vector, packaging line or particular producer line clone. The vector supernatants are filtered to remove cells and are concentrated up to 100-fold by filtration through 100,000 or 300,000 pass Amicon filters (Wolff et al., *Proc. Natl. Acad. Sci.* 84:3344, 1987). This lets globular proteins of 100,000 or 300,000 pass but retains 99% of the viral vector as infectious particles. The stocks can be frozen for storage since they lose about 50% of the infectious units on freezing and thawing. The most direct delivery involves administration of the appropriate gene-carrying vector into the individual and reliance upon the ability of the vector to efficiently target to the appropriate cells, which can then initiate stimulation of the immune response. The dose is generally $10^5$ to $10^6$ infectious units/kg body weight. However, a more practical approach may involve the extracorporeal treatment of patient peripheral blood lymphocytes (PBL), fibroblasts or other cells obtained from each individual with the vector. PBL can be maintained in culture through the use of mitogens (phytohemagglutinin) or lymphokines (e.g., IL-2). This type of approach allows for directed vector infection, monitoring of expression and expansion of the antigen presenting cell population prior to injection, and return, of vector-expressing cells to the respective patient. Other types of cells can also be explanted, a vector introduced, and the cells returned to the patient. Only a moderate number of infected cells ($10^5$–$10^7$) is necessary to elicit strong immune responses in mice. It is probable that the dose to elicit an immune response is roughly the same per individual animal or patient with very little dependence on body size.

Within one alternative method, cells are infected ex vivo as described above, and either inactivated by irradiation (see FIG. 4E) or killed by fixation, such as by formalin. Formalin fixation of cells treated with a vector expressing HIV env after treatment with the vector carrying the HIV env gene induces a strong CTL response.

Within another alternative method, stimulator cell membrane fragments which contain both the antigen of interest and the appropriate MHC molecule as a complex are employed. Cells are infected with vector, genes expressed, cells disrupted and the membranes purified by centrifugation or affinity columns specific for the MHC-antigen complex. This process provides greater quality control from a manufacturing and stability standpoint.

This approach also allows the use of cells that normally do not express human MHC molecules (e.g., human cell mutants, mouse cells). Individual MHC class I or class II genes are infected into MHC-cells to give expression of the individual corresponding MHC protein, in a particular cell line. Thus, a bank of cell lines capable of displaying antigens in the context of different MHC classes is generated. A small number of these (10–20) will cover (i.e., have a match with) the majority of the human population. For example, HLA A2 is present in about 30–60% of individuals. In the case of non-human cells, those can be derived from transgenic animals such as mice) which express human MHC molecules generally or in specific tissues due to the presence of a transgene in the strain of animals (see, e.g., Chamberlin et al., Proc. Natl. Acad. Sci. USA 85: 7690–7694, 1988).

In any of the above situations, the presentation or response to the presentation can be enhanced by also infecting into the cells genes of other proteins involved in the immune interactions which are missing or underrepresented (e.g., β microglobulin, LFA3, CD3, ICAM-I and others). β microglobulin is a nonvariant, necessary subunit of the class I MHC, CD3 is involved in the MHC interaction, and LFA3 and ICAM-I molecules enhance the interaction of cells of the immune system (see, e.g., Altmann et al., Nature 338:512, 1989) leading to stronger responses to the same level of immune stimulation.

In the case of transgenic mice expressing human MHC, the stimulation could also be performed in the mouse using somatic transgenic mouse cells expressing a foreign antigen, the gene for which was introduced by a viral vector or other means, as stimulators. The mouse CTL thus generated would have T-cell receptors expressing in the context of the human MHC, and could be used for passive cellular immunization or treatment (i.e., infused into patients) of patients.

As a further alternative, one can use cells from a patient and boost expression of "self" MHC class I genes by introducing the matched MHC gene by vector transfer or other means. Such a boost in MHC I expression causes more efficient presentation of foreign antigens, whether they are present already in the patient's cells (e.g., tumor cells) or subsequently added using viral vectors encoding foreign antigens. This, in turn, leads to a more potent immune response when even cells with reduced MHC I expression (such as some virally infected cells or some tumor types) are efficiently eliminated. Within certain aspects of the present invention, one can infect susceptible target cells with a combination or permutation of nucleic acid sequences encoding (a) individual Class I or Class II MHC protein, or combinations thereof; (b) specific antigens or modified forms thereof capable of stimulating an immune response; and (c) other proteins involved in the immune interactions which are missing or underrepresented, as discussed above. The respective steps of infection may be performed in vivo or ex vivo.

A different form of administration is the implantation of producer lines making retroviral vector particles. These may be immunologically unmatched classical producer cell lines or the patients own cells, which have been explanted, treated and returned (see VI Alternative Viral Vector Packaging Techniques, below). Both types of implants ($10^5$–$10^6$ cells/kg body weight) would have a limited life span in the patient, but would lead to the retroviral vector infecting large numbers ($10^7$–$10^{10}$) of cells in their vicinity in the body.

In any case, the success of the HIV immune stimulating treatment can be assayed by removing a small amount of blood and measuring the CTL response using as targets the individual's own cells infected with vector leading to env expression.

When it is desired to stimulate an MHC class I or class II restricted immune response to pathogens, including pathogenic viruses other than HIV, suitable forms of envelope or other antigens associated with such retroviruses which will stimulate an immune response can be ascertained by those skilled in the art. In general, there will be combinations of epitopes which cause induction of various parts of the immune system (e.g., $T_H$, $T_C$, B-cells). In addition, some epitopes may be pathogenic or hypervariable but immunodominant. The present invention allows a "mix-and-match" selection of combinations of desirable epitopes and exclusion of undesirable epitopes. For example, in HIV, a number of hypervariable loops which carry immunodominant B- and T-cell epitopes can be strung together in the gene sequence carried by the vector so that the resultant immunostimulation is appropriate for the preponderance of HIV strains found clinically.

An alternative approach to creating a desired immune response is to deliver an antigen-specific T-cell receptor gene to an appropriate cell, such as a T-cell. It is also possible to molecularly graft the genetic message for antigen recognition sites of immunoglobulin molecules into the corresponding sites in the genes of the related T-cell receptor subunits α and β. Such altered protein molecules will not be MHC restricted, and will be able to perform as $T_H$- and $T_C$-cells specific for the antigen defined by the original immunoglobulin. Another tactic is to transfer genes for effector molecules in NK into NK cells to confer additional non-MHC limited killing capability on these cells. In addition, specific immunoglobulin genes could similarly be useful when delivered to B-cells to cause the large-scale in vivo production of a particular antibody molecule in a patient.

II. Blocking Agents

Many infectious diseases, cancers, autoimmune diseases, and other diseases involve the interaction of viral particles with cells, cells with cells, or cells with factors. In viral infections, viruses commonly enter cells via receptors on the surface of susceptible cells. In cancers, cells may respond inappropriately or not at all to signals from other cells or factors. In autoimmune disease, there is inappropriate recognition of "self" markers. Within the present invention, such interactions may be blocked by producing, in vivo, an analogue to either of the partners in an interaction.

This blocking action may occur intracellularly, on the cell membrane, or extracellularly. The blocking action of a viral or, in particular, a retroviral vector carrying a gene for a blocking agent, can be mediated either from inside a susceptible cell or by secreting a version of the blocking protein to locally block the pathogenic interaction.

In the case of HIV, the two agents of interaction are the gp 120/gp 41 envelope protein and the CD4 receptor molecule. Thus, an appropriate blocker would be a vector construct expressing either an HIV env analogue that blocks HIV entry without causing pathogenic effects, or a CD4 receptor analogue. The CD4 analogue would be secreted and would function to protect neighboring cells, while the gp 120/gp 41 is secreted or produced only intracellularly so as to protect only the vector-containing cell. It may be advantageous to add human immunoglobulin heavy chains or other components to CD4 in order to enhance stability or complement lysis. Delivery of a retroviral vector encoding such a hybrid-soluble CD4 to a host results in a continuous supply of a stable hybrid molecule.

Figure 5:
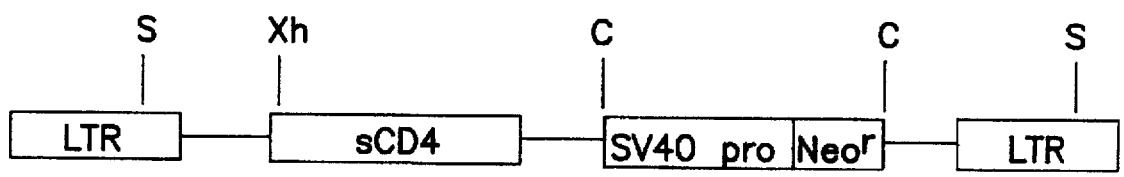
FIG. 5 depicts a vector designed to express sCD4.

Vector particles leading to expression of HIV env may also be constructed as described above. It will be evident to one skilled in the art which portions are capable of blocking virus adsorption without overt pathogenic side effects (Willey et al., *J. Virol.* 62:139, 1988; Fisher et al., *Science* 233:655, 1986). The following example describes the construction of a CD4 vector from which infectious vector particles were made (FIG. 5).

EXAMPLE 3 sCD4 Vector

1. A 1.7 kb Eco R1—Hind III DNA fragment from pMV7.T4 (Maddon et al., *Cell* 47:333, 1986) was blunt-end ligated to the Hinc II site of Sk⁺.

2. A universal translation termination sequence containing an Xba I site was inserted into the Nhe I site of the CD4 fragment.

3. The 1.7 kb Xho I—Cla I fragment was excised and cloned into the Xho I—Cla I site of pAFVXM. These vector plasmids can be used to generate infectious vector particles, as described in Example 1.

Such infectious blocking vectors, when put into human T-cell lines in culture, can inhibit the spread of HIV infections. Preparation, concentration and storage of infectious retroviral vector preparations is as for the immunostimulant. Route of administration would also be the same, with doses about tenfold higher. Another route which may be used is the aspiration of bone marrow, infection with retroviral vector and return of this infected marrow (Gruber et al., *Science* 230:1057, 1985) to the patient. Since the marrow replication will amplify the vector expression through cell replication, doses in the range of the immunostimulant can be used ($10^5$–$10^6$/kg body weight).

In any case, the efficacy of the treatment can be assayed by measuring the usual indicators of disease progression, including antibody level, viral antigen production, infectious HIV levels, or levels of nonspecific infections.

III. Expression of Palliatives

Techniques similar to those described above can be used to produce recombinant retroviruses with vector constructs which direct the expression of an agent (or "palliative") which is capable of inhibiting a function of a pathogenic agent or gene. Within the present invention, "capable of inhibiting a function" means that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for a cancerous cell or cancer-promoting growth factor include viability, cell replication, altered susceptibility to external signals (e.g., contact inhibition), and lack of production or production of mutated forms of anti-oncogene proteins.

(i) Inhibitor Palliatives

In one aspect of the present invention, the recombinant retrovirus carries a vector construct which directs the expression of a gene which can interfere with a function of a pathogenic agent, for instance in viral or malignant diseases. Such expression may either be essentially continuous or in response to the presence in the cell of another agent associated either with the pathogenic condition or with a specific cell type (an "identifying agent"). In addition, vector delivery may be controlled by targeting vector entry specifically to the desired cell type (for instance, a virally infected or malignant cell) as discussed below.

A preferred method of administration is leukophoresis, in which about 20% of an individual's PBLs are removed at any one time and manipulated in vitro. Thus, approximately $2 \times 10^9$ cells may be treated and replaced. Since the current maximum titres are around $10^6$/ml, this requires 2 to 20 liters of starting viral supernatant. Repeat treatments also would be performed. Alternatively, bone marrow may be treated and allowed to amplify the effect as described above.

In addition, packaging cell lines producing a vector may be directly injected into a subject, allowing continuous production of recombinant virions. Examples of suitable cell types include monocytes, neutrophils, or their progenitors, since these cells are present in the peripheral blood but can also leave the circulatory system to allow virus production in extravascular tissue (particularly the central nervous system) where virion production may be therapeutically required. Such a cell line would ultimately be rejected as foreign by the host immune system. To ensure the eventual destruction of these foreign cells from the host (even an immuno-suppressed host) the cell line may be engineered to express the gene for a conditionally lethal protein, such as HSVTK. Thus, administration of the drug Acyclovir (ACV) (a drug which is specifically toxic for cells expressing HSVTK) eliminates these cells after sufficient vector has been produced in vivo. Such a packaging cell line could be a continuous cell line or could be made directly from host cells.

Figure 10:
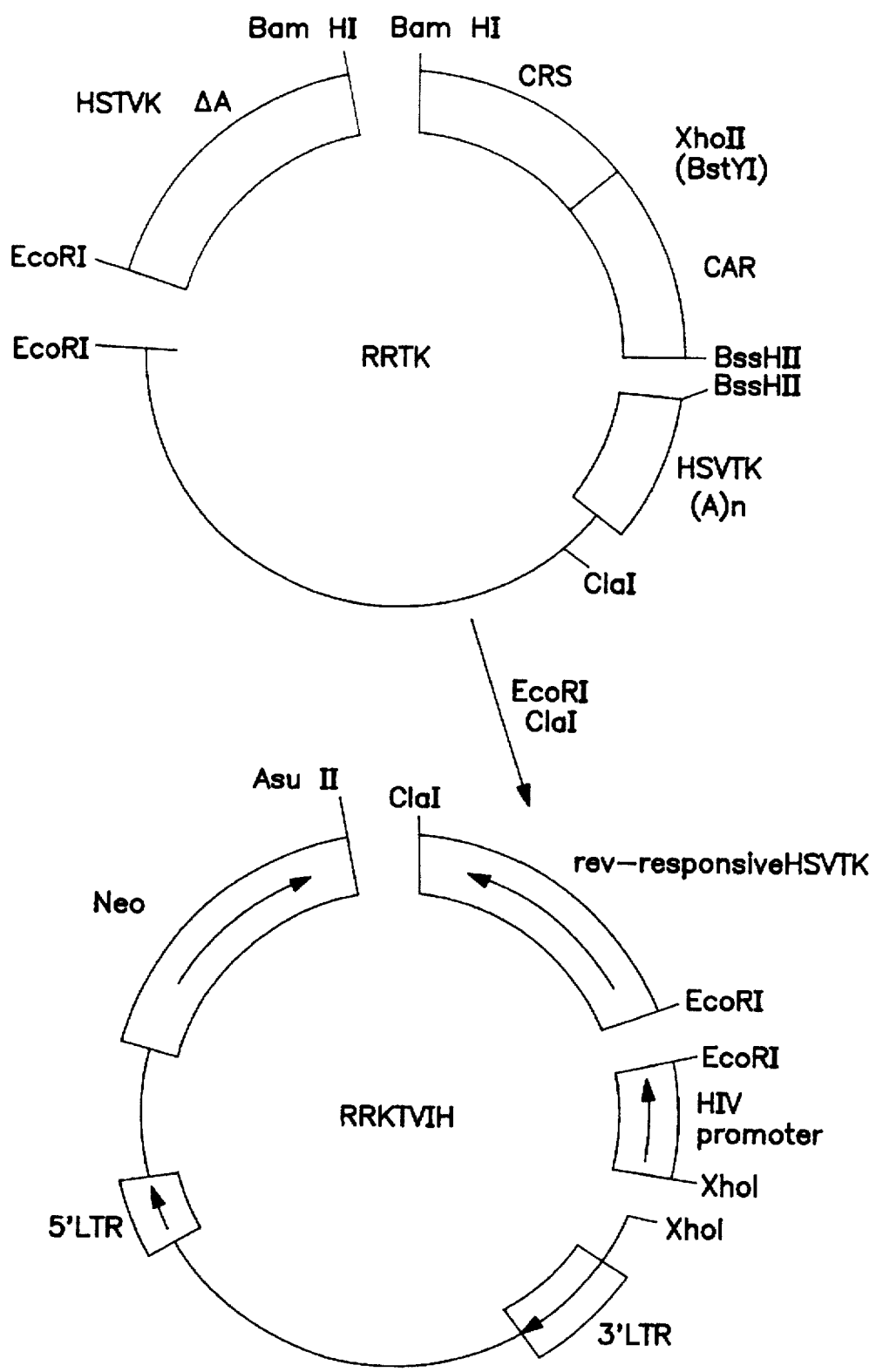
FIG. 10 illustrates the construction of the plasmid carrying the vector RRKTVIH.

In one embodiment, retroviral viruses which express RNA complementary to key pathogenic gene transcripts (for example, a viral gene product or an activated cellular oncogene) can be used to inhibit translation of that transcript into protein, such as the inhibition of translation of the HIV tat protein. Since expression of this protein is essential for viral replication, cells containing the vector would be resistant to HIV replication. To test this, the vector αtat (FIG. 10) has been constructed, packaged as recombinant virions and introduced into human T-cells and monocyte cell lines in the absence of replication-competent helper virus.

In a second embodiment, where the pathogenic agent is a single-stranded virus having a packaging signal, RNA complementary to the viral packaging signal (e.g., an HIV packaging signal when the palliative is directed against HIV) is expressed, so that the association of these molecules with the viral packaging signal will, in the case of retroviruses, inhibit stem loop formation or tRNA primer binding required for proper encapsidation or replication of the retroviral RNA genome.

In a third embodiment, a retroviral vector may be introduced which expresses a palliative capable of selectively inhibiting the expression of a pathogenic gene, or a palliative capable of inhibiting the activity of a protein produced by the pathogenic agent. In the case of HIV, one example is a mutant tat protein which lacks the ability to transactivate expression from the HIV LTR and interferes (in a trans-dominant manner) with the normal functioning of tat protein. Such a mutant has been identified for HTLV II tat protein ("XII Leu$^5$" mutant; see Wachsman et al., *Science* 235:674, 1987). A mutant transrepressor tat should inhibit replication much as has been shown for an analogous mutant repressor in HSV-1 (Friedmann et al., *Nature* 335:452, 1988).

Such a transcriptional repressor protein may be selected for in tissue culture using any viral-specific transcriptional promoter whose expression is stimulated by a virus-specific transactivating protein (as described above). In the specific case of HIV, a cell line expressing HIV tat protein and the HSVTK gene driven by the HIV promoter will die in the presence of ACV. However, if a series of mutated tat genes are introduced to the system, a mutant with the appropriate properties (i.e., represses transcription from the HIV promoter in the presence of wild-type tat) will grow and be selected. The mutant gene can then be reisolated from these cells. A cell line containing multiple copies of the conditionally lethal vector/tat system may be used to assure that surviving cell clones are not caused by endogenous mutations in these genes. A battery of randomly mutagenized tat genes are then introduced into these cells using a "rescuable" retroviral vector (i.e., one that expresses the mutant tat protein and contains a bacterial origin of replication and drug resistance marker for growth and selection in bacteria). This allows a large number of random mutations to be evaluated and permits facile subsequent molecular cloning of the desired mutant cell line. This procedure may be used to identify and utilize mutations in a variety of viral transcriptional activator/viral promoter systems for potential antiviral therapies.

In a fourth embodiment, the recombinant retrovirus carries a vector construct that directs the expression of a gene product capable of activating an otherwise inactive precursor into an active inhibitor of the pathogenic agent. For example, the HSVTK gene product may be used to more effectively metabolize potentially antiviral nucleoside analogues, such as AZT or ddC. The HSVTK gene may be expressed under the control of a constitutive macrophage or T-cell-specific promoter and introduced into these cell types. AZT (and other nucleoside antivirals) must be metabolized by cellular mechanisms to the nucleotide triphosphate form in order to specifically inhibit retroviral reverse transcriptase and thus HIV replication (Furmam et al., *Proc. Natl. Acad. Sci. USA* 83:8333–8337, 1986). Constitutive expression of HSVTK (a nucleoside and nucleoside kinase with very broad substrate specificity) results in more effective metabolism of these drugs to their biologically active nucleotide triphosphate form. AZT or ddC therapy will thereby be more effective, allowing lower doses, less generalized toxicity, and higher potency against productive infection. Additional nucleoside analogues whose nucleotide triphosphate forms show selectivity for retroviral reverse transcriptase but, as a result of the substrate specificity of cellular nucleoside and nucleotide kinases are not phosphorylated, will be made more efficacious. A description of a representative method is set forth in Example 4.

EXAMPLE 4

Vectors Designed to Potentiate the Antiviral Effect of AZT and Analogues

A. All of the following retroviral vectors are based on the "N2" vector (see Keller et al., *Nature* 318:149–154, 1985). Consequently, 5' and 3' Eco R1 LTR fragments (2.8 and 1.0 kb, respectively) were initially subcloned into plasmids containing polylinkers (into SK+ to give pN2R5[±]; into pUC31 to give p31N2R5[±] and p31N2R3[±] to facilitate vector construction. pUC31 is a modification of pUC19 carrying additional restriction sites (Xho I, Bgl II, BssH II, and Nco I) between the Eco R1 and Sac I sites of the polylinker. In one case, a 1.2 kb Cla I/Eco R1 5' LTR fragment was subcloned into the same sites of an SK$^+$ vector to give pN2CR5. In another case, the 5' LTR containing a 6 bp deletion of the splice donor sequence was subcloned as a 1.8 kb Eco R1 fragment into pUC31 (p31N25delta[+]). The coding region and transcriptional termination signals of HSV-1 thymidine kinase gene were isolated as a 1.8 kb Bgl II/Pvu II fragment from plasmid 322TK (3.5 kb Bam HI fragment of HSVTK cloned into Bam HI of pBR322) and cloned into Bgl II/Sma I-digested pUC31 (pUCTK). For constructs which require deletion of the terminator signals, pUCTK was digested with Sma I and Bam HI. The remaining coding sequences and sticky-end Bam HI overhang were reconstituted with a double-stranded oligonucleotide made from the following oligomers:

5' GAG AGA TGG GGG AGG CTA ACT GAG 3' and 5' GAT CCT CAG TTA GCC TCC CCC ATC TCT C 3' forming the construct pTK delta A.

For diagnostic purposes, the oligos were designed to destroy the Sma I site while keeping its Ava I site without changing the translated protein.

The 0.6 kb HIV promoter sequences were cloned as a Dra I/Hind III fragment from pCV-1 (see Arya et al., *Science* 229:69–73, 1985) into Hinc II/Hind III-cut SK$^+$ (SKHL).

Figure 6:
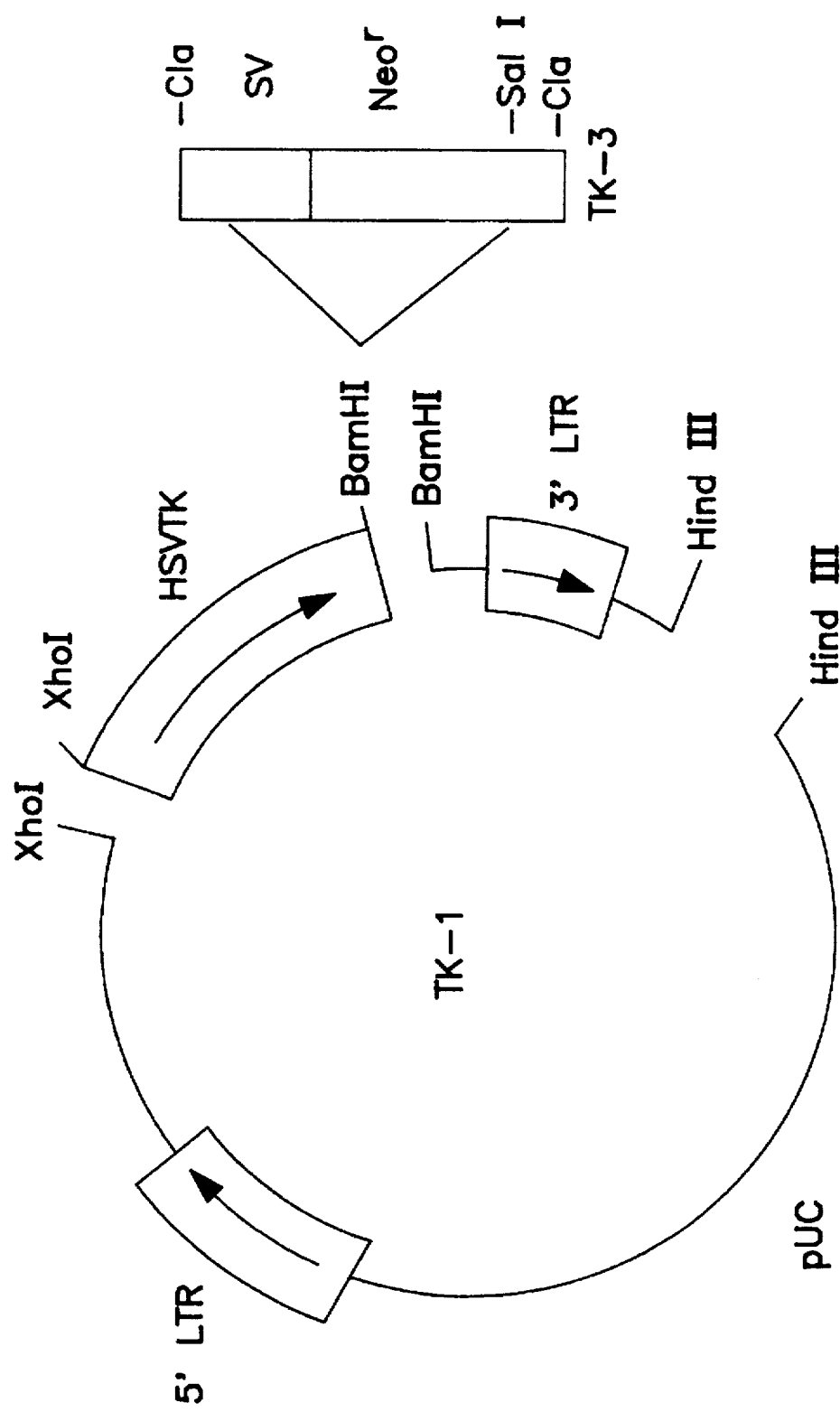
FIG. 6 illustrates the construction of the plasmids carrying the vectors TK1 (without SV-Neo) and TK3 (plus SV-Neo).

B. Construction of TK-1 and TK-3 retroviral vectors (see FIG. 6)

1. The 5 kb Xho I/Hind III 5' LTR and plasmid sequences were isolated from p31N2R5(+).

2. HSVTK coding sequences lacking transcriptional termination sequences were isolated as a 1.2 kb Xho I/Bam HI fragment from pTKdeltaA.

3. 3' LTR sequences were isolated as a 1.0 kb Bam HI/Hind III fragment from pN2R3(–).

4. The fragments from steps 1–3 were mixed, ligated, transformed into bacteria, and individual clones identified by restriction enzyme analysis (TK-1).

5. TK-3 was constructed by linearizing TK-1 with Bam HI, filling in the 5' overhang and blunt-end ligating a 5'-filled Cla I fragment containing the bacterial lac UV5 promoter, SV40 early promoter, plus Tn5 Neo' gene. Kanamycin-resistant clones were isolated and individual clones were screened for the proper orientation by restriction enzyme analysis.

These constructs were used to generate infectious recombinant vector particles in conjunction with a packaging cell line, such as PA317, as described above.

Administration of these retroviral vectors to human T-cell and macrophage/monocyte cell lines can increase their resistance to HIV in the presence of AZT and ddC compared to the same cells without retroviral vector treatment. Treatment with AZT would be at lower than normal levels to avoid toxic side effects, but still efficiently inhibit the spread of HIV. The course of treatment would be as described for the blocker.

Preparation, concentration and storage of the retroviral vector preparations would be as described above. Treatment would be as previously described but ex corpore treatment of patients' cells would aim for uninfected potentially susceptible T-cells or monocytes. One preferred method of targeting the susceptible cell is with vectors which carry HIV env or hybrid env (see Section VIII Cell Line Specific Retroviruses, below) to direct absorption of vector particles to $CD4^+$ cells. Normal adults have about $5\times10^9$ T4 cells in their total blood and about the same number of monocytes.

A fifth embodiment for producing inhibitor palliatives involves the delivery and expression of defective interfering viral structural proteins, which inhibit viral assembly. Vectors would code for defective gag, pol, env or other viral particle proteins or peptides, and these would inhibit in a dominant fashion the assembly of viral particles. This occurs because the interaction of normal subunits of the viral particle is disturbed by interaction with the defective subunits.

A sixth such embodiment involves the expression of inhibiting peptides or proteins specific for viral protease. Viral protease cleaves the viral gag and gag/pol proteins into a number of smaller peptides. Failure of this cleavage in all cases leads to complete inhibition of production of infectious retroviral particles. The HIV protease is known to be an aspartyl protease, and these are known to be inhibited by peptides made from amino acids from protein or analogues. Vectors to inhibit HIV will express one or multiple fused copies of such peptide inhibitors.

A seventh embodiment involves the delivery of suppressor genes which, when deleted, mutated or not expressed in a cell type, lead to tumorigenesis in that cell type. Reintroduction of the deleted gene by means of a viral vector leads to regression of the tumor phenotype in these cells. Examples of such cancers are retinoblastoma and Wilms Tumor. Since malignancy can be considered to be an inhibition of cellular terminal differentiation compared with cell growth, the retroviral delivery and expression of gene products which lead to differentiation of a tumor should also, in general, lead to regression.

In an eighth embodiment, the retroviral construct (with or without the expression of a palliative) provides a therapeutic effect by inserting itself into a virus, oncogene, or pathogenic gene, thereby inhibiting a function required for pathogenesis. This embodiment requires the direction of retroviral integration to a specific site in the genome by homologous recombination, integrase modification, or other methods (described below).

In a ninth embodiment, the retroviral vector provides a therapeutic effect by encoding a ribozyme (an RNA enzyme) (Haseloff and Gerlach, *Nature* 334:585, 1989) which will cleave and hence inactivate RNA molecules corresponding to a pathogenic function. Since ribozymes function by recognizing a specific sequence in the target RNA and this sequence is normally 12 to 17 bp, this allows specific recognition of a particular RNA species such as a RNA or a retroviral genome. Additional specificity may be achieved in some cases by making this a conditional toxic palliative (see below).

One way of increasing the effectiveness of inhibitory palliatives is to express viral inhibitory genes in conjunction with the expression of genes which increase the probability of infection of the resistant cell by the virus in question. The result is a nonproductive "dead-end" event which would compete for productive infection events. In the specific case of HIV, vectors may be delivered which inhibit HIV replication (by expressing anti-sense tat, etc., as described above) and also overexpress proteins required for infection, such as CD4. In this way, a relatively small number of vector-infected HIV-resistant cells act as a "sink" or "magnet" for multiple nonproductive fusion events with free virus or virally infected cells.

(ii) Conditional Toxic Palliatives

Another approach for inhibiting a pathogenic agent is to express a palliative which is toxic for the cell expressing the pathogenic condition. In this case, expression of the palliative from the proviral vector should be limited by the presence of an entity associated with the pathogenic agent, such as an intracellular signal identifying the pathogenic state in order to avoid destruction of nonpathogenic cells. This cell-type specificity may also be conferred at the level of infection by targeting recombinant retrovirus carrying the vector to cells having or being susceptible to the pathogenic condition.

In one embodiment of this method, a recombinant retrovirus (preferably, but not necessarily, a recombinant MLV retrovirus) carries a vector construct containing a cytotoxic gene (such as ricin) expressed from an event-specific promoter, such as a cell cycle-dependent promoter (e.g., human cellular thymidine kinase or transfertin receptor promoters), which will be transcriptionally active only in rapidly proliferating cells, such as tumors. In this manner, rapidly replicating cells, which contain factors capable of activating transcription from these promoters, are preferentially destroyed by the cytotoxic agent produced by the proviral construct.

In a second embodiment, the gene producing the cytotoxic agent is under control of a tissue-specific promoter, where the tissue specificity corresponds to the origin of the tumor. Since the viral vector preferentially integrates into the genome of replicating cells (for example, normal liver cells are not replicating, while those of a hepatocarcinoma are), these two levels of specificity (viral integration/replication and tissue-specific transcriptional regulation) lead to preferential killing of tumor cells. Additionally, event-specific and tissue-specific promoter elements may be artificially combined such that the cytotoxic gene product is expressed only in cell types satisfying both criteria (e.g., in the example above, combined promoter elements. are functional only in rapidly dividing liver cells). Transcriptional control elements may also be amplified to increase the stringency of cell-type specificity.

These transcriptional promoter/enhancer elements need not necessarily be present as an internal promoter (lying between the viral LTRs) but may be added to or replace the transcriptional control elements in the viral LTRs which are themselves transcriptional promoters, such that condition-specific transcriptional expression will occur directly from the modified viral LTR. In this case, either the condition for maximal expression will need to be mimicked in retroviral packaging cell lines (e.g., by altering growth conditions, supplying necessary transregulators of expression or using the appropriate cell line as a parent for a packaging line), or the LTR modification is limited to the 3' LTR U3 region, to obtain maximal recombinant viral titres. In the latter case, after one round of infection/integration, the 3' LTR U3 is now also the 5' LTR U3, giving the desired tissue-specific expression.

In a third embodiment, the proviral vector construct is similarly activated but expresses a protein which is not itself cytotoxic, and which processes within the target cells a compound or a drug with little or no cytotoxicity into one which is cytotoxic (a "conditionally lethal" gene product). Specifically, the proviral vector construct carries the herpes simplex virus thymidine kinase ("HSVTK") gene downstream and under the transcriptional control of an HIV promoter (which is known to be transcriptionally silent except when activated by HIV tat protein). Expression of the tat gene product in human cells infected with HIV and carrying the proviral vector construct causes increased production of HSVTK. The cells (either in vitro or in vivo) are then exposed to a drug such as acyclovir or its analogues (FIAU, FIAC, DHPG). These drugs are known to be phosphorylated by HSVTK (but not by cellular thymidine kinase) to their corresponding active nucleotide triphosphate forms (see, for example, Schaeffer et al., Nature 272:583, 1978). Acyclovir and FIAU triphosphates inhibit cellular polymerases in general, leading to the specific destruction of cells expressing HSVTK in transgenic mice (see Borrelli et al., Proc. Natl. Acad. Sci. USA 85:7572, 1988). Those cells containing the recombinant vector and expressing HIV tat protein are selectively killed by the presence of a specific dose of these drugs. In addition, an extra level of specificity is achieved by including in the vector the HIV rev protein, responsive. CRS/CAR sequences. In the presence of the CRS sequence gene expression is suppressed, except in the presence of the CAR sequences and the rev protein. Example 5 provides an illustration of this technique.

EXAMPLE 5

Vector to Conditionally Potentiate the Toxic Action of ACV or Its Analogues

Construction of Vectors

A. Construction of pKTVIHAX (see FIG. 7).

1. The 9.2 kb Asu II/Xho I fragment was isolated from vector pN2 DNA.

2. The 0.6 kb Xho I/Bam HI promoter fragment was isolated from plasmid pSKHL.

3. The 0.3 kb Bgl II/Acc I and 1.5 kb Acc I/Acc I fragment were purified from pUCTK.

4. The fragments from 1, 2, and 3 were ligated, transformed into bacteria, and appropriate Amp' clones of the given structure identified by restriction enzyme analysis.

Figure 8:
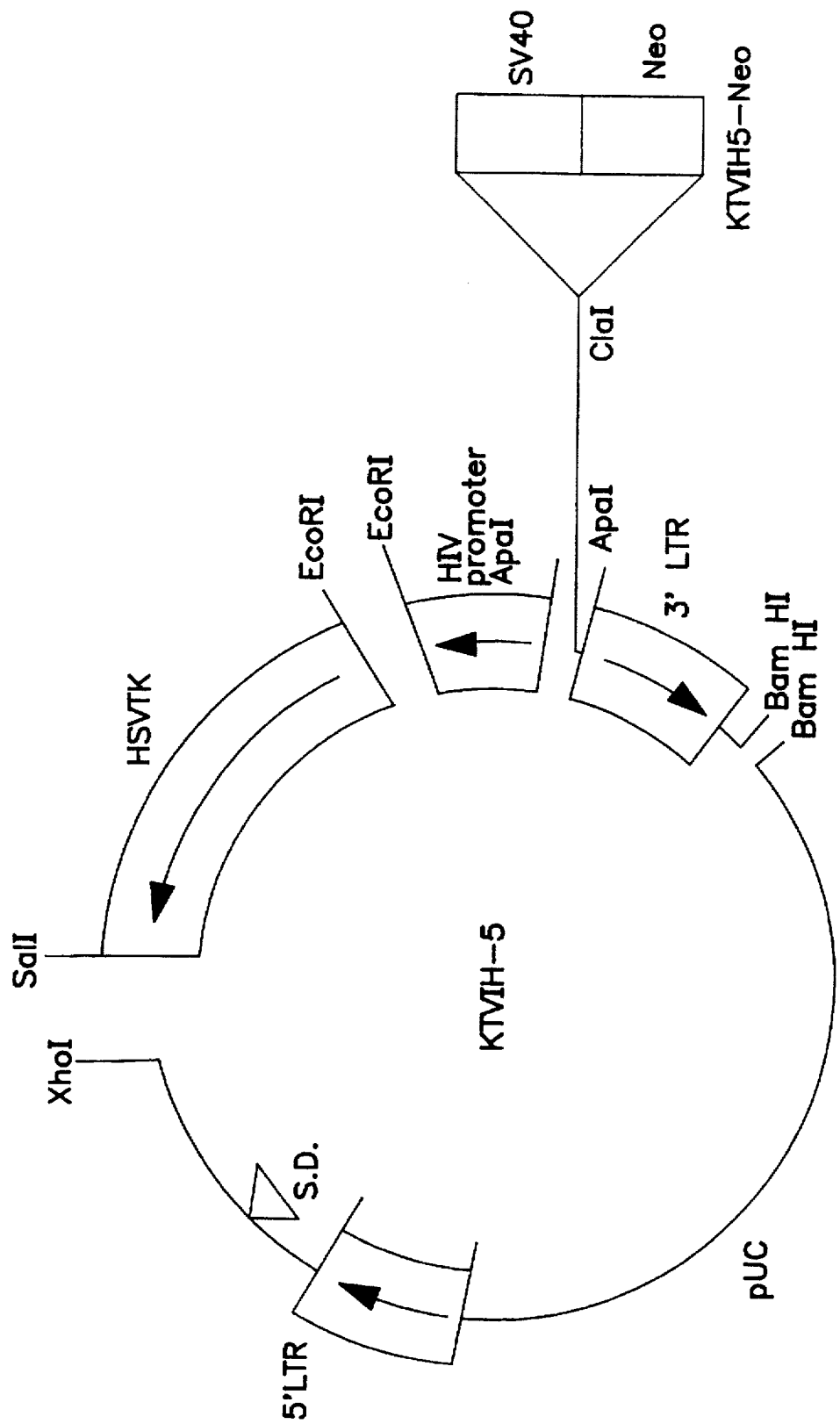
FIG. 8 illustrates the construction of the plasmids carrying the vectors KTVIH5 (without SV-Neo) and KTVIH Neo (with SV-Neo).

B. Construction of pKTVIH-5 and pKTVIH5 Neo retroviral vectors (see FIG. 8).

1. The 4.5 kb 5' LTR and vector fragment was isolated as an Xho I/Bam HI fragment from vector p31N25delta(+).

2. The 1.0 kb 3' LTR was isolated as an Apa I/Bam HI fragment from pN2R3(+) fragment.

3. The 0.6 kb HIV promoter element was isolated from pSKHL as an Apa I/Eco R1 fragment.

4. The HSVTK coding sequence and transcriptional termination sequences were isolated as 1.8 kb Eco R1/Sal I fragment from pUCTK.

5. The fragments from 1–4 were combined, ligated, transformed into bacteria, and clones of the given structure were identified by restriction enzyme analysis (pKTVIH-5).

6. Plasmid pKTVIH5 Neo was constructed by linearizing pKTVIH5 with Cla I; mixing with a 1.8 kb Cla I fragment containing the bacterial lac UV5 promoter, SV40 early promoter, and Tn5 Neo' marker, ligating, transforming bacteria and selecting for kanamycin resistance. Clones with the insert in the indicated orientation were identified by restriction analysis.

Figure 9:
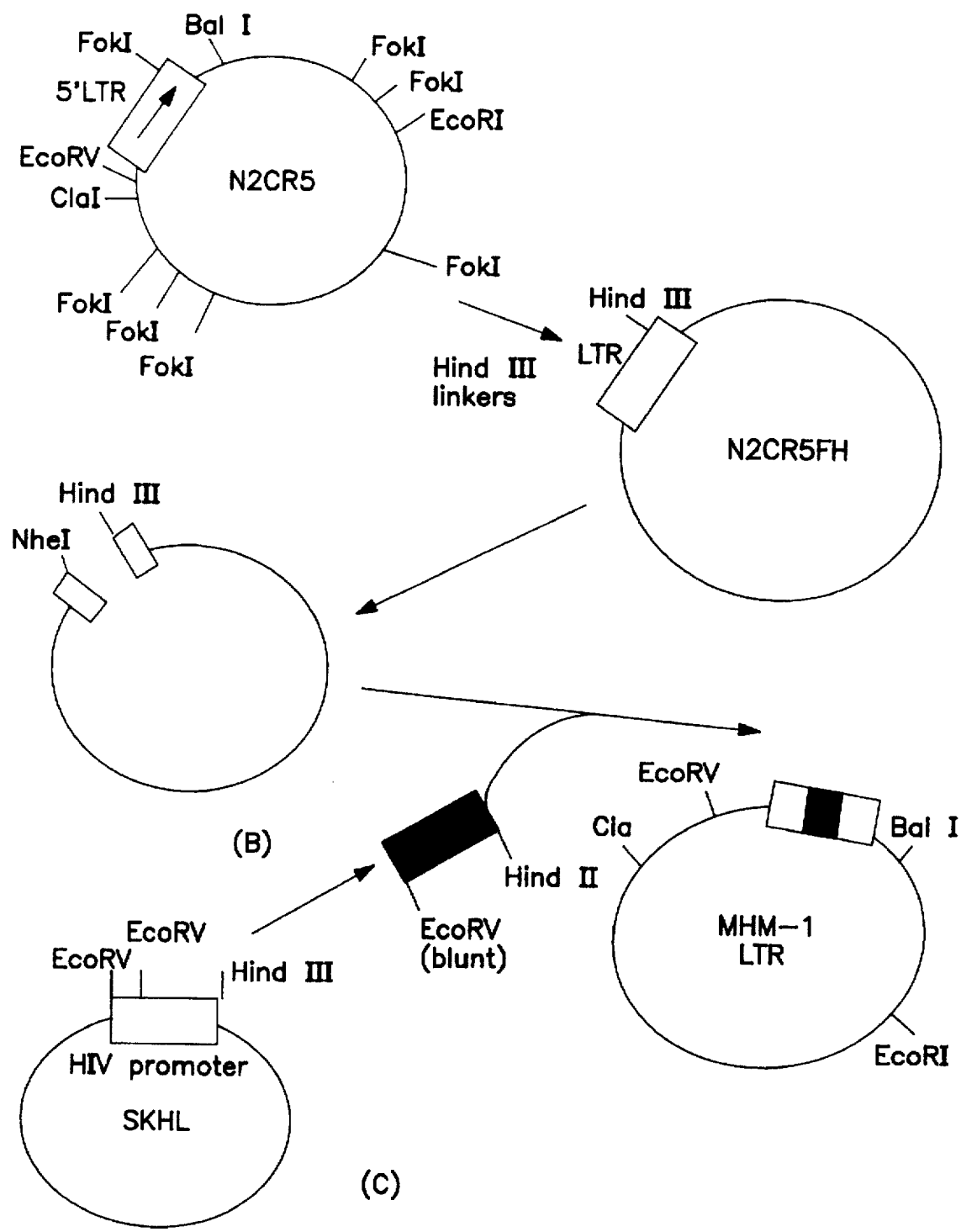
FIG. 9 illustrates construction of the plasmid carrying the vector MHMTK-Neo.

C. Construction of MHMTK Neo retroviral vector (see FIG. 9).

1. Construction of intermediate plasmid MHM-1 LTR.

a) Plasmid pN2CR5 was linearized by partial digestion with Fok I, the 5' overhang filled in with deoxynucleotide triphosphates using Klenow DNA polymerase, and Hind III linkers inserted. After transformation into bacteria, a clone with a Hind III linker inserted in the MLV LTR Fok I site was identified by restriction enzyme analysis (pN2CR5FH).

b) Plasmid pN2CR5FH was linearized with Nhe I, the 5' overhang filled in with Klenow polymerase digested with Hind III, and the 4.3 kb fragment with promoterless MLV sequences isolated.

c) 0.5 kb Eco RV/Hind III HIV promoter sequences were isolated from pSKHL.

d) b and c were mixed, ligated, used to transform bacteria, and the structure of MHM-1 was confirmed by restriction enzyme analysis.

2. The 0.7 kb Eco RV/Bal I fragment isolated from MHM-1 was subcloned into the Eco RV site of plasmid I30B (a modified IBI30 plasmid containing additional Bgl II, Bst II, Neo I and Nde I sites in the polylinker). After transformation into bacteria, clones with the appropriate orientation were identified by restriction enzyme analysis (pMHMB).

3. Plasmid pMHMB was digested with Apa I and Xho I and gel purified.

4. MHM-1 was digested with Apa I/Bam HI and the 1.8 kb MHMLTR/leader sequence gel purified.

5. The 2.8 kb Bgl II/Sal I fragment containing the HSVTK coding region upstream of the SV40 early promoter driving Neo' taken from pTK-3 (see FIG. 3).

6. 3–5 were mixed, ligated, used to transform bacteria, and appropriate clones were identified by restriction enzyme analysis.

This vector and similar vectors which contain inducible elements in their LTR's result in an added safety feature. Briefly, since the LTR is inactive in the absence of HIV, insertional downstream activation of undesirable host genes (such as proto-oncogenes) does not occur. However, tat expression in the packaging cell line allows facile manipulation of the virion in tissue culture.

D. Construction of RRKTVIH retroviral vector (see FIG. 10)

1. The 9.2 kb Asu II/Xho I fragment was isolated from vector pN2 DNA.

2. The 0.6 kb Xho I/Eco R1 HIV promoter fragment was isolated from plasmid pSKHL.

3. The HIV rev responsive HSVTK (RRTK) was constructed in the following manner:

a) The HSVTK gene was subcloned as a 1.8 kb HinC II/Pvu II fragment into the Eco RV site of vector SK+ (pSTK[−]).

b) The 1.8 kb Kpn I/Hind III fragment which contains the CRS/CAR elements from HIV env was repaired and blunt-end ligated into the Sma I site of vector I30B (pCRS/CAR[±]). I30B is a modified IBI30 plasmid containing the same additional restriction sites as for pUC31 with an Nde I site instead of the IBI30 Xho I site.

c) The 3.6 kb BssH II/Eco R1 fragment containing vector and HSVTK polyadenylation signals was isolated from pSTK(–).

d) The 1.8 kb Bam HI/BssH II CRS/CAR fragment was isolated from pCRS/CAR(–).

e) The 1.2 Eco R1/Bam HI coding sequence fragment was isolated from pTKdeltaA.

f) C, D and E were ligated and appropriate recombinants screened by restriction enzyme analysis.

4. Rev-responsive HSVTK was isolated as a 3.6 kb Eco R1/Cla I fragment.

5. 1, 2 and 4 were ligated and appropriate recombinants identified by restriction enzyme analysis.

Figure 11:
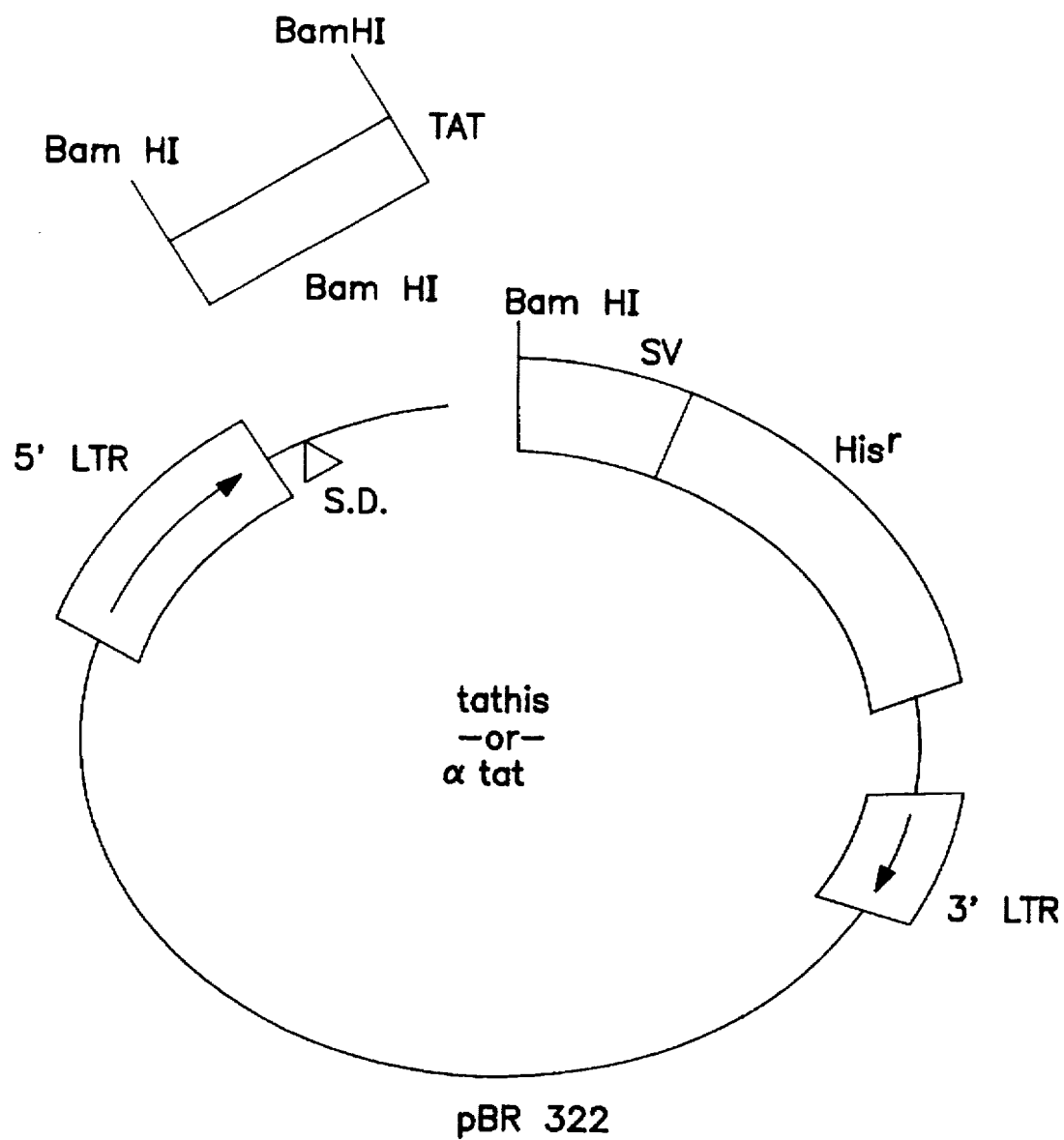
FIG. 11 illustrates the construction of the plasmids carrying the tat-his (tat in sense direction) or αtat (tat in antisense direction) vectors.

E. Construction of tat and anti-tat expression vectors (see FIG. 11).

These vectors are used as pseudo-HIV to test-activate tat-dependent HSVTK vectors.

1. The His$^r$ expression vector pBamHis was linearized with Bam HI and treated with calf intestinal phosphatase.

2. The Sac I site of pCV-1 was mutagenized to a Bam HI site and the 350 bp Bam HI coding sequence of HIV tat was isolated.

3. The fragments purified in steps 1 and 2 were mixed, ligated, used to transform bacteria, and clones with tat in both orientations (expressing tat or the "anti-sense" tat) were identified by restriction enzyme analysis.

These constructs were used to generate infectious recombinant vector particles in conjunction with a packaging cell line such as PA317, as described above. These vectors are genetically stable and result in predictable proviral structure as judged by Southern blot analysis of restriction-enzyme-digested genomic DNA from individual clones of infected cells (39/40 clones tested had proviruses of the expected size).

Figure 12:
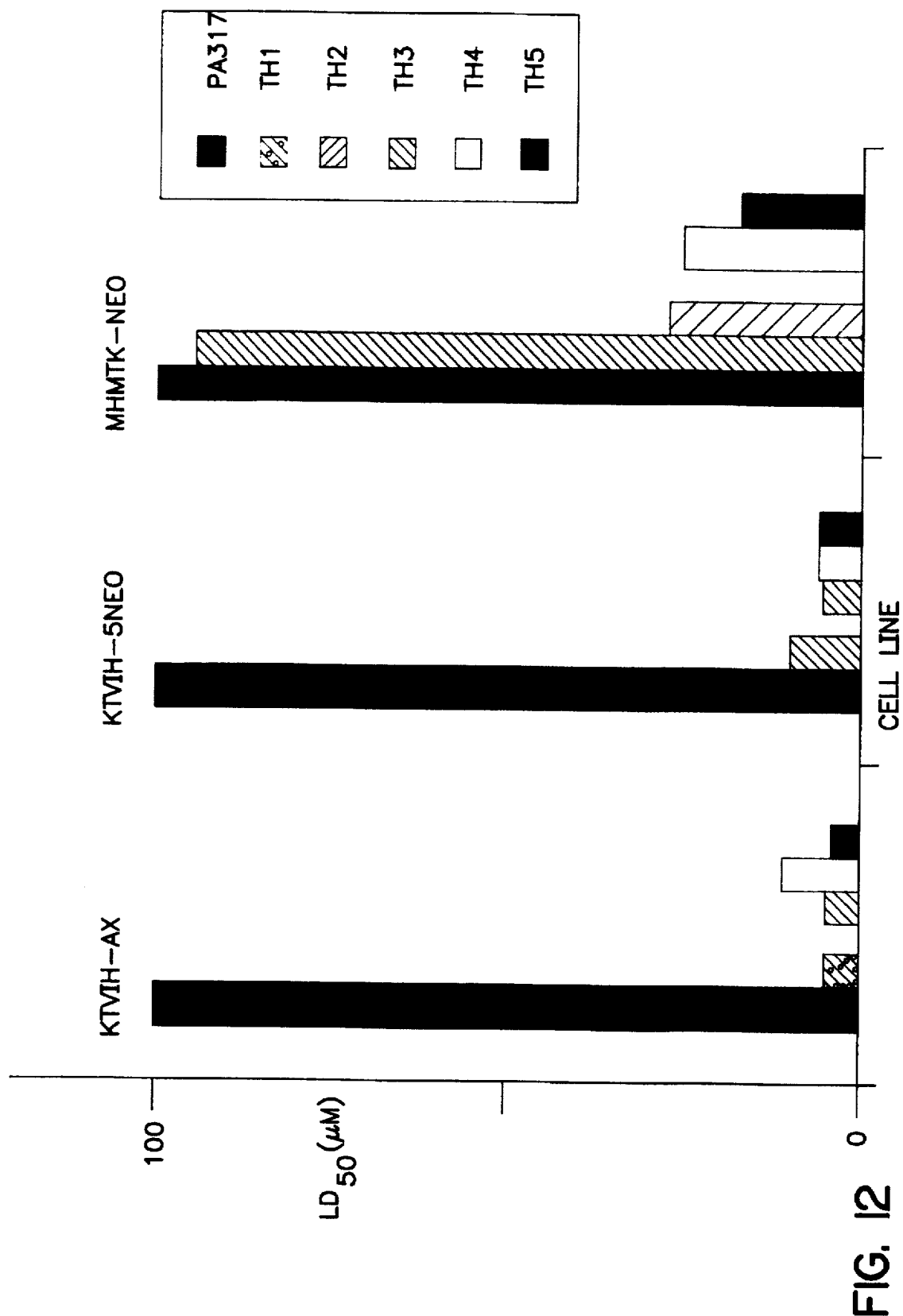
FIG. 12 graphically depicts the preferential killing of PA317 cells infected with this vector (5 clones, TH1-5) compared to control PA317, upon infection with the three conditional lethal vectors shown and treatment with acyclovir (ACV).
Figure 13:
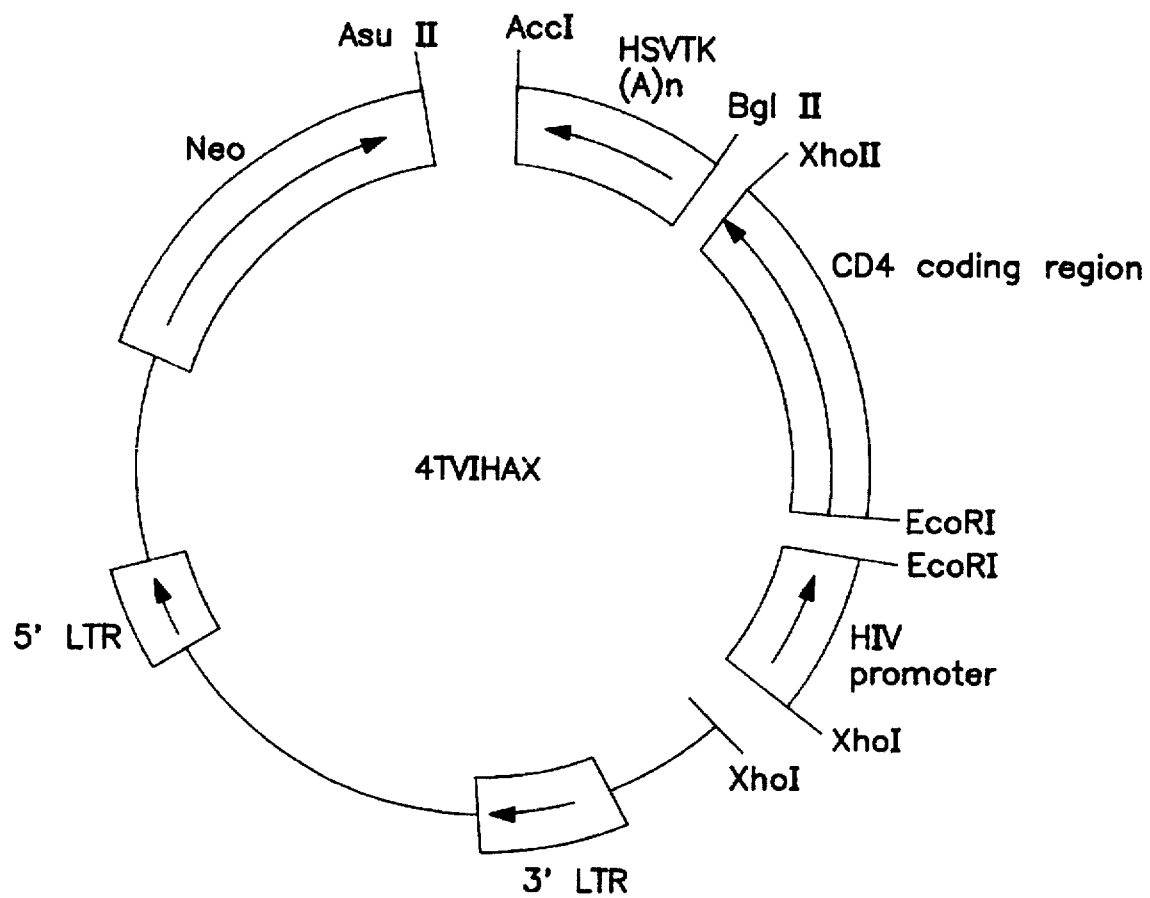
FIG. 13 illustrates the constuction of the plasmid carrying the vector 4TVIHAX.

The biological properties of these retroviral vectors are described hereinafter. The HIV tat gene ("tathis" vector—see FIG. 11) was transfected into mouse PA317 cells. Five individual histidinol-resistant subclones were obtained (TH 1–5) which express HIV tat. These cells are thus an experimental model for HIV infection. The vectors KTVIHAX, KTVIH5NEO, and MHMTKNEO, were subsequently introduced by infection into these tat-expressing cell lines as well as their parent cell line lacking tat. Cell viability was then determined in various concentrations of the HSVTK-specific cytotoxic drug, acyclovir (ACV). The data are reported here as LD50 (the drug concentration at which 50% toxicity is observed). The parental cell line containing the vector but lacking tat (non-HIV-infected model) showed no detectable toxicity by ACV at the concentrations tested (see FIG. 12). These cells thus require 100 uM ACV or greater for cytotoxicity. This is true also for these cells lacking the vectors. Thus the vectors alone, ACV alone, or even the vector +ACV (solid boxes) is not cytotoxic. However, cell lines which express HIV tat (the experimental representation of an HIV infection) are effectively killed by ACV. This is true to varying degrees for all three vectors tested. These data indicate that HIV-infected cells will be killed in the presence of ACV and "potentiator" vectors.

In an analogous experiment, vectors KTVIHAX and KTVIH5 Neo were introduced by infection into human T-cell and monocyte cell lines SupT1, HL60 and U937 cells. Subsequently, these cells were infected with tat his or otat vectors, selected in histidinol, and cell viability determined at various concentrations of the ACV analog, FIAU. The $LD_{50}$ reported in Table 1 (below) indicate that a vector dependent increase in FIAU toxicity occurs in the absence of HIV tat but is increased an additional ten- to twentyfold when tat is present. This indicates that although there is a baseline HSVTK expression in all but HL60 cells, expression is even greater in the presence of HIV tat.

TABLE 1

HIV tat inducibility of FIAU cytotoxicity in human monocyte and T-cell lines infected with conditonally lethal recombinant retroviral vectors

| Cell Type | Vectors | tat | LD50FIAU (μM) |
|---|---|---|---|
| HL50 ("monocyte") | — | – | 50 |
|  | — | + | 50 |
|  | KTVIHAX | – | 50 |
|  | KTVIHAX | + | <0.2 |
|  | KTVIH5Neo | – | 50 |
|  | KTVIH5NeO | + | <0.2 |
| U937 ("monocyte") | — | – | 10 |
|  | KTVIHAX | – | 0.5 |
|  | KTVIHAX | + | 0.05 |
|  | KTVIHAX | + | 0.05 |
|  | KTVIH5NeO | – | 0.5 |
|  | KTVIH5NeO | + | 0.05 |
| Sup T1 ("T-cell") | — | – | 10 |
|  | — | + | 5 |
|  | KTVIHAX | – | ).5 |
|  | KTVIHAX | + | 0.05 |
|  | KTVIH5NeO | – | 0.5 |
|  | KTVIH5NeO | + | 0.05 |
| H9 ("T-cell") | — | – | 10 |
|  | KTVIHAX | – | 2 |
|  | KTVIHAX | + | 0.2 |
|  | KTVIH5NeO | – | 1 |
|  | KTVIH5NeO | + | 0.05 |

Similarly, HIV infection of human T-cell line H9±FIAU show a fivefold preferential inhibition (through cell killing) of HIV infection. Cultures were first treated with vector, then challenged with HIV for 4 days. Viral supernatants were then titred using the HIV assay, as described in Section IV.

In the case of HIV-infected cells, expression of the conditionally lethal HSVTK gene may be made even more HIV-specific by including cis-acting elements in the transcript ("CRS/CAR"), which require an additional HIV gene product, rev, for optimal activity (Rosen et al., Proc. Natl. Acad. Sci. USA 85:2071, 1988). Such a tat- and rev-responsive vector (RRKTVIH) has been constructed (see FIG. 10) and amphotropic virus has been generated. More generally, cis elements present in mRNAs have been shown in some cases to regulate mRNA stability or translatability. Sequences of this type (i.e., post-transcriptional regulation of gene expression) may be used for event- or tissue-specific regulation of vector gene expression. In addition, multimerization of these sequences (i.e., rev-responsive "CRS/CAR" or tat-responsive "TAR" elements for HIV) could result in even greater specificity. It should be noted that this kind of conditional activation of an inactive precursor into an active product in cells may also be achieved using other viral vectors with a shorter term effect, e.g., adenovirus vectors. Such vectors are capable of efficiently entering cells and expressing proteins encoded by the vector over a period of time from a couple of days to a month or so. This period of time should be sufficient to allow killing of cells which are infected by both HIV and the recombinant virus, leading to HIV dependent activation of expression of a gene carried by the recombinant virus. This gene expression would then allow conversion of an inactive precursor into an active (e.g., lethal) product.

Production, concentration and storage of vector preparations is as previously described. Administration is by direct in vivo administration as before or by ex corpore treatment of PBL and/or bone marrow. Doses will be at approximately the same levels as for Example 4. Targeting of viral vector infection will not be through the CD4 receptor, but may be accomplished through producing vector particles which will infect cells using the HIV env protein (gp120) as a receptor. Such HIV-tropic viruses may be produced from an MLV-based packaging cell line constructed from cells which have naturally high levels of CD4 protein in their cell membrane (for example, Sup T1 cells) or from any cell type "engineered" to express the protein. The resultant virions, which form by budding from the cell membrane itself, contain the CD4 protein in their membrane. Since membranes containing CD4 are known to fuse with membranes carrying HIV env, these virions should fuse with cells containing HIV env and result in the specific infection of HIV-infected cells which have gp120 on their surface. Such a packaging cell line may require the presence of an MLV env protein to allow proper virion assembly and budding to result in infectious virions. If so, an MLV env which does not infect human cells (such as ecotropic env) would be used such that viral entry will occur only through the CD4/HIV env interaction and not through the MLV env cell receptor, which would presumably not depend upon the presence of HIV-env for infection. Alternatively, the requirement for MLV env may be satisfied by a hybrid envelope where the amino-terminal binding domain has been replaced by the amino-terminal HIV-env binding domain of CD4. This inversion of the normal virus-receptor interaction can be used for all types of viruses whose corresponding cellular receptor has been identified.

In a similar manner to the preceding embodiment, the retroviral vector construct can carry a gene for phosphorylation, phosphoribosylation, ribosylation, or other metabolism of a purine- or pyrimidine-based drug. This gene may have no equivalent in mammalian cells and might come from organisms such as a virus, bacterium, fungus, or protozoan. An example of this would be the *E. coli* guanine phosphoribosyl transferase gene product, which is lethal in the presence of thioxanthine (see Besnard et al., *Mol. Cell. Biol.* 7:4139–4141, 1987). Conditionally lethal gene products of this type have potential application to many presently known purine- or pyrimidine-based anticancer drugs, which often require intracellular ribosylation or phosphorylation in order to become effective cytotoxic agents. The conditionally lethal gene product could also metabolize a nontoxic drug, which is not a purine or pyrimidine analogue, to a cytotoxic form (see Searle et al., *Brit. J. Cancer* 53:377–384, 1986).

Mammalian viruses in general tend to have "immediate early" genes which are necessary for subsequent transcriptional activation from other viral promoter elements. Gene products of this nature are excellent candidates for intracellular signals (or "identifying agents") of viral infection. Thus, conditionally lethal genes from transcriptional promoter elements responsive to these viral "immediate early" gene products could specifically kill cells infected with any particular virus. Additionally, since the human α and β interferon promoter elements are transcriptionally activated in response to infection by a wide variety of nonrelated viruses, the introduction of vectors expressing a conditionally lethal gene product like HSVTK, for example, from these viral-responsive elements (VRE) could result in the destruction of cells infected with a variety of different viruses.

In a fourth embodiment, the recombinant retrovirus carries a gene specifying a product which is not in itself toxic, but when processed or modified by a protein, such as a protease specific to a viral or other pathogen, is converted into a toxic form. For example, the recombinant retrovirus could carry a gene encoding a proprotein for ricin A chain, which becomes toxic upon processing by the HIV protease. More specifically, a synthetic inactive proprotein form of the toxic ricin or diphtheria A chains could be cleaved to the active form by arranging for the HIV virally encoded protease to recognize and cleave off an appropriate "pro" element.

In a fifth embodiment, the retroviral construct may express a "reporting product" on the surface of the target cells in response to the presence of an identifying agent in the cells (such as HIV tat protein). This surface protein can be recognized by a cytotoxic agent, such as antibodies for the reporting protein or by cytotoxic T-cells. In a similar manner, such a system can be used as a detection system (see below) to simply identify those cells having a particular gene which expresses an identifying protein, such as the HIV tat gene.

Similarly, in a sixth embodiment, a surface protein could be expressed which would itself be therapeutically beneficial. In the particular case of HIV, expression of the human CD4 protein specifically in HIV-infected cells may be beneficial in two ways:

1. Binding of CD4 to HIV env intracellularly could inhibit the formation of viable viral particles much as soluble CD4 has been shown to do for free virus, but without the problem of systematic clearance and possible immunogenicity, since the protein will remain membrane bound and is structurally identical to endogenous CD4 (to which the patient should be immuno-logically tolerant).

2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monocytes and macrophages, which act as a reservoir for virus production as a result of their relative refractility to HIV-induced cytotoxicity (which, in turn, is apparently due to the relative lack of CD4 on their cell surfaces).

EXAMPLE 6

Construction of p4TVIHAX retroviral vector (see FIG. 13)

1. The 9.4 kb Asu II/Xho I fragment was isolated from pN2.

2. The 0.6 kb Xho I/Eco R1 HIV promoter fragment was isolated from pSKHL.

3. The 1.4 kb coding region for human CD4 was isolated as an Eco R1/Bst Y1 (Xho II) fragment from the expression vector, pMV7T4.

4. The (A)n signal of HSVTK was isolated as a 0.3 kb Apa I/Sma I fragment, 3' repaired with T4 polymerase and dNTP'as and cloned into the Sma I site of pUC31. After transforming bacteria, clones were screened for orientation by restriction enzyme analysis (p31[A]n[±]). The 0.3 kb (A)n signal was then isolated as a 0.3 kb Bgl II/Acc I fragment.

5. 1–4 clones were mixed, ligated, used to transform bacteria and clones were identified by restriction enzyme analysis.

Recombinant amphotropic retroviruses have been produced and introduced into human monocyte and T-cell lines lacking or containing the HIV tat expression vector, tathis. Syncytia assays with HIV env-expressing mouse fibroblasts show that monocyte cell lines HL60 and U937 themselves lack sufficient CD4 to fuse with these cells. However, HL60 and U937 cells containing vector 4TVIHAX can fuse with the reporter cells (HIV-env expressing cells) when HIV tat is present, but not in its absence. These data indicate that CD4 expression is inducible and biologically active (as judged by syncytia formation). Experiments with the vector in human T-cell line, H9, indicated exceptionally high toxicity due to HIV infection and a correspondingly low HIV titre (more than 200-fold lower than the HIV titre produced in H9 cells lacking the vector).

In a seventh embodiment, the retroviral vector codes for a ribozyme which will cleave and inactivate RNA molecules essential for viability of the vector infected cell. By making ribozyme production dependent on an intracellular signal corresponding to the pathogenic state, such as HIV tat, toxicity is specific to the pathogenic state.

IV. Immune Down-Regulation

As briefly described above, the present invention provides recombinant retroviruses which carry a vector construct capable of suppressing one or more elements of the immune system in target cells infected with the retrovirus.

Specific down-regulation of inappropriate or unwanted immune responses, such as in chronic hepatitis or in transplants of heterologous tissue such as bone marrow, can be engineered using immune-suppressive viral gene products which suppress surface expression of transplantation (MHC) antigen. Group C adenoviruses Ad2 and Ad5 possess a 19 kd glycoprotein (gp 19) encoded in the E3 region of the virus. This gp 19 molecule binds to class I MHC molecules in the endoplasmic reticulum of cells and prevents terminal glycosylation and translocation of class I MHC to the cell surface. For example, prior to bone marrow transplantation, donor bone marrow cells may be infected with gp 19-encoding vector constructs which upon expression of the gp 19 inhibit the surface expression of MHC class I transplantation antigens. These donor cells may be transplanted with low risk of graft rejection and may require a minimal immunosuppressive regimen for the transplant patient. This may allow an acceptable donor-recipient chimeric state to exist with fewer complications. Similar treatments may be used to treat the range of so-called autoimmune diseases, including lupus erythromatosis, multiple sclerosis, rheumatoid arthritis or chronic hepatitis B infection.

An alternative method involves the use of anti-sense message, ribozyme, or other specific gene expression inhibitor specific for T-cell clones which are autoreactive in nature. These block the expression of the T-cell receptor of particular unwanted clones responsible for an autoimmune response. The anti-sense, ribozyme, or other gene may be introduced using the viral vector delivery system.

V. Expression of Markers

The above-described technique of expressing a palliative in a cell, in response to some identifying agent, can also be modified to enable detection of a particular gene in a cell which expresses an identifying protein (for example, a gene carried by a particular virus), and hence enable detection of cells carrying that virus. In addition, this technique enables the detection of viruses (such as HIV) in a clinical sample of cells carrying an identifying protein associated with the virus.

This modification can be accomplished by providing a genome coding for a product, the presence of which can be readily identified (the "marker product"), and carrying a promoter, which responds to the presence of the identifying protein in indicator cells, by switching expression of the reporting product between expressing and nonexpressing states. For example, HIV, when it infects suitable indicator cells, makes tat and rev. The indicator cells can thus be provided with a genome (such as by infection with an appropriate recombinant retrovirus) which codes for a marker gene, such as the alkaline phosphatase gene, β-galactosidase gene or the luciferase gene, and a promoter, such as the HIV promoter, which controls expression of the marker gene. When the indicator cells are exposed to a clinical sample to be tested, and the sample contains HIV, the indicator cells become infected with HIV, resulting in tat and/or rev expression (an identifying protein) therein. The HIV expression controls in the indicator cells would then respond to tat and/or rev proteins by switching expression of genes encoding β-galactosidase, luciferase, or alkaline phosphatase (marker products) from normally "off" to "on." In the case of β-galactosidase or alkaline phosphatase, exposing the cells to substrate analogues results in a color or fluorescence change if the sample is positive for HIV. In the case of luciferase, exposing the sample to luciferin will result in luminescence if the sample is positive for HIV. For intracellular enzymes such as β-galactosidase, the viral titre can be measured directly by counting colored or fluorescent cells, or by making cell extracts and performing a suitable assay. For the membrane bond form of alkaline phosphatase, virus titre can also be measured by performing enzyme assays on the cell surface using a fluorescent substrate. For secreted enzymes, such as an engineered form of alkaline phosphatase, small samples of culture supernatant are assayed for activity, allowing continuous monitoring of a single culture over time. Thus, different forms of this marker system can be used for different purposes. These include counting active virus or sensitively and simply measuring viral spread in a culture and the inhibition of this spread by various drugs.

Further specificity can be incorporated into the preceding system by testing for the presence of the virus either with or without neutralizing antibodies to that virus. For example, in one portion of the clinical sample being tested, neutralizing antibodies to HIV may be present; whereas in another portion there would be no neutralizing antibodies. If the tests were negative in the system where there were antibodies and positive where there were no antibodies, this would assist in confirming the presence of HIV.

Within an analogous system for an in vitro assay, the presence of a particular gene, such as a viral gene, may be determined in a cell sample. In this case, the cells of the sample are infected with a suitable retroviral vector which carries the reporter gene linked to the expression controls of the virus of interest. The reporter gene, after entering the sample cells, will express its reporting product (such as β-galactosidase or luciferase) only if the host cell expresses the appropriate viral proteins.

These assays are more rapid and sensitive, since the reporter gene can express a greater amount of reporting product than identifying agent present, which results in an amplification effect. Example 7 describes a representative technique for detecting a gene which expresses an identifying protein.

EXAMPLE 7

HIV-Specific Marker System or Assay

A. Constructs

Figure 14:
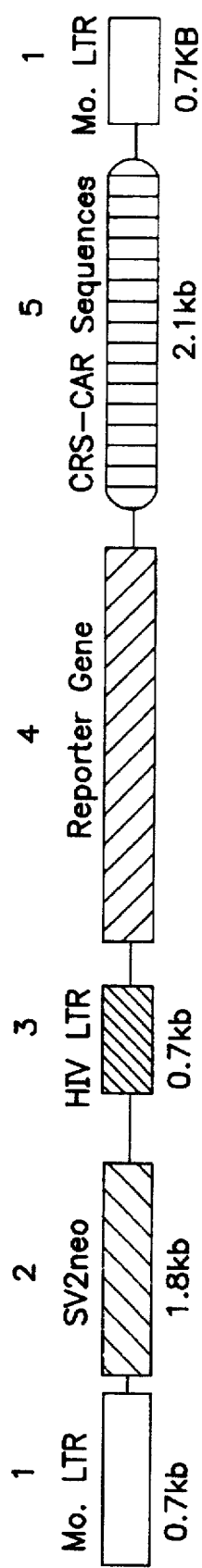
FIG. 14 depicts the construction of a viral vector carrying HIV inducible marker/reporter genes such as alkaline phosphatase (AP).
Figure 15:
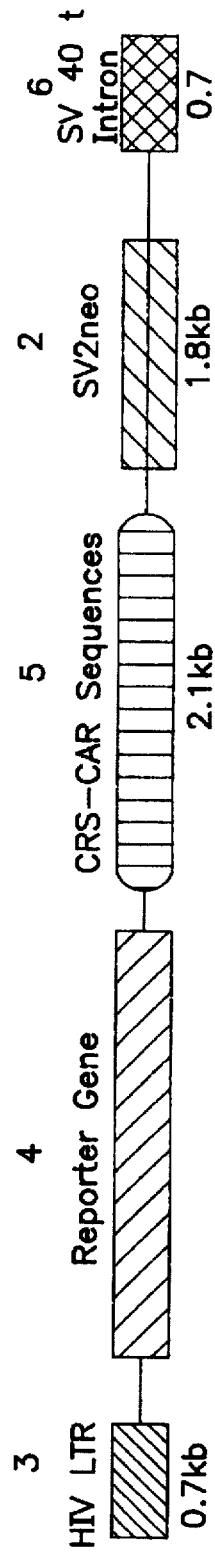
FIG. 15 depicts the structure of an HIV inducible marker/reporter gene carried on a plasmid which can be transfected into cells.

Reporter constructs under the control of the HIV expression system are shown in FIG. 14 (a recombinant retroviral vector) and in FIG. 15 (a simple plasmid used by transfection). The pieces of these preferred vector and plasmid reporters were derived as follows:

The retroviral backbone was derived from the construct pAFVXM (Krieger et al., Cell 38:384, 1984), which had been linearized using Xho I and Cla I. SV$_2$neo was obtained from the plasmid pKoneo (Hanahan, unpubl.) by isolation of the 1.8 kb Cla I fragment.

The HIV LTR was isolated as a 0.7 kb Hind III fragment from the plasmid pC15CAT (Arya et al., Science 229:69, 1985). Beta-gal was obtained from the plasmid pSP65 β-gal (Cepko, pers. comm.) as a Hind III-Sma I fragment. A secreted form of human placental alkaline phosphatase was produced by introduction of a universal terminator sequence after amino-acid 489 of the cell surface form of alkaline phosphatase (as described by Berger et al., Gene 66:1, 1988). The secreted alkaline phosphatase gene was isolated as a 1.8 kb Hind III to Kpn I fragment. The CRS-CAR sequences from HIV env were obtained by isolating the 2.1 kb Kpn I to Bam HI fragment from HTLVIIIB/BH1OR3 (Fisher et al., Science 233:655, 1986). This fragment was inserted into pUC31 linearized by Bam HI, and Kpn I pUC31 is pUC19 (Yanisch-Perron et al., Gene 33:103, 1985) with extra Xho I, Bgl II, Bssh II and Nco I sites between the Eco R1 and Kpn I sites of pUC19. The Bam HI site of the resulting construct was converted to a Nco I site to allow resection of the CRS-CAR sequences by Nco I digestion. The SV40 t intron was obtained from pSVOL (de Wet et al., Mol. Cell. Biol. 7:725, 1987) as a 0.8 kb Nco I to Bam HI fragment.

B. Indicator Cells and Retroviral Vectors

Human T-cell (H-9, CEM and Sup T1) and monocyte (U-937) cell lines were obtained from ATCC, and maintained in RPM1 1640 medium supplemented with 10% fetal bovine serum and 1% penicillin/streptomycin.

The nonretroviral vectors were introduced into cell lines by electroporation using a Bio-Rad Gene Pulser. The cell lines were selected in G-418 (1 mg/ml) for 2–3 weeks to obtain stable G-418$_R$ cell lines, and then dilution cloned to obtain clonal cell lines.

The pAF vectors were transfected into the PA317 packaging cell line as a calcium phosphate precipitate (Wigler et al., Cell 16:777, 1979). The virus-producing PA317 cells were co-cultivated with human monocyte cell lines for 24 hours in the presence of polybrene, after which the suspension cells were removed and selected in G-418 and subcloned as above.

C. Assay

Stable cell lines were infected with HIV (HTLV III$_B$) and the cells (β-gal) or media (alkaline phosphatase) assayed on a daily basis for 6 days post-infection.

β-Galactosidase Assay

Infected cells could be assayed by either: (i) In situ histochemical staining as described by MacGregor et al. Somatic Cell and Mol. Genetics 23:253, 1987); or (ii) by using cell extracts in a solution enzymatic assay with ONPG as a substrate (Norton and Coffin, Mol. Cell. Biol. 5:281, 1985).

Soluble Alkaline Phosphatase Assay

Medium was removed from infected cells, microfuged for 10 seconds, and then heated to 68° C. for 10 minutes to destroy endogenous phosphatases. The medium was then microfuged for 2 minutes and an aliquot (10–50 µl) removed for assay. 100 µl of buffer (1M diethanolamine, pH 9.8; 0.5 Mm MgCl$_2$; 10 mM L-homoarginine) was added and then 20 µl of 120 mM p-nitrophenylphosphate (in buffers) was added. The A$_{405}$ of the reaction mixture was monitored using an automatic plate reader.

Figure 16:
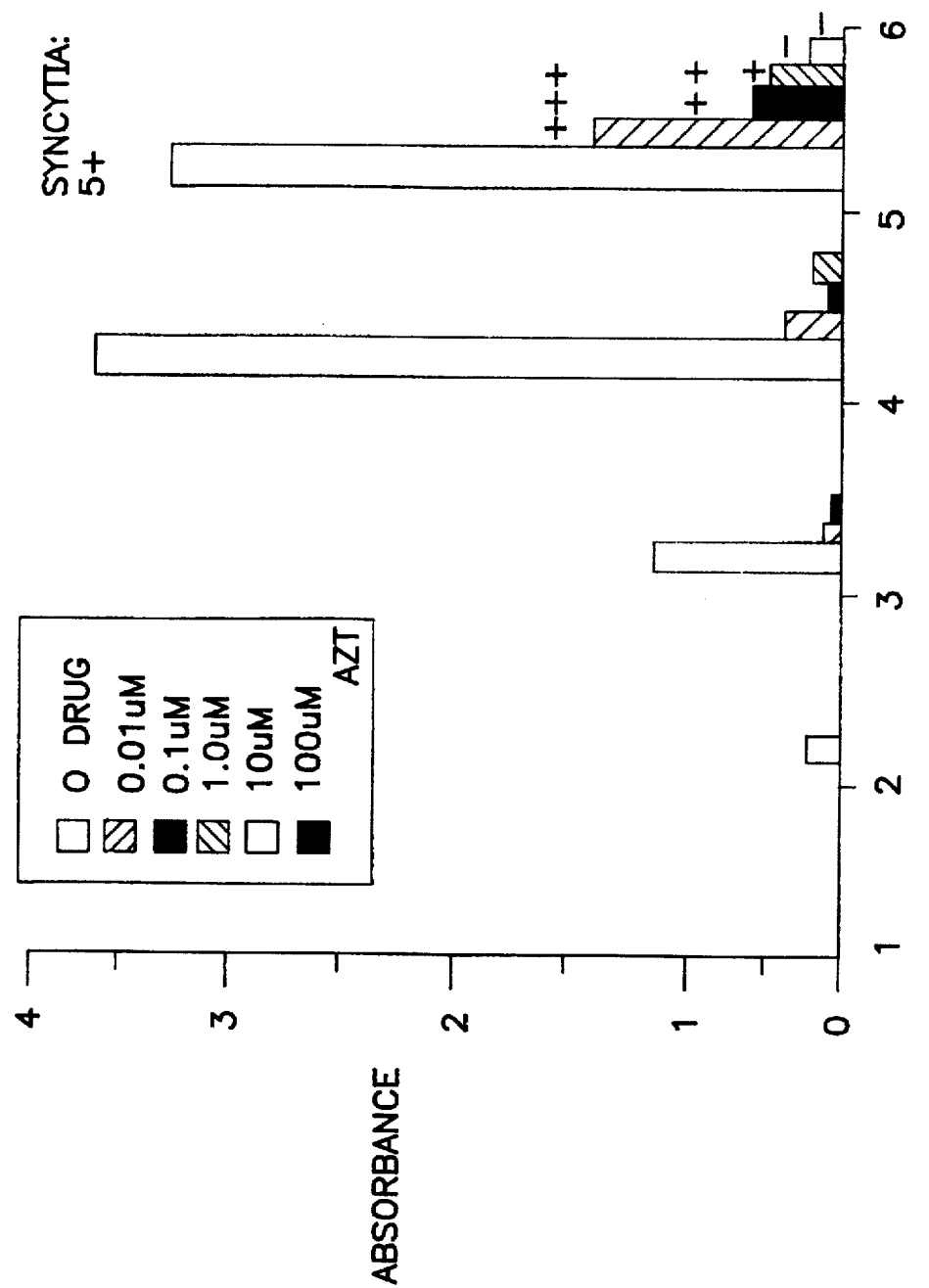
FIG. 16 graphically depicts a time course of HIV infection of Sup T1 cells carrying the AP marker in FIG. 15 with HIV at various concentrations of AZT. The level of HIV infection was measured by taking small aliquots of supernatant.
Figure 17:
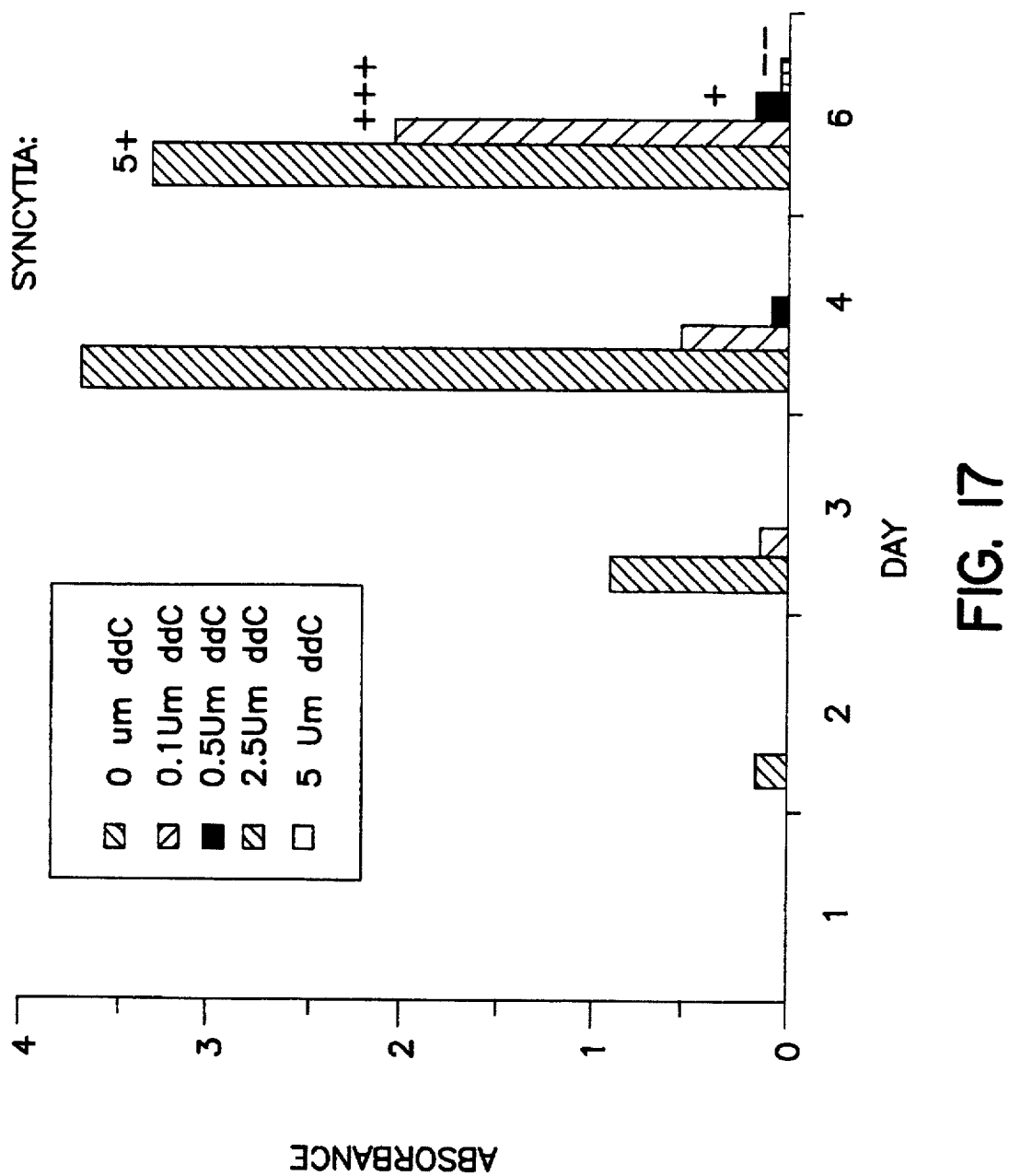
FIG. 17 graphically depicts the results of the same experiment as in FIG. 16, but with ddC as the HIV inhibitor.

FIGS. 16 and 17 depict typical results of a time course of infection of Sup T1 cells using the alkaline phosphatase assay in the presence of varying concentrations of antiviral drugs. The "+" and "−" on day 6 indicate the presence or absence of syncytia.

The present invention provides a number of other techniques (described below) which can be used with the retroviral vector systems employed above, so as to enhance their performance. Alternatively, these techniques may be used with other gene-delivery systems.

VI. Packaging Cell Selection

This aspect of the present invention is based, in part, upon the discovery of the major causes of low recombinant virus titres from packaging cells, and of techniques to correct those causes. Basically, at least five factors may be postulated as causes for low recombinant virus titres:

1. the limited availability of viral packaging proteins;
2. the limited availability of retroviral vector RNA genomes;
3. the limited availability of cell membrane for budding of the recombinant retroviruses;
4. the limited intrinsic packaging efficiency of the retroviral vector genome; and
5. the density of the receptor specific for the envelope of a given retrovirus.

As noted above, the limited availability of viral packaging proteins is the initial limiting factor in recombinant retrovirus production from packaging cells. When the level of packaging protein in the packaging cells is increased, titre increases to about 10$^5$ infectious units/milliliter, following which increasing packaging protein level has no further effect on titres. However, titres can be further augmented by also increasing the level of retroviral vector genome available for packaging. Thus, as described herein, it is advantageous to select producer cells that manufacture the maximum levels of packaging proteins and retroviral vector genomes. It has been discovered that the methods of identifying, and thus selecting, packaging cells and producer cells, described earlier under the section entitled "Background of the Invention," tend to lead to selection of many producer cells which produce low titres for the reasons described below.

Figure 18:
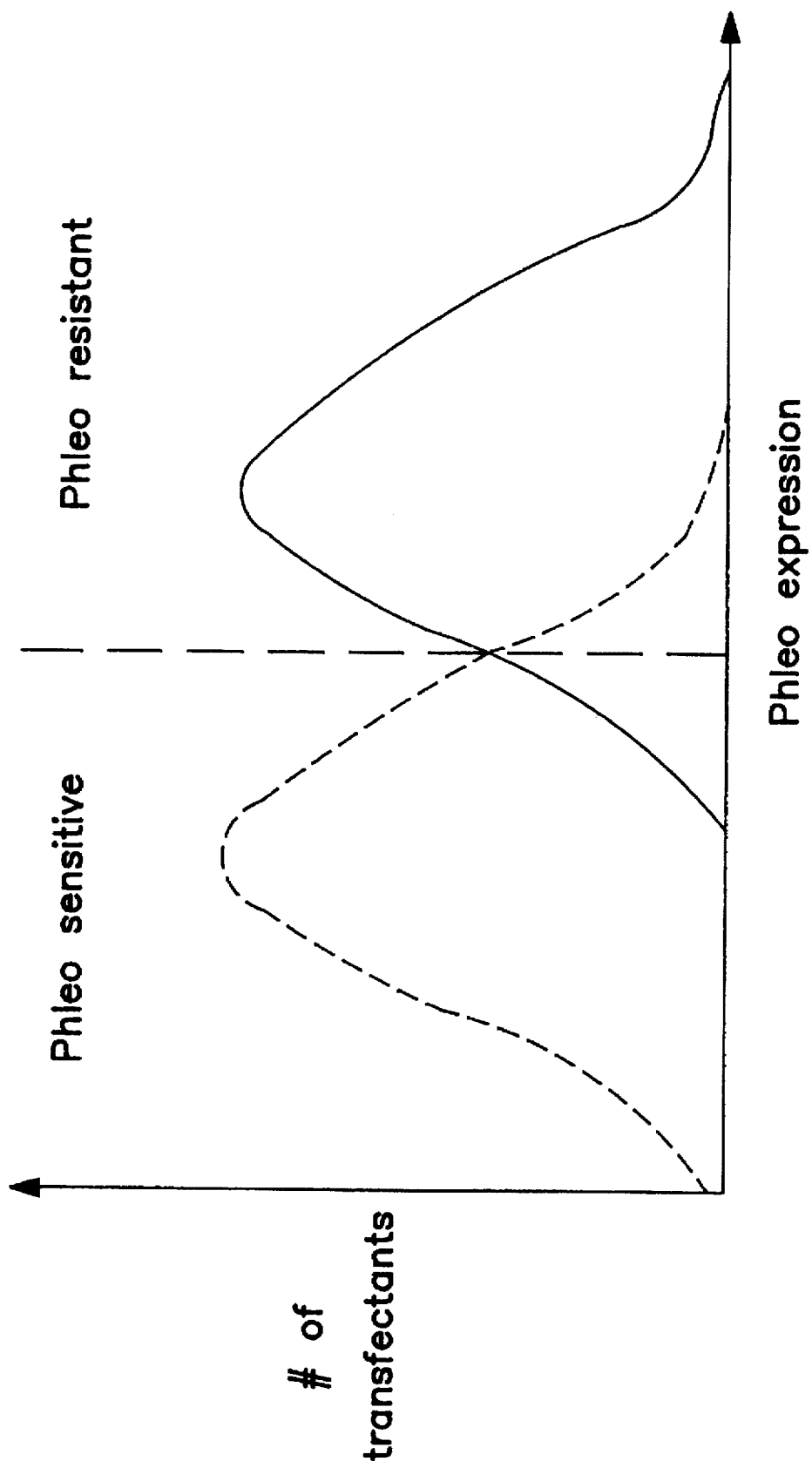
FIG. 18 diagrammatically illustrates the number of cells surviving after phleomycin selection upon transfection of cells with a plasmid which expresses the phlemoycin resistance gene (PRG) directly from a promoter (right, complete lime), and with another which expresses PRG with a coding sequence interposed between it and the promoter (left, dotted line).

The present invention takes advantage of the previously disadvantageous fact that the protein expression level of a gene downstream from the 5' LTR or other promoter, and spaced therefrom by an intervening gene, is substantially less than if the intervening gene were absent. In the present invention, the selectable gene is placed downstream from a gene of the packaging genome or the gene of interest carried by the vector construct, but is still transcribed under the control of the viral 5' LTR or other promoter without any splice donor or splice acceptor sites. This accomplishes two things. First, since the packaging genes or genes of interest are now upstream with no intervening gene between themselves and the promoter, their corresponding proteins (packaging protein or protein of interest) will be expressed at a higher level (five- to twentyfold) than the selectable protein. Second, the selectable protein will be expressed on average at a lower level, with the distribution of level of expression shifting toward lower levels. In the case of the phleo$^r$ protein, this shift in distribution is illustrated by the broken curve indicated in FIG. 18. However, the selection level for resistance to phleomycin remains the same, so that only the top-end expressing cells survive. The levels of the packaging protein or of the protein of interest will still be proportional, only in this case, a higher level of selectable protein corresponds to a much higher level of packaging protein or protein of interest.

Preferably, the foregoing procedure is performed using a plasmid carrying one of the proviral gag/pol or env packaging genes, along with a first selectable gene. These cells are then screened for the cells producing the highest levels of protein by reaction with an antibody against env (or possibly gag/pol), a second fluorescent antibody, and then sorted on a fluorescence-activated cell sorter (FACS). Alternatively, other tests for protein level may be used. Subsequently, the procedure and screening are repeated using those selected cells, and the other of the gag/pol or env packaging genes. In this step, a second selectable gene (different from the first) would be required downstream from the packaging gene and the cells producing the largest amount of the second viral protein selected. .The procedure and screening are then repeated using the surviving cells, with a plasmid carrying the proviral vector construct bearing the gene of interest and a third selectable gene, different from the first or second selectable gene. As a result of this procedure, cells producing high titres of the desired recombinant retrovirus will be selected, and these can be cultured as required to supply recombinant retrovirus. In addition, gag and pol can be independently introduced and selected.

Example 8 describes the construction of gag/pol and env plasmids designed to use these procedures.

EXAMPLE 8

Figure 19:
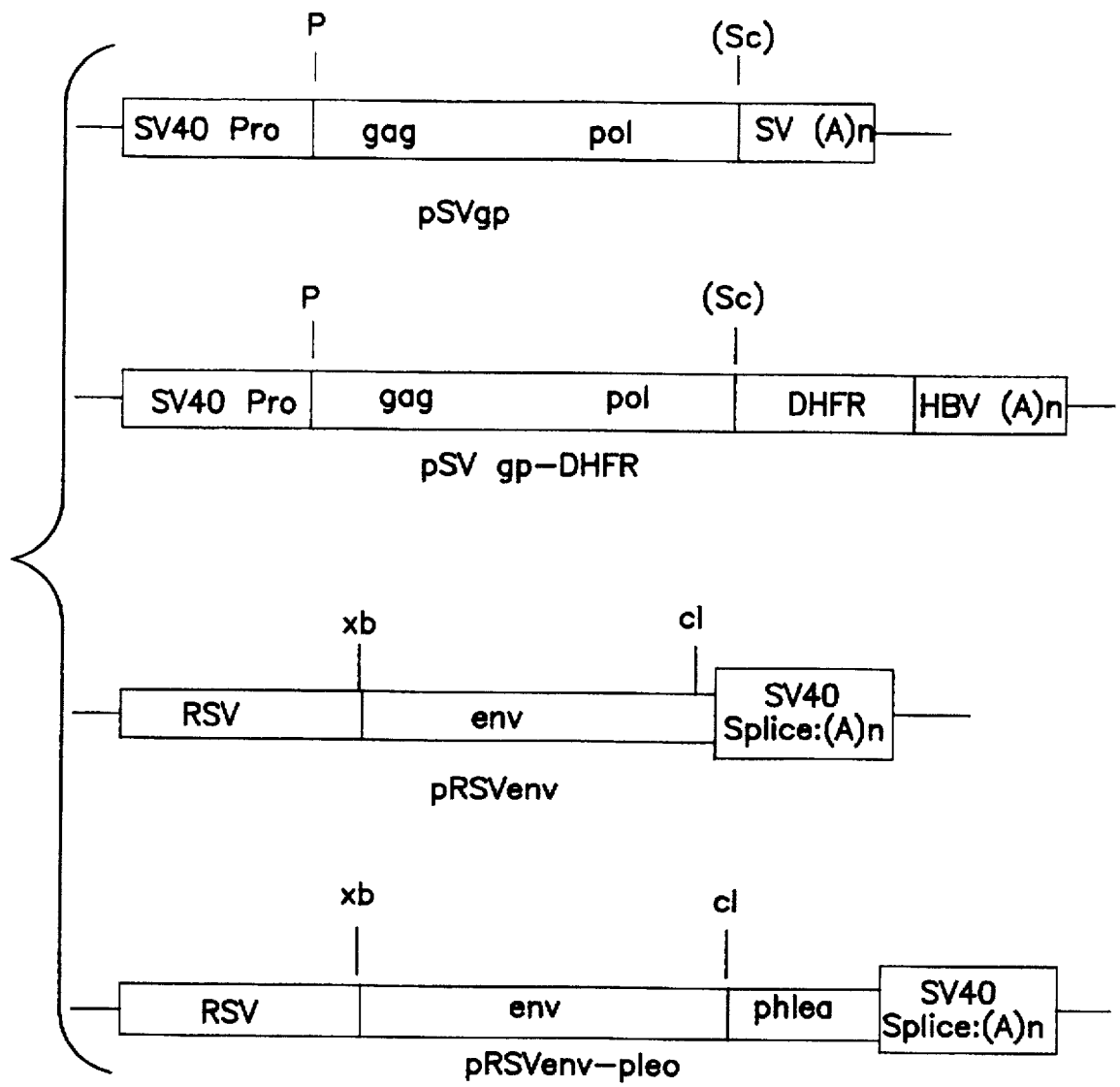
FIG. 19 depicts four plasmids designed to express retroviral proteins in mammalian cells. pSVgp and pRSVenv are cotransfected with a selectable marker, while pSVgp-DHFR and pRSVenv-phleo are the equivalent plasmids with the selectable marker placed downstream of the viral protein-coding regions.

Plasmids Designed to Make High Levels of Packaging Proteins of (FIG. 19)

1. The 2.7 kb Xba I fragment from pPAM (Miller et al., *Mol. Cell. Biol.* 5:431, 1985), which contains the amphotrophic env segment, was cloned in pUC18 at the Xba I site, then removed with Hind III and Sma I. This fragment was cloned into the vector pRSV neo (Gorman et al., *Mol. Cell. Biol.* 2:1044, 1982; Southern et al., *J. Mol. Appl. Genet.* 1:327, 1982) cut with Hind III and Pvu II, to give pRSV env. A 0.7 kb Bam HI to BstE II fragment from the plasmid pUT507 (Mulsant et al., *Somat. Cell. Mol. Genet.* 14:243, 1988) with the BstE II end filled in carries the phleo resistance coding sequence. The 4.2 kb Bam HI to Xho I fragment, the contiguous 1.6 kb Xho I to Xba I (Xba I filled in) from RSVenv, and the phleo fragment were ligated to give pRSVenv-phleo.

2. A fragment from the Pst I site at nucleotide 563 of MLV (*RNA Tumor Viruses*, Vol. II, Cold Spring Harbor, 1985) to the Sca I site at 5870 was derived from pMLV-K (Miller et al., 1985, op. cit.) and cloned in the Pst I to Bam HI (Bam HI filled-in) fragment from p4aA8 (Jolly et al., *Proc. Natl. Acad. Sci. USA* 80:477, 1983) that has the SV40 promoter, the pBR322 ampicillin resistance and origin of replication and the SV40 poly A site. This gives pSVgp. pSVgpDHFR was made using the following fragments: the 3.6 kb Hind III to Sal I fragment from pSVgp containing the SV40 promoter plus MLV gag and some pol sequences; the 2.1 kb Sal I to Sca I fragment from pMLV-K with the rest of the pol gene, the 3.2 kb Xba I (Xba I filled-in) to Pst I fragment from pF400 with the DHFR gene plus poly A site, pBR322 origin and half the ampicillin resistance gene; the 0.7 kb Pst I to Hind III fragment from pBR322 with the other half of the ampicillin resistance gene. This gives pSVgp-DHFR. All these constructs are shown in FIG. 19. These plasmids can be transfected into 3T3 cells or other cells and high levels of gag, pol or env obtained.

An additional method for accomplishing selection is to use a gene selection in one round and its antisense in a subsequent round. For example, gag/pol may be introduced into an HPRT-deficient cell with the HPRT gene and selected for the presence of this gene using that media which requires HPRT for the salvage of purines. In the next round, the antisense to HPRT could be delivered downstream to env and the cell selected in 6 thioguanine for the HPRT-deficient phenotype. Large amounts of antisense HPRT would be required in order to inactivate the HPRT gene transcripts, assuming no reversion occurred.

In addition to the gag/pol expressing constructs which begin at nucleotide 563 of MoMLV, several others can be constructed which contain upstream lead sequences. It has been observed by Prats et al. (*RNA Tumor Viruses Meeting*, Cold Spring Harbor, N.Y., 1988) that a glycosylated form of the gag protein initiates at nucleotide 357 and a translation enhancer maps in the region between nucleotides 200–270. Therefore, gag/pol expressing constructs may be made beginning at the Bal I site (nucleotide 212) or Eag I site (nucleotide 346) to include these upstream elements and enhance vector production.

Envelope Substitutions

The ability to express gag/pol and env function separately allows for manipulation of these functions independently. A cell line that expresses ample amounts of gag/pol can be used, for example, to address questions of titre with regard to env. One factor resulting in low titres is the density of appropriate receptor molecules on the target cell or tissue. A second factor is the affinity of the receptor for the viral envelope protein. Given that env expression is from a separate unit, a variety of envelope genes (requiring different receptor proteins), such as xenotropic, polytropic, or amphotrophic envs from a variety of sources, can be tested for highest titres on a specific target tissue. Furthermore, envelopes from nonmurine retrovirus sources can be used for pseudotyping a vector. The exact rules for pseudotyping (i.e., which envelope proteins will interact with the nascent vector particle at the cytoplasmic side of the cell membrane to give a viable viral particle (Tato, *Virology* 88:71, 1978) and which will not (Vana, *Nature* 336:36, 1988), are not well characterized. However, since a piece of cell membrane buds off to form the viral envelope, molecules normally in the membrane are carried along on the viral envelope. Thus, a number of different potential ligands can be put on the surface of viral vectors by manipulating the cell line making gag and pol in which the vectors are produced or choosing various types of cell lines with particular surface markers. One type of surface marker that can be expressed in helper cells and that can give a useful vector-cell interaction is the receptor for another potentially pathogenic virus. The pathogenic virus displays on the infected cell surface its virally specific protein (e.g., env) that normally interacts with the cell surface marker or receptor to give viral infection. This reverses the specificity of the infection of the vector with respect to the potentially pathogenic virus by using the same viral protein-receptor interaction, but with the receptors on the vector and the viral protein on the cell.

It may be desirable to include a gene which encodes for an irrelevant envelope protein which does not lead to infection of target cells by the vector so produced, but does facilitate the formation of infectious viral particles. For example, one could use human Sup T1 cells as a helper line. This human T-cell line expresses CD4 molecules at high levels on its surface. Conversion of this into a helper line can be achieved by expressing gag/pol with appropriate expression vectors and also, if necessary, the Moloney ecotropic env gene product as an irrelevant (for human cells) envelope protein (the Moloney ecotropic env only leads to infection of mouse cells). Vectors produced from such a helper line would have CD4 molecules on their surfaces and are capable of infecting only cells which express HIV env, such as HIV-infected cells.

In addition, hybrid envelopes (as described below) can be used in this system as well, to tailor the tropism (and effectively increase titres) of a retroviral vector. A cell line that expresses ample amounts of a given envelope gene can be employed to address questions of titre with regard to gag and pol.

Cell Lines

The most common packaging cell lines used for MoMLV vector systems (psi2, PA12, PA317) are derived from murine cell lines. There are several reasons why a murine cell line is not the most suitable for production of human therapeutic vectors:

1. They are known to contain endogenous retroviruses.
2. They contain nonretroviral or defective retroviral sequences that are known to package efficiently.
3. There may be deleterious effects caused by the presence of murine cell membrane components.

Several non-murine cell lines are potential packaging lines. These include Vero cells which are used in Europe to prepare polio vaccine, WI38 which are used in the U.S. in vaccine production, CHO cells which are used in the U.S. for TPA preparation and D17 or other dog cells that may have no endogenous viruses.

Although the factors that lead to efficient infection of specific cell types by retroviral vectors are not completely understood, it is clear that because of their relatively high mutation rate, retroviruses may be adapted for markedly improved growth in cell types in which initial growth is poor, simply by continual reinfection and growth of the virus in that cell type (the adapter cell). This can also be achieved using viral vectors that encode some viral functions (e.g., env), and which are passed continuously in cells of a particular type which have been engineered to have the functions necessary to complement those of the vector to give out infectious vector particles (e.g., gag/pol). For example, one can adapt the murine amphotropic virus 4070A to human T-cells or monocytes by continuous growth and reinfection of either primary cell cultures or permanent cell lines such as Sup T1 (T-cells) or U937 (monocytes). Once maximal growth has been achieved, as measured by reverse transcriptase levels or other assays of virus production, the virus is cloned out by any of a number of standard methods, the clone is checked for activity (i.e., the ability to give the same maximal growth characteristic on transfection into the adapter cell type) and this genome used to make defective helper genomes and/or vectors which in turn, in an appropriately manufactured helper or producer line, will lead to production of viral vector particles which infect and express in the adapter cell type with high efficiency ($10^8$–$10^9$ infectious units/ml).

VII. Alternative Viral Vector Packaging Techniques

Two additional alternative systems can be used to produce recombinant retroviruses carrying the vector construct. Each of these systems takes advantage of the fact that the insect virus, baculovirus, and the mammalian viruses, vaccinia and adenovirus, have been adapted recently to make large amounts of any given protein for which the gene has been cloned. For example, see Smith et al. (*Mol. Cell. Biol.* 3:12, 1983); Piccini et al. (*Meth. Enzymology*, 153:545, 1987); and Mansour et al. (*Proc. Natl. Acad. Sci. USA* 82:1359, 1985).

These viral vectors can be used to produce proteins in tissue culture cells by insertion of appropriate genes into the viral vector and, hence, could be adapted to make retroviral vector particles.

Adenovirus vectors are derived from nuclear, replicating viruses and can be defective. Genes can be inserted into vectors and used to express proteins in mammalian cells either by in vitro construction (Ballay et al., *EMBO J.* 4:3861, 1985) or by recombination in cells (Thummel et al., *J. Mol. Appl. Genetics* 1:435, 1982).

One preferred method is to construct plasmids using the adenovirus Major Late Promoter (MLP) driving: (1) gag/pol, (2) env, (3) a modified viral vector construct. A modified viral vector construct is possible because the U3 region of the 5' LTR, which contains the viral vector promoter, can be replaced by other promoter sequences (see, for example, Hartman, *Nucl. Acids Res.* 16:9345, 1988). This portion will be replaced after one round of reverse transcriptase by the U3 from the 3' LTR.

These plasmids can then be used to make adenovirus genomes in vitro (Ballay et al., op. cit.), and these transfected in 293 cells (a human cell line making adenovirus E1A protein), for which the adenoviral vectors are defective, to yield pure stocks of gag/pol, env and retroviral vector carried separately in defective adenovirus vectors. Since the titres of such vectors are typically $10^7$–$10^{11}$/ml, these stocks can be used to infect tissue culture cells simultaneously at high multiplicity. The cells will then be programmed to produce retroviral proteins and retroviral vector genomes at high levels. Since the adenovirus vectors are defective, no large amounts of direct cell lysis will occur and retroviral vectors can be harvested from the cell supernatants.

Other viral vectors such as those derived from unrelated retroviral vectors (e.g., RSV, MMTV or HIV) can be used in the same manner to generate vectors from primary cells. In one embodiment, these adenoviral vectors are used in conjunction with primary cells, giving rise to retroviral vector preparations from primary cells.

In an alternative system (which is more truly extracellular), the following components are used:

1. gag/pol and env proteins made in the baculovirus system in a similar manner as described in Smith et al. (supra) (or in other protein production systems, such as yeast or *E. coli*);

2. viral vector RNA made in the known T7 or SP6 or other in vitro RNA-generating system (see, for example, Flamant and Sorge, *J. Virol.* 62:1827, 1988);

3. tRNA made as in (2) or purified from yeast or mammalian tissue culture cells;

4. liposomes (with embedded env protein); and 5. cell extract or purified necessary components (when identified) (typically from mouse cells) to provide env processing, and any or other necessary cell-derived functions.

Within this procedure (1), (2) and (3) are mixed, and then env protein, cell extract and pre-liposome mix (lipid in a suitable solvent) added. It may, however, be necessary to earlier embed the env protein in the liposomes prior to adding the resulting liposome-embedded env to the mixture of (1), (2), and (3). The mix is treated (e.g., by sonication, temperature manipulation, or rotary dialysis) to allow encapsidation of the nascent viral particles with lipid plus embedded env protein in a manner similar to that for liposome encapsidation of pharmaceuticals, as described in Gould-Fogerite et al., *Anal. Biochem.* 148:15, 1985). This procedure allows the production of high titres of replication incompetent recombinant retroviruses without contamination with pathogenic retroviruses or replication-competent retroviruses.

VIII. Cell Line-Specific Retroviruses—"Hybrid Envelope"

The host cell range specificity of a retrovirus is determined in part by the env gene products. For example, Coffin, J. (*RNA Tumor Viruses* 2:25–27, Cold Spring Harbor, 1985) notes that the extracellular component of the proteins from murine leukemia virus (MLV) and Rous Sarcoma virus (RSV) are responsible for specific receptor binding. The cytoplasmic domain of envelope proteins, on the other hand, are understood to play a role in virion formation. While pseudotyping (i.e., the encapsidation of viral RNA from one species by viral proteins of another species) does occur at a low frequency, the envelope protein has some specificity for virion formation of a given retrovirus. The present invention recognizes that by creating a hybrid env gene product (i.e., specifically, an env protein having cytoplasmic regions and exogenous binding regions which are not in the same protein molecule in nature) the host range specificity may be changed independently from the cytoplasmic function. Thus, recombinant retroviruses can be produced which will specifically bind to preselected target cells.

In order to make a hybrid protein in which the receptor binding component and the cytoplasmic component are from different retroviruses, a preferred location for recombination is within the membrane-spanning region of the cytoplasmic component. Example 9 describes the construction of a hybrid env gene which expresses a protein with the CD4 binding portion of the HIV envelope protein coupled to the cytoplasmic domain of the MLV envelope protein.

EXAMPLE 9

Hybrid HIV-MLV Envelopes

A hybrid envelope gene is prepared using in vitro mutagenesis (Kunkel, *Proc. Natl. Acad. Sci. USA* 82:488–492, 1985) to introduce a new restriction site at an appropriate point of junction. Alternatively, if the two envelope sequences are on the same plasmid, they can be joined directly at any desired point using in vitro mutagenesis. The end result in either case is a hybrid gene containing the 5' end of the HIV gp 160 and the 3' end of MLV p15E. The hybrid protein expressed by the resulting recombinant gene is illustrated in FIG. 20 and contains the HIV gp120 (CD4 receptor binding protein), the extracellular portion of HIV gp 41 (the gp 120 binding and fusigenic regions), and the cytoplasmic portion of MLV p15E, with the joint occurring at any of several points within the host membrane. A hybrid with a fusion joint at the cytoplasmic surface (joint C in FIG. 20) causes syncytia when expressed in Sup T1 cells. The number of apparent syncytia are approximately one-fifth that of the nonhybrid HIV envelope gene in the same expression vector. Syncytia with the hybrid occurs only when the rev protein is co-expressed in trans. A hybrid with a fusion joint at the extracellular surface (joint A in FIG. 20) gives no syncytia while hybrid B (in the middle of the transmembrane regions) gives approximately five-fold less syncytium on Sup T1 cells than hybrid C.

While Example 9 illustrates one hybrid protein produced from two different retroviruses, the possibilities are not limited to retroviruses or other viruses. For example, the beta-receptor portion of human interleukin-2 may be combined with the envelope protein of MLV. In this case, a recombination would preferably be located in the gp 70 portion of the MLV env gene, leaving an intact p15E protein. Furthermore, the foregoing technique may be used to create a recombinant retrovirus with an envelope protein which recognizes antibody Fc segments. Monoclonal antibodies which recognize only preselected target cells only could then be bound to such a recombinant retrovirus exhibiting such envelope proteins so that the retrovirus would bind to and infect only those preselected target cells.

IX. Site-Specific Integration

Targeting a retroviral vector to a predetermined locus on a chromosome increases the benefits of gene-delivery systems. A measure of safety is gained by direct integration to a "safe" spot on a chromosome, i.e., one that is proven to have no deleterious effects from the insertion of a vector. Another potential benefit is the ability to direct a gene to an "open" region of a chromosome, where its expression would be maximized. Two techniques for integrating retroviruses at specific sites are described below.

(i) Homologous Recombination

One technique for integrating an exogenous gene of a vector construct of a recombinant retrovirus into a specific site in a target cell's DNA employs homologous recombination. Plasmids containing sequences of DNA of greater than about 300 bp that are homologous to genomic sequences have been shown to interact (either by replacement or insertion) with those genomic sequences at a rate that is greater than $10^3$-fold over a specific interaction in the absence of such homology (see Thomas and Capecchi, *Cell* 51:503–12, 1987; and Doetscheman et al., *Nature* 330:576–78, 1987). It has been shown that an insertion event, or alternatively, a replacement event, may be driven by the specific design of the vector.

In order to employ homologous recombination in site-specific retroviral integration, a vector construct should be modified such that (a) homologous sequences (to the target cell's genome) are incorporated into the construct at an appropriate location; and (b) the normal mechanism of integration does not interfere with the targeting occurring due to homologous sequences. A preferred approach in this regard is to add homologous sequences (greater than about 300 bp) in the 3' LTR, downstream from the U3 inverted repeat. In this approach, the construct is initially made with a region of homology inserted in the 3' LTR at the Nhe 1 site in U3. Reverse transcription in the host cell will result in a duplication of the region of homology in the 5' LTR within 31 bp of the end of the inverted repeat (IR). Integration into the host genome will occur in the presence or absence of the normal integration mechanism. The gene in the vector may be expressed, whether from the LTR or from an internal promoter. This approach has the effect of placing a region of homology near a potential free end of the double-stranded retrovirus vector genome. Free ends are known to increase the frequency of homologous recombination by a factor of approximately ten. In this approach, it may be necessary to defeat the normal mechanism of integration, or to at least modify it to slow down the process, allowing time for homologous DNAs to line up. Whether this latter modification is required in a particular case can be readily ascertained by one skilled in the art.

(ii) Integrase Modification

Another technique for integrating a vector construct into specific, preselected sites of a target cell's genome involves integrase modification.

The retrovirus pol gene product is generally processed into four parts: (i) a protease which processes the viral gag and pol products; (ii) the reverse transcriptase; and (iii) RNase H, which degrades RNA of an RNA/DNA duplex; and (iv) the endonuclease or "integrase."

The general integrase structure has been analyzed by Johnson et al. (*Proc. Natl. Acad. Sci. USA* 83:7648–7652, 1986). It has been proposed that this protein has a zinc binding finger with which it interacts with the host DNA before integrating the retroviral sequences.

In other proteins, such "fingers" allow the protein to bind to DNA at particular sequences. One illustrative example is the steroid receptors. In this case, one can make the estrogen receptor, responding to estrogens, have the effect of a glucocorticoid receptor, responding to glucocorticoids, simply by substituting the glucocorticoid receptor "finger" (i.e., DNA binding segment) in place of the estrogen receptor finger segment in the estrogen receptor gene. In this example, the position in the genome to which the proteins are targeted has been changed. Such directing sequences can also be substituted into the integrase gene in place of the present zinc finger. For instance, the segment coding for the DNA binding region of the human estrogen receptor gene may be substituted in place of the DNA binding region of the integrase in a packaging genome. Initially, specific integration would be tested by means of an in vitro integration system (Brown et al., *Cell* 29:347–356, 1987). To confirm that the specificity would be seen in vivo, this packaging genome is used to make infectious vector particles, and infection of and integration into estrogen-sensitive and estrogen-nonsensitive cells compared in culture.

Through use of this technique, incoming viral vectors may be directed to integrate into preselected sites on the target cell's genome, dictated by the genome-binding properties of site-specific DNA-binding protein segments spliced into the integrase genome. It will be understood by those skilled in the art that the integration site must, in fact, be receptive to the fingers of the modified integrase. For example, most cells are sensitive to glucocorticoids and hence their chromatin has sites for glucocorticoid receptors. Thus, for most cells, a modified integrase having a glucocorticoid receptor finger would be suitable to integrate the proviral vector construct at those glucocorticoid receptor-binding sites.

X. Production of Recombinant Retroviral Vectors in Transgenic Animals

Figure 21:
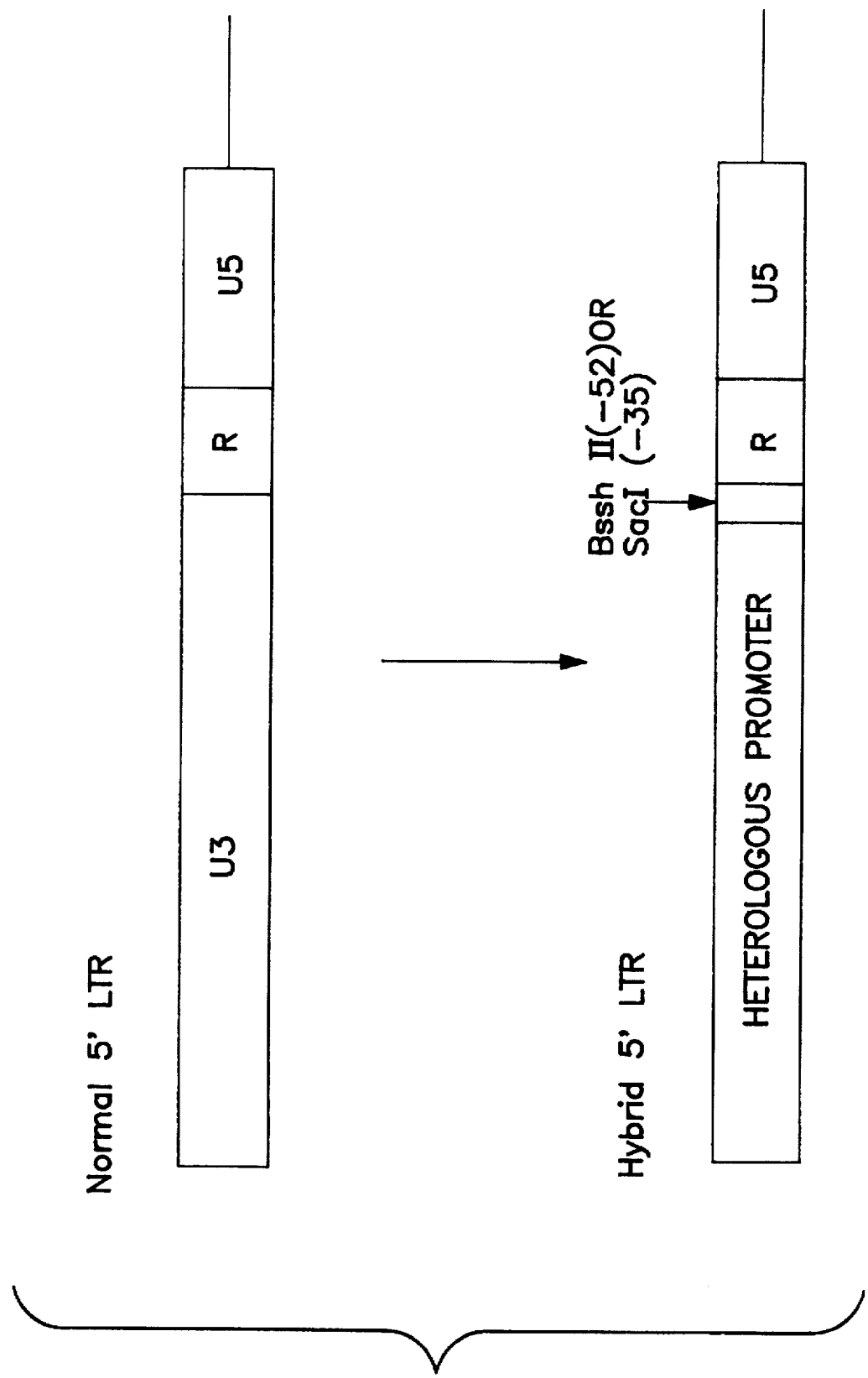
FIG. 21 depicts the substitution of U3 in a 5' LTR by a heterologous promoter/enhancer which can be fused to either the Sac I, Bssh II or other site in the region.
Figure 22:
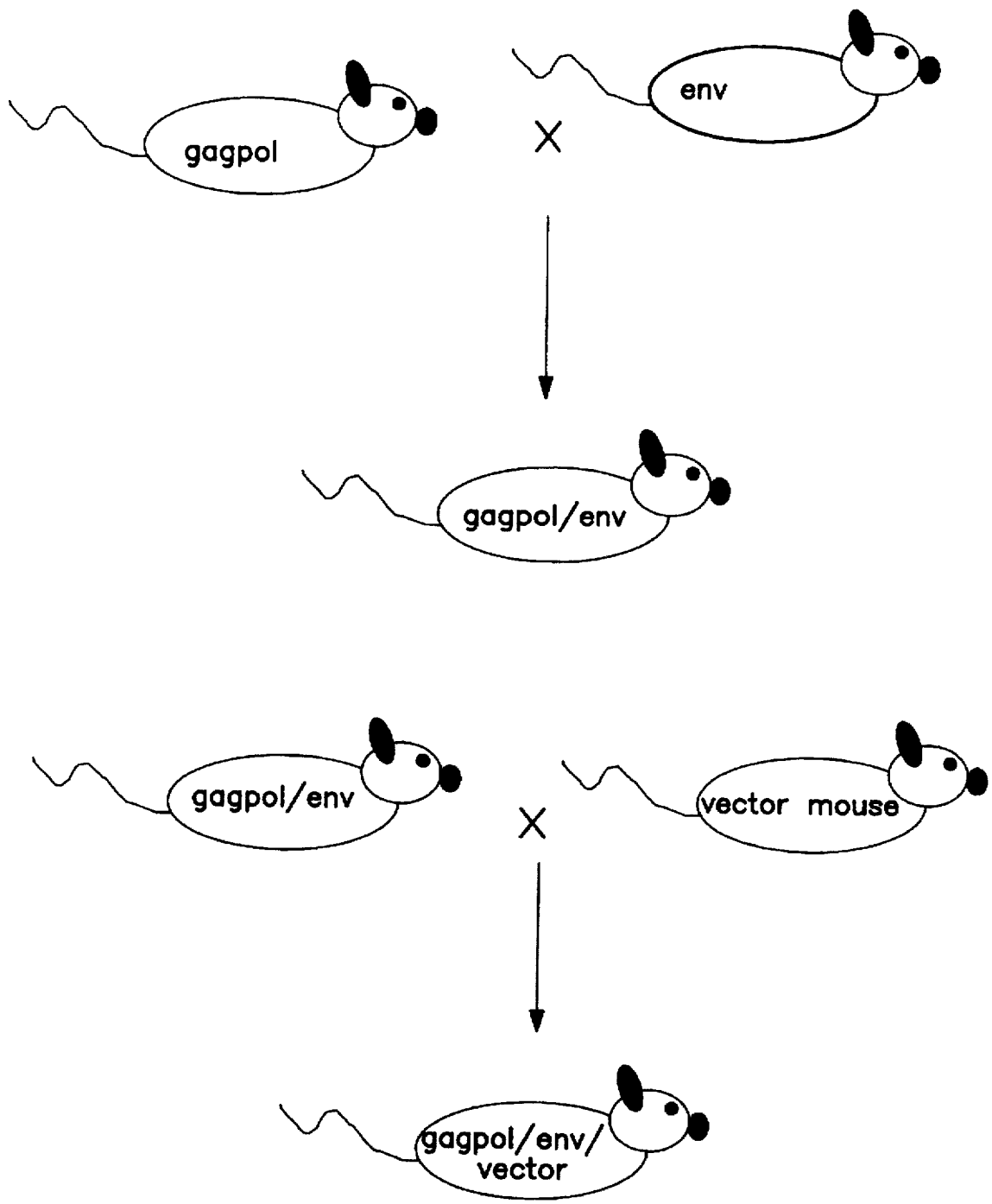
FIG. 22 illustrates a representative method for crossing transgenic mice expressing viral protein or vector RNA.

Two problems previously described with helper line generation of retroviral vectors are: (a) difficulty in generating large quantities of vectors; and (b) the current need to use permanent instead of primary cells to make vectors. These problems can be overcome with producer or packaging lines that are generated in transgenic animals. These animals would carry the packaging genomes and retroviral vector genomes. Current technology does not allow the generation of packaging cell lines and desired vector-producing lines in primary cells due to their limited life span. The current technology is such that extensive characterization is necessary, which eliminates the use of primary cells because of senescence. However, individual lines of transgenic animals can be generated by the methods provided herein which produce the packaging functions, such as gag, pol or env. These lines of animals are then characterized for expression in either the whole animal or targeted tissue through the selective use of housekeeping or tissue-specific promoters to transcribe the packaging functions. The vector to be delivered is also inserted into a line of transgenic animals with a tissue-specific or housekeeping promoter. As discussed above, the vector can be driven off such a promoter substituting for the U3 region of the 5' LTR (FIG. 21). This transgene could be inducible or ubiquitous in its expression. This vector, however, is not packaged. These lines of animals are then mated to the gag/pol/env animal and subsequent progeny produce packaged vector. The progeny, which are essentially identical, are characterized and offer an unlimited source of primary producing cells. Alternatively, primary cells making gag/pol and env and derived from transgenic animals can be infected or transfected in bulk with retrovirus vectors to make a primary cell producer line. Many different transgenic animals or insects could produce these vectors, such as mice, rats, chickens, swine, rabbits, cows, sheep, fish and flies. The vector and packaging genomes would be tailored for species infection specificity and tissue-specific expression through the use of tissue-specific promoters and different envelope proteins. An example of such a procedure is illustrated in FIG. 22.

Although the following examples of transgenic production of primary packaging lines are described only for mice, these procedures can be extended to other species by those skilled in the art. These transgenic animals may be produced by microinjection or gene transfer techniques. Given the homology to MLV sequences in mice genome, the final preferred animals would not be mice.

EXAMPLE 10

Production of Gag/Pol Proteins Using Housekeeping Promoters for Ubiquitous Expression in Transgenic Animals An example of a well-characterized housekeeping promoter is the HPRT promoter. HPRT is a purine salvage enzyme which expresses in all tissues. (See Patel et al., *Mol. Cell Biol.* 6:393–403, 1986 and Melton et al., *Proc. Natl. Acad. Sci.* 81:2147–2151, 1984). This promoter is inserted in front of various gag/pol fragments (e.g., Bal I/Sca I; Aat II/Sca I; Pst I/Sca I of MoMLV; see *RNA Tumor Viruses* 2, Cold Spring Harbor Laboratory, 1985) that are cloned in Bluescript plasmids (Strategene, Inc.) using recombinant DNA techniques (see Maniatis et al., *Molecular Cloning: A Laboratory Manual*, Cold Spring Harbor, 1982). The resulting plasmids are purified (Maniatis et al., op. cit.) and the relevant genetic information isolated using Geneclean (Bio 101) or electroelution (see Hogan et al. (eds.), *Manipulating the Mouse Embryo: A Laboratory Manual*, Cold Spring Harbor, 1986).

These fully characterized DNAs are microinjected in the pronucleus of fertilized mouse ova at a concentration of 2 ug/ml. Live-born mice are screened by tail blot analyses (see Hogan et al., op. cit.). Transgenic-positive animals are characterized for expression levels of gag-pol proteins by immunoprecipitation of radiolabeled primary cells, such as fibroblast (see Harlow et al. (eds.), *Antibodies: A Laboratory Manual*, Cold Spring Harbor, 1988). Animals then bred to homozygosity for establishment of animal lines that produce characterized levels of gag-pol.

EXAMPLE 11

Production of env Proteins/Hybrid Envelope Proteins Using Housekeeping Promoters for Ubiquitous Expression in Transgenic Animals This example utilizes the HPRT promoter for expression of either envelope or hybrid envelope proteins. The envelope proteins can be from any retrovirus that is capable of complementing the relevant gag-pol, in this case that of MLV. Examples are ecotropic MLV, amphotrophic MLV, xenotropic MLV, polytropic MLV, or hybrid envelopes. As above, the envelope gene is cloned behind the HPRT promoter using recombinant DNA techniques (see Maniatis et al., op. cit.). The resulting "minigene" is isolated (see Hogan et al., op. cit.), and expression of envelope protein is determined (Harlow et al., op. cit.). The transgenic envelope animals are bred to homozygosity to establish a well-characterized envelope animal.

EXAMPLE 12

Production of gag-pol-env Animals Using Housekeeping Promoters for Ubiquitous Expression in Transgenic Animals This uses the well-characterized gag-pol animals, as well as the animals for the establishment of a permanent gag-pol/envelope animal line. This involves breeding to homozygosity and the establishment of a well-characterized line. These lines are then used to establish primary mouse embryo lines that can be used for packaging vectors in tissue culture. Furthermore, animals containing the retroviral vector are bred into this line.

EXAMPLE 13

Production of Tissue-Specific Expression of gag-pol-env or Hybrid Envelope in Transgenic Animals This example illustrates high level expression of the gag/pol, envelope, or hybrid envelope in specific tissues, such as T-cells. This involves the use of CD2 sequences (see Lang et al., *EMBO J.* 7:1675–1682, 1988) that give position and copy number independence. The 1.5 kb Bam HI/Hind III fragment from the CD2 gene is inserted in front of gag-pol, envelope, or hybrid envelope fragments using recombinant DNA techniques. These genes are inserted into fertilized mouse ova by microinjection. Transgenic animals are characterized as before. Expression in T-cells is established, and animals are bred to homozygosity to establish well-characterized lines of transgenic animals. Gag-pol animals are mated to envelope animals to establish gag-pol-env animals expressing only in T-cells. The T-cells of these animals are then a source for T-cells capable of packaging retroviral vectors. Again, vector animals can be bred into these gag-pol-env animals to establish T-cells expressing the vector.

This technique allows the use of other tissue-specific promoters, such as milk-specific (whey), pancreatic (insulin or elastase), or neuronal (myelin basic protein) promoters. Through the use of promoters, such as milk-specific promoters, recombinant retroviruses may be isolated directly from the biological fluid of the progeny.

EXAMPLE 14

Figure 20:
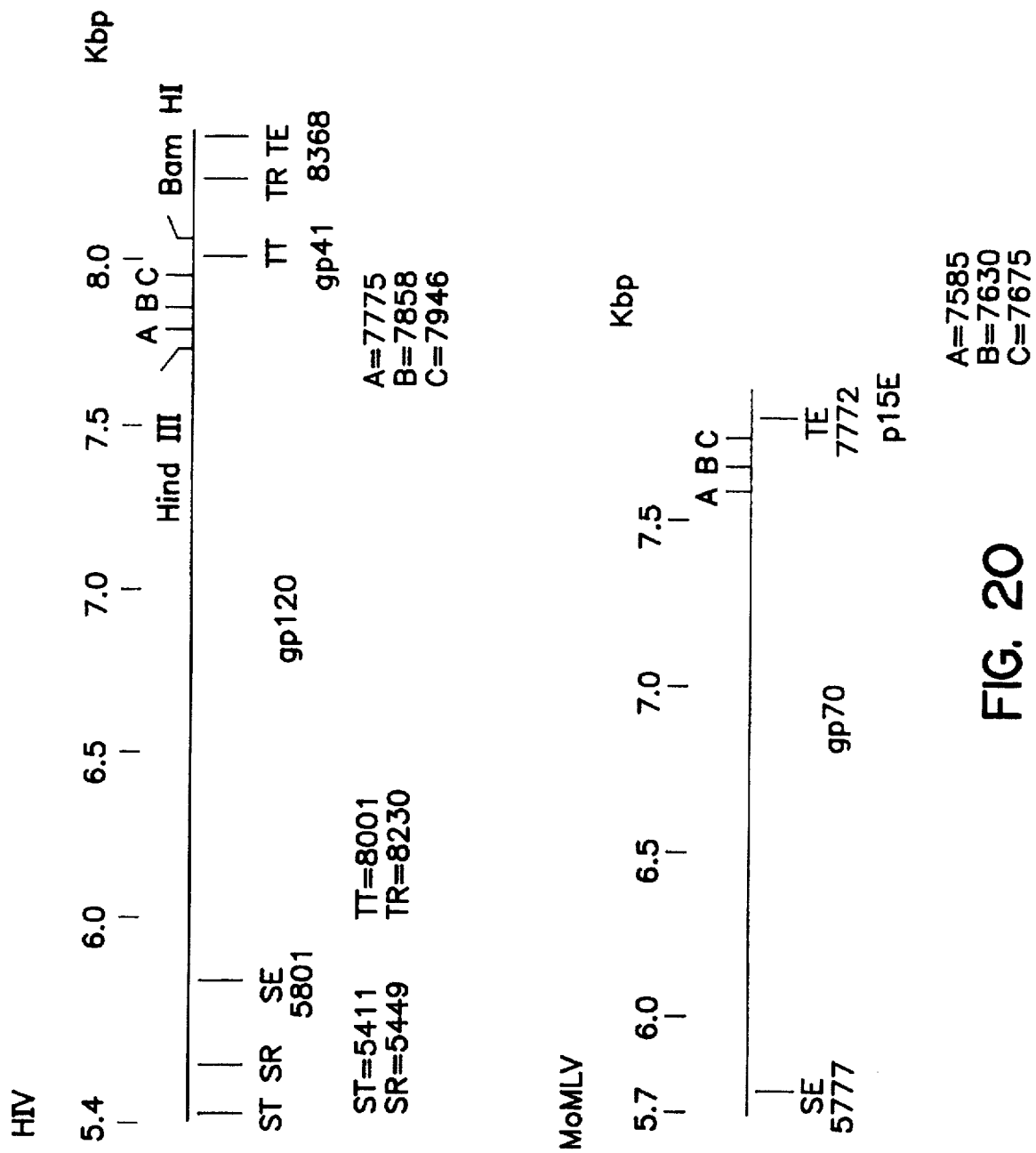
FIG. 20 depicts three sites of fusion of HIV env and MoMLV env after site-directed mutagenesis. The joint at the extracellular margin of the transmembrane region is designated as A, while B and C indicate locations of joints at the middle of the transmembrane region and cytoplasmic margin, respectively. The numbering is according to nucleotide numbers (*RNA Tumor Viruses*, Vol. II, Cold Spring Harbor, 1985). ST, SR, SE are the starts of tat, rev and env while TT, TR, and TE are the corresponding termination sites.

Production of Either Housekeeping or Tissue-Specific Retroviral Vectors in Transgenic Animals The insertion of retroviruses or retroviral vectors into the germ line of transgenic animals results in little or no expression. This effect, described by Jaenisch (see Jahner et al., *Nature* 298:623–628, 1982), is attributed to methylation of 5' retroviral LTR sequences. This technique would overcome the methylation effect by substituting either a housekeeping or tissue-specific promoter to express the retroviral vector/retrovirus. The U3 region of the 5' LTR, which contains the enhancer elements, is replaced with regulatory sequences from housekeeping or tissue-specific promoters (see FIG. 20). The 3' LTR is fully retained, as it contains sequences necessary for polyadenylation of the viral RNA and integration. As the result of unique properties of retroviral replication, the U3 region of the 5' LTR of the integrated provirus is generated by the U3 region of the 3' LTR of the infecting virus. Hence, the 3' is necessary, while the 5' U3 is dispensable. Substitution of the 5' LTR U3 sequences with promoters and insertion into the germ line of transgenic animals results in lines of animals capable of producing retroviral vector transcripts. These animals would then be mated to gag-pol-env animals to generate retroviral-producing animals (see FIG. 22).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for treating human lymphocytes ex vivo to render said lymphocytes susceptible to being diminished or eliminated, comprising:
   a) removing human lymphocytes from the peripheral blood of a human; and
   b) infecting the lymphocytes ex vivo with a replication defective recombinant retrovirus to produce infected lymphocytes, said recombinant retrovirus comprising a recombinant gene operably linked to a promoter for expression in said lymphocytes, said gene encoding a protein which is not normally expressed in said lymphocytes and which converts a prodrug into a cytotoxic agent, whereby when said infected lymphocytes are exposed to said prodrug, said protein expressed therein converts said prodrug to a cytotoxic agent, killing said lymphocytes.

2. The method of claim 1 wherein said prodrug is purine-based or pyrimidine-based.

3. The method of claim 2 wherein said prodrug is purine-based.

4. The method of claim 2 wherein said prodrug is pyrimidine-based.

5. The method of claim 2 wherein said protein processes a purine-based or pyrimidine-based drug with little or no cytotoxicity into a cytotoxic compound.

6. The method of claim 5 wherein said protein is a nucleoside kinase.

7. The method of claim 6 wherein said nucleoside kinase is thymidine kinase.

8. The method of claim 7 wherein said thymidine kinase is herpes simplex virus thymidine kinase.

9. The method of claim 1 wherein said protein catalyzes the metabolism of a purine-based or pyrimidine-based drug.

10. The method of claim 9 wherein said protein is guanine phosphoribosyl transferase.

11. The method of claim 9 wherein said protein causes phosphorylation, ribosylation, or phosphorylribosylation of said drug.

12. The method of claim 9 wherein said purine-based or pyrimidine-based drug is acyclovir, AZT, ddC, FIAU, FIAC or DHPG.

13. A method of infecting a human peripheral blood lymphocyte with a recombinant retrovirus comprising:
   a) infecting said lymphocyte in vitro with a replication defective recombinant retrovirus to produce an infected lymphocyte, said recombinant retrovirus comprising a recombinant gene operably linked to a promoter for expression in said lymphocyte, said gene encoding a protein which is not normally expressed in said lymphocyte and which converts a prodrug into an agent that is cytotoxic to said lymphocyte.

14. The method of claim 13 wherein said prodrug is purine-based or pyrimidine-based.

15. The method of claim 14 wherein said purine-based or pyrimidine-based drug is acyclovir, AZT, ddc, FIAU, FIAC, DHPG.

16. The method of claim 13 wherein said protein is a nucleoside kinase.

17. The method of claim 16 wherein said nucleoside kinase is herpes simplex thymidine kinase.

18. The method of claim 13 wherein said protein is *E. coli* guanine phosphoribosyl transferase.

19. A transduced human peripheral blood lymphocyte, said lymphocyte transduced by a process comprising:
   a) infecting a human peripheral blood lymphocyte in vitro with a replication defective recombinant retrovirus to produce an infected lymphocyte, said recombinant retrovirus comprising a recombinant gene operably linked to a promoter for expression in said lymphocyte, said gene encoding a protein which is not normally expressed in said lymphocyte and which converts a prodrug into an agent that is cytotoxic to said lymphocyte.

20. The lymphocyte of claim 19 wherein said prodrug is purine-based or pyrimidine-based.

21. The lymphocyte of claim 20 wherein said purine-based or pyrimidine-based drug is acyclovir, AZT, ddc, FIAU, FIAC, DHPG.

22. The lymphocyte of claim 19 wherein said protein is a nucleoside kinase.

23. The lymphocyte of claim 22 wherein said nucleoside kinase is herpes simplex thymidine kinase.

24. The lymphocyte of claim 19 wherein said protein is *E. coli* guanine phosphoribosyl transferase.

* * * * *

UNITED STATES PATENT AND TRADEMARK OFFICE
CERTIFICATE OF CORRECTION

PATENT NO. : 5,691,177

DATED : November 25, 1997

INVENTOR(S) : Gruber et al.

It is certified that error appears in the above-identified patent and that said Letters Patent is hereby corrected as shown below:

ON THE TITLE PAGE:

Item [19], under United States Patent, delete "Guber" and substitute therefor --Gruber--.

Item [76], column 1, after Harry E., delete "Guber" and substitute therefor --Gruber--.

column 2, publication Bachmann, et al., delete "venue" and substitute therefor --versus--

At Col. 8, line 59, delete "this" and substitute therefor --tathis--.

At Col. 15, line 14, after the word "return" delete --.--.

At Col. 15, line 48, before the word "such" add --(--.

At Col. 20, line 6, delete "mucleotide" and substitute therefor --nucleotide--.

At Col. 26, Table 1, line 15, delete "HL50" and substitute therefor --HL60--.

At Col. 26, Table 1, delete all "KTVIH5NeO" and substitute therefor --KTVIH5Neo--

At Col. 26, Table 1, line 23, delete "KTVIHAX    +    0.05".

Signed and Sealed this

Twenty-ninth Day of September, 1998

Attest:

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,691,177
DATED : November 25, 1997
INVENTOR(S) : Gruber et al.

It is certified that error appears in the above-indentified patent and that said Letters Patent is hereby corrected as shown below:

At Col. 26, Table 1, line 27 delete ")5" and substitute therefor --0.5--.

At Col, 28, line 34, delete "immuno-logically" and substitute therefor --immunologically--.

At Col, 28, line 58, delete "dNTP'as" and substitute therefor --dNTPs--

At Col. 31, line 54, delete "23" and substitute therefor --13--.

Figures 1, 4A:
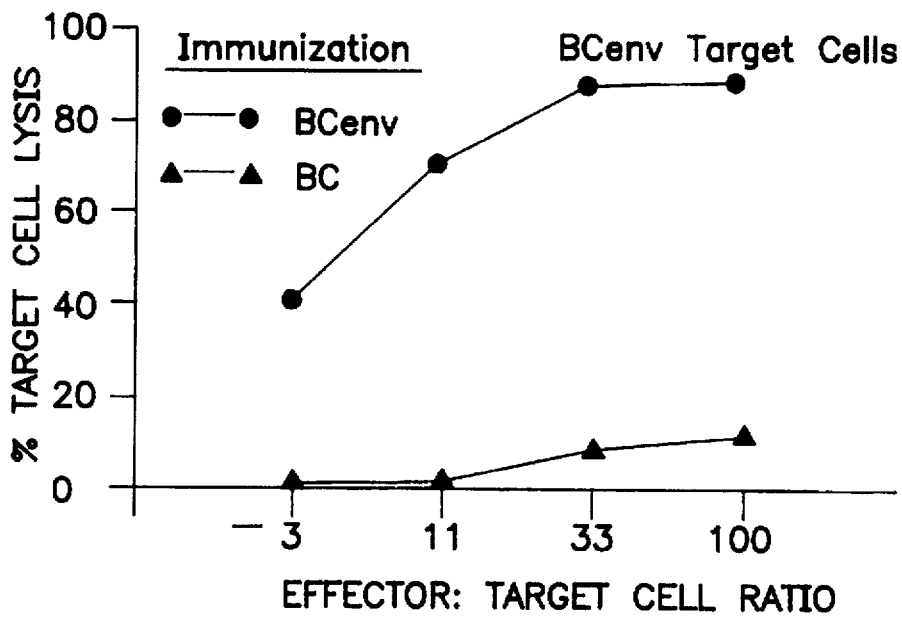
Figures 2, 4A:
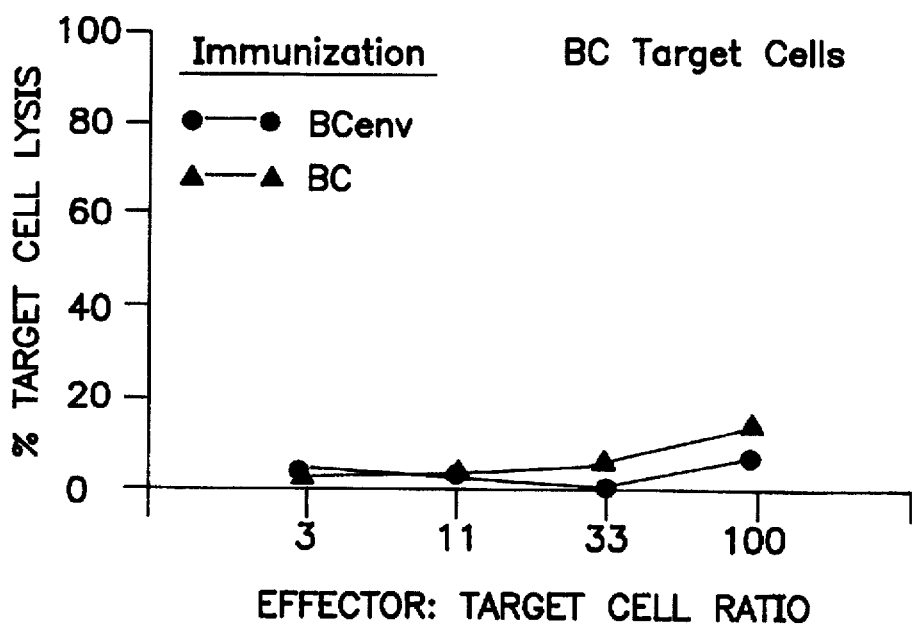
Figure 4B:
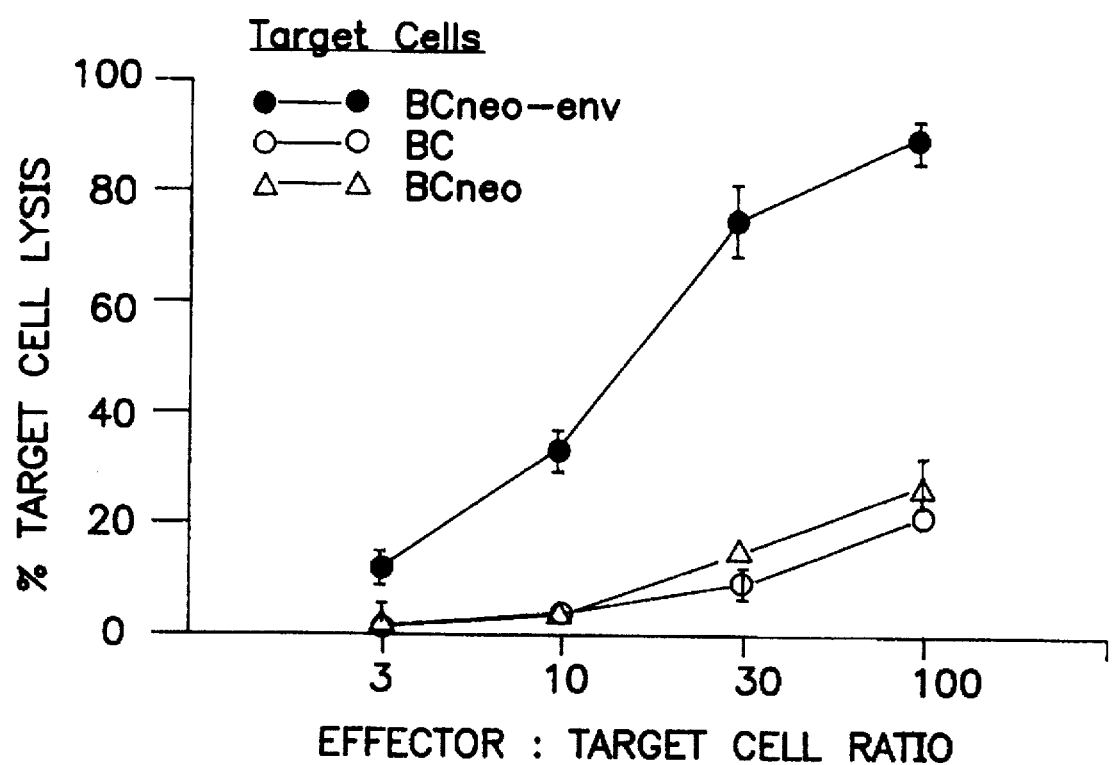
FIG. 4B illustrates the specificity of the CTL for HIV envelope antigens.
Figure 4C:
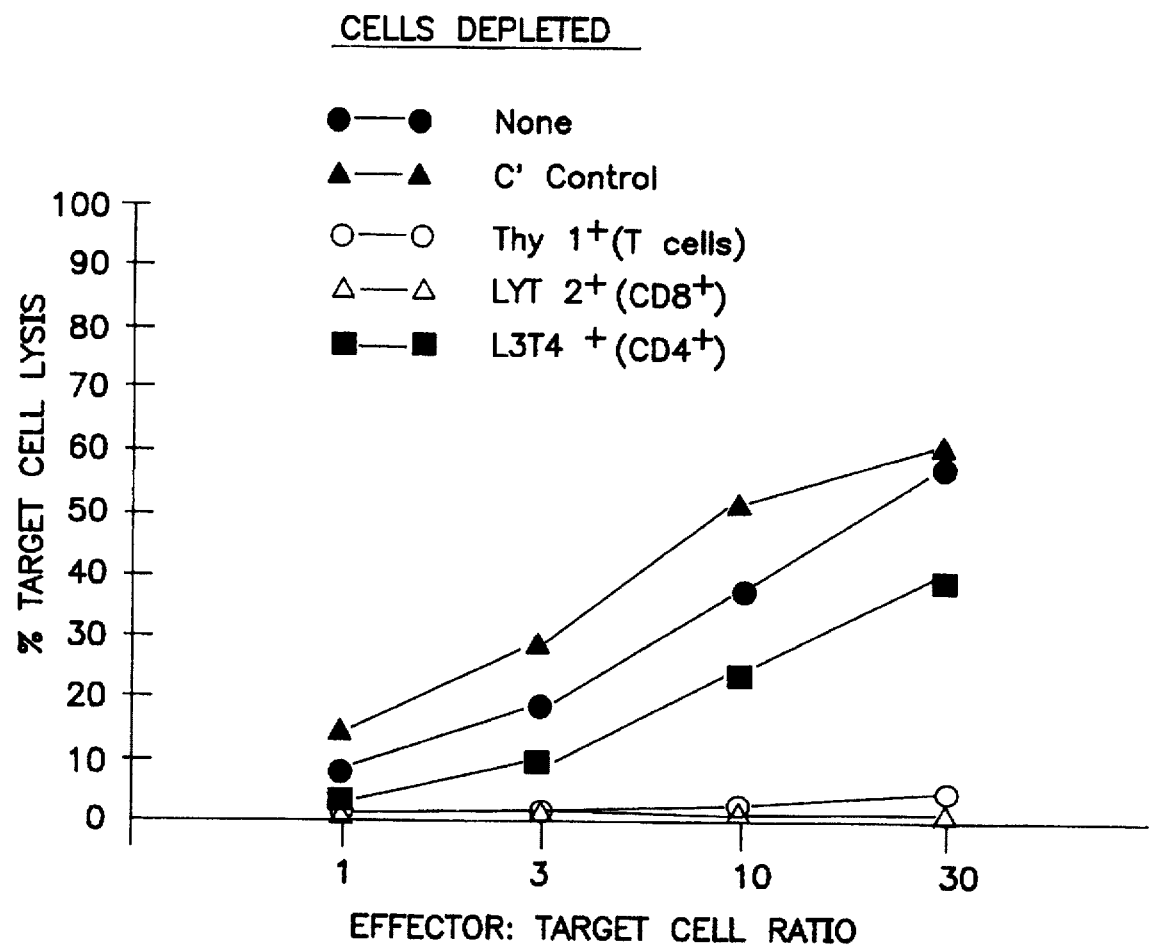
FIG. 4C demonstrates the phenotype of the effector cell population generated in the experimental protocol in FIG. 3. The effector cell population is that of an L3T4$^-$lyt2$^+$ (CD4$^-$ CD8$^+$) T lymphocyte.
Figure 4D:
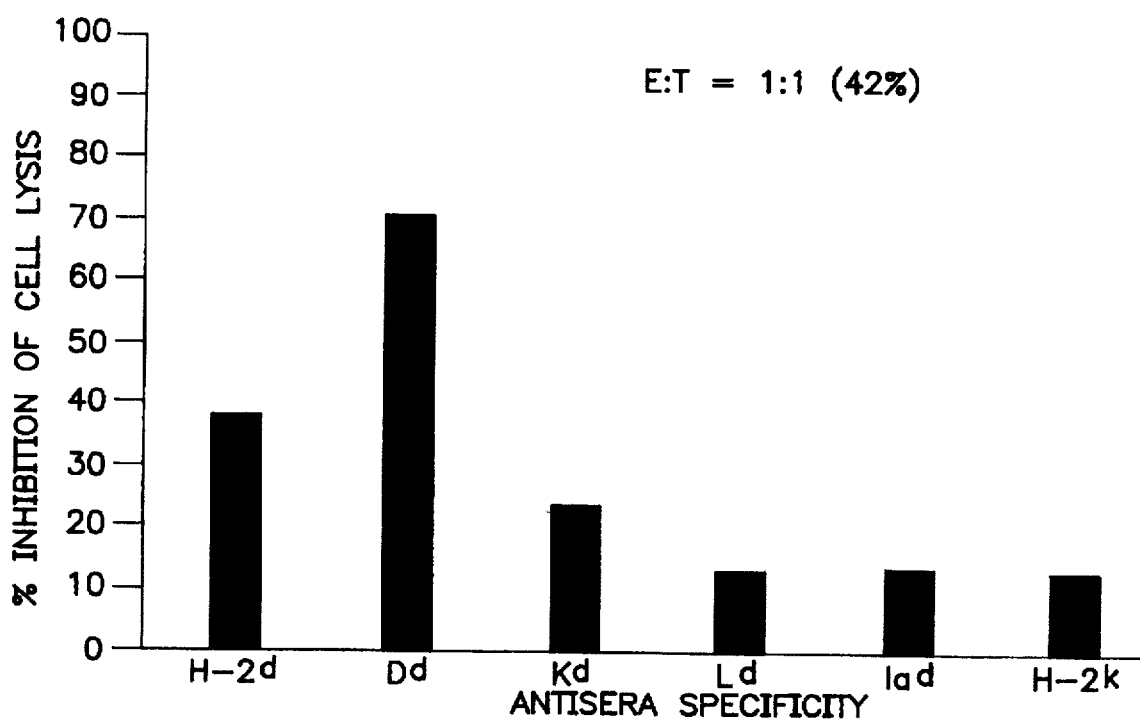
FIG. 4D illustrates the MHC restriction requirements for the Balb/c anti-BCenv CTL response.
Figure 4E:
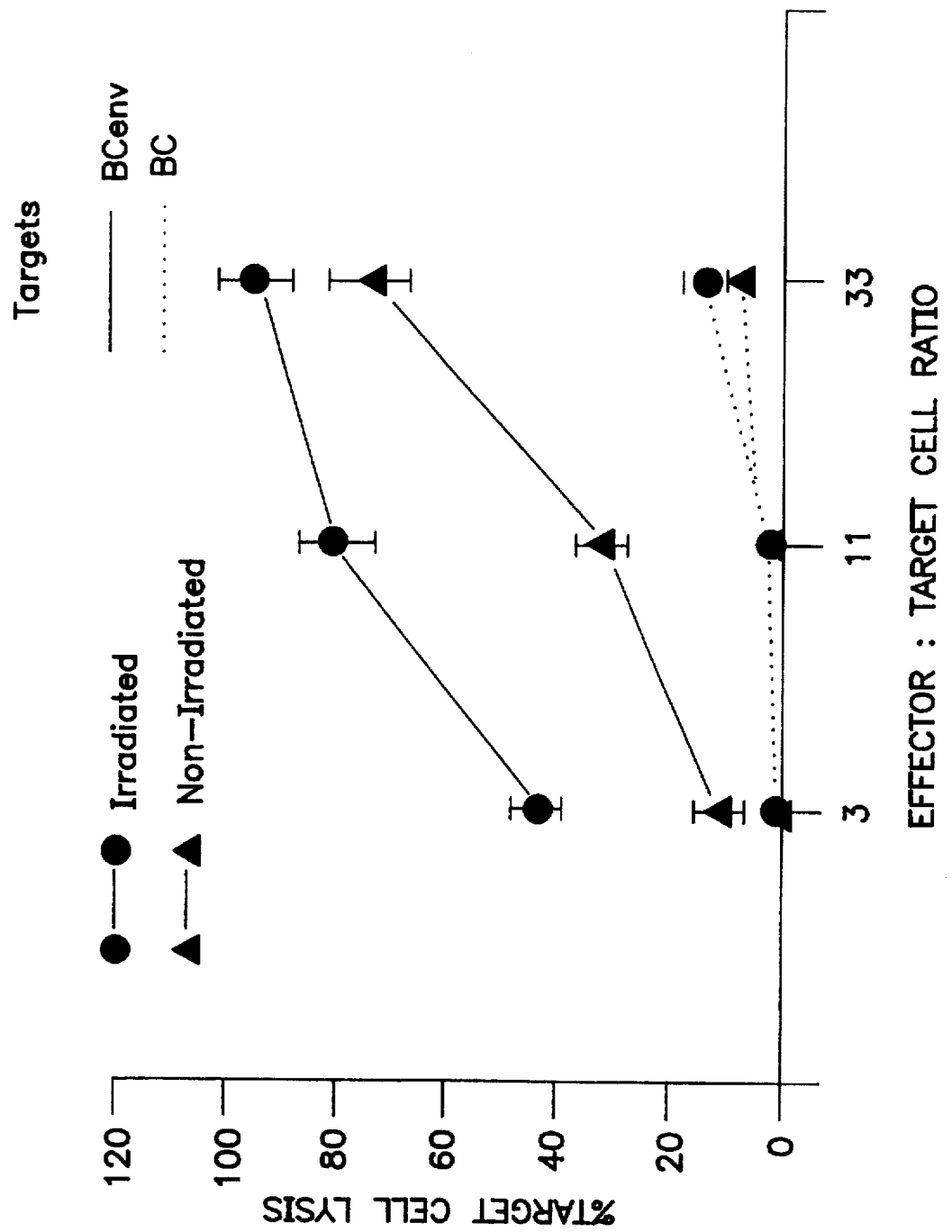
FIG. 4E demonstrates that CTL can be induced in vivo by irradiated nonproliferating stimulator cells.

Sheet 4 of 27, Fig. 4A-1, delete "-3" and substitute --3--.

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

It is certified that error appears in the above-identified patent and that said Letters Patent is hereby corrected as shown below:

In Figs. 4G-1 and 4G-2, please delete "B10.02" and B602F1" and substitute therefor --B10.D2-- and --B6D2F1-- respectively as shown below:

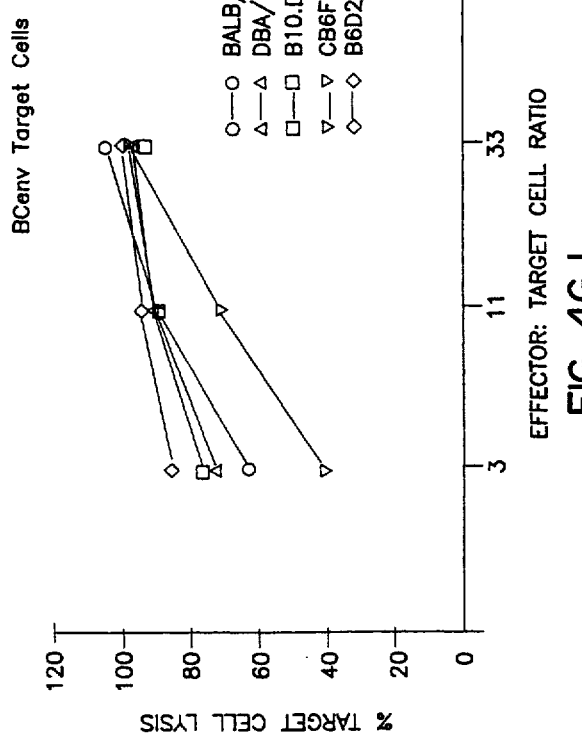

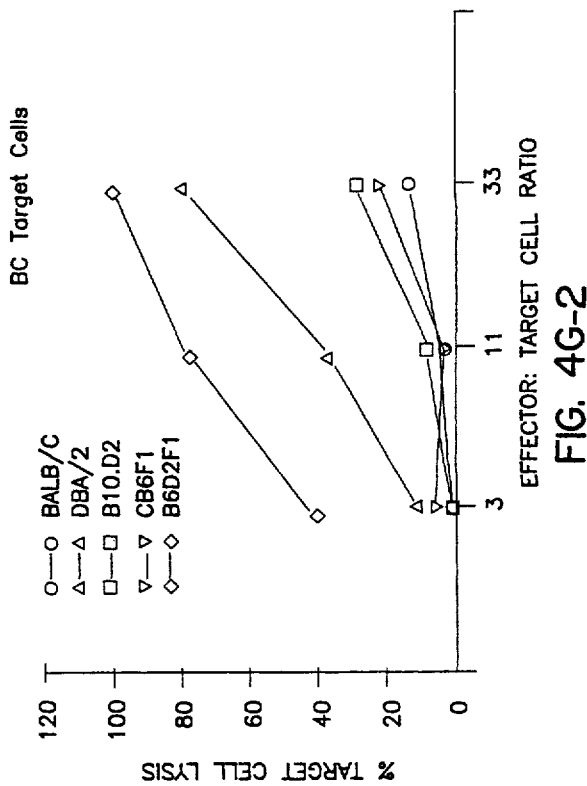

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

It is certified that error appears in the above-identified patent and that said Letters Patent is hereby corrected as shown below:

In the drawings, Sheet 4, Fig. 4A-1, a "I" Bar, indicating range should appear across the point at E:T cell ratio "11", as shown below:

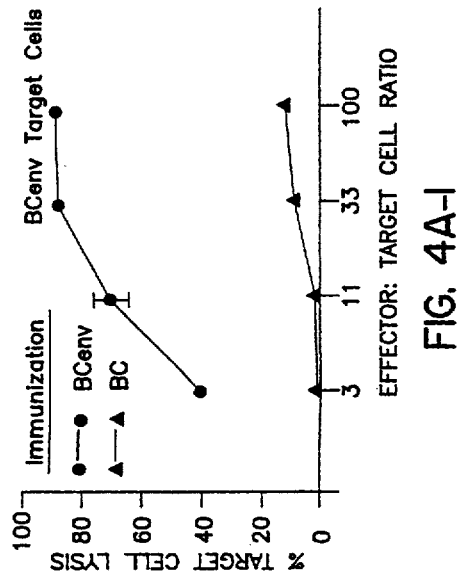

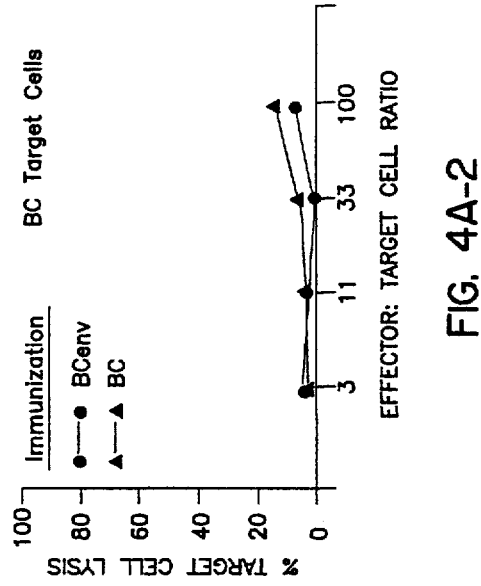

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

It is certified that error appears in the above-identified patent and that said Letters Patent is hereby corrected as shown below:

In Fig. 5, delete "pro" and substitute therefor --Pro-- as indicated below:

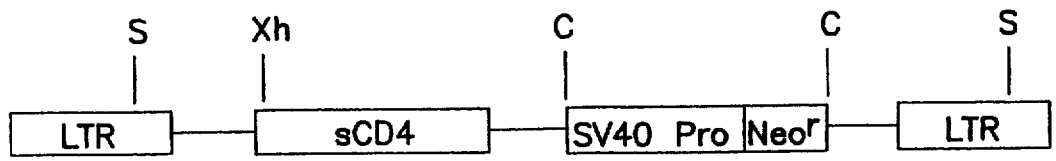

FIG. 5

UNITED STATES PATENT AND TRADEMARK OFFICE
CERTIFICATE OF CORRECTION

PATENT NO. : 5,691,177                                Page 6 of 11
DATED     : November 25, 1997
INVENTOR(S) : Gruber, et al.

It is certified that error appears in the above-identified patent and that said Letters Patent is hereby corrected as shown below:

In the drawings, Sheet 6, Fig. 4C, all a bracket ("-") above and below the "▲" at the cell ratio "3" and above and below the "■" at cell ratios 3, 10 and 30, as shown below:

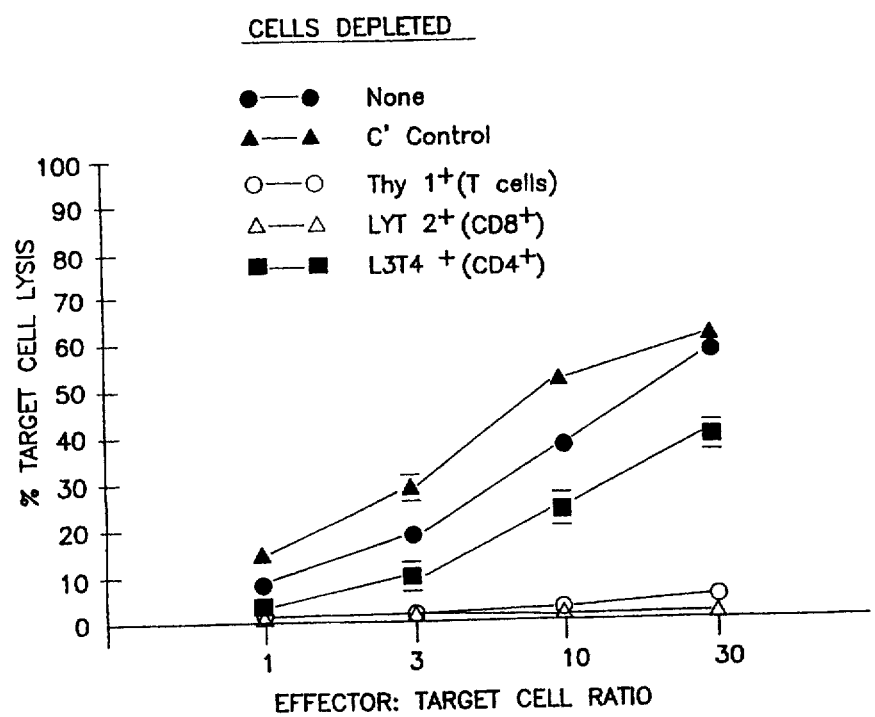

FIG. 4C

UNITED STATES PATENT AND TRADEMARK OFFICE
CERTIFICATE OF CORRECTION

PATENT NO.  : 5,691,177                     Page 7 of 11
DATED       : November 25, 1997
INVENTOR(S) : Gruber, et al.

Figure 7:
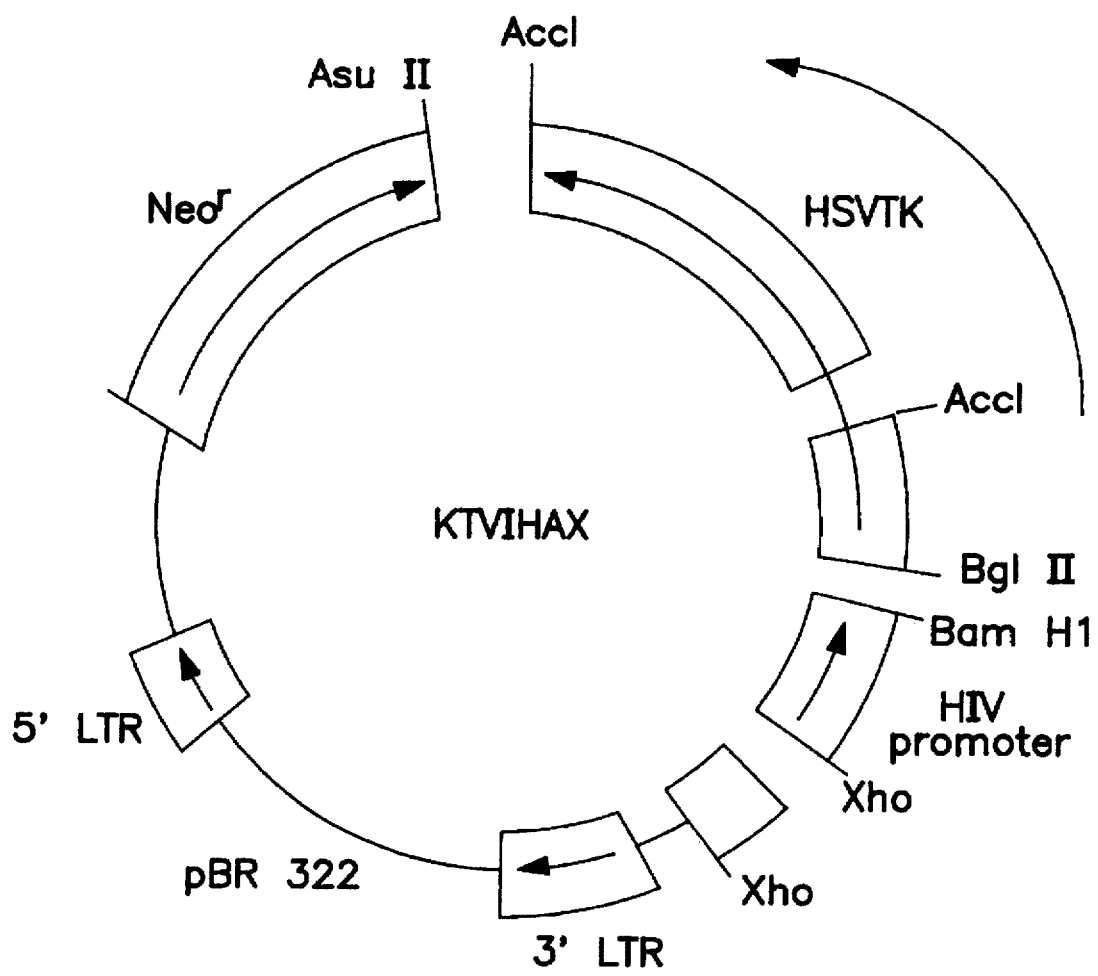
FIG. 7 illustrates the construction of the plasmid carrying the vector KTVIHAX.

It is certified that error appears in the above-identified patent and that said Letters Patent is hereby corrected as shown below:

In Fig. 7, delete the lowest "Xho" and substitue therefor --XhoI-- as shown below:

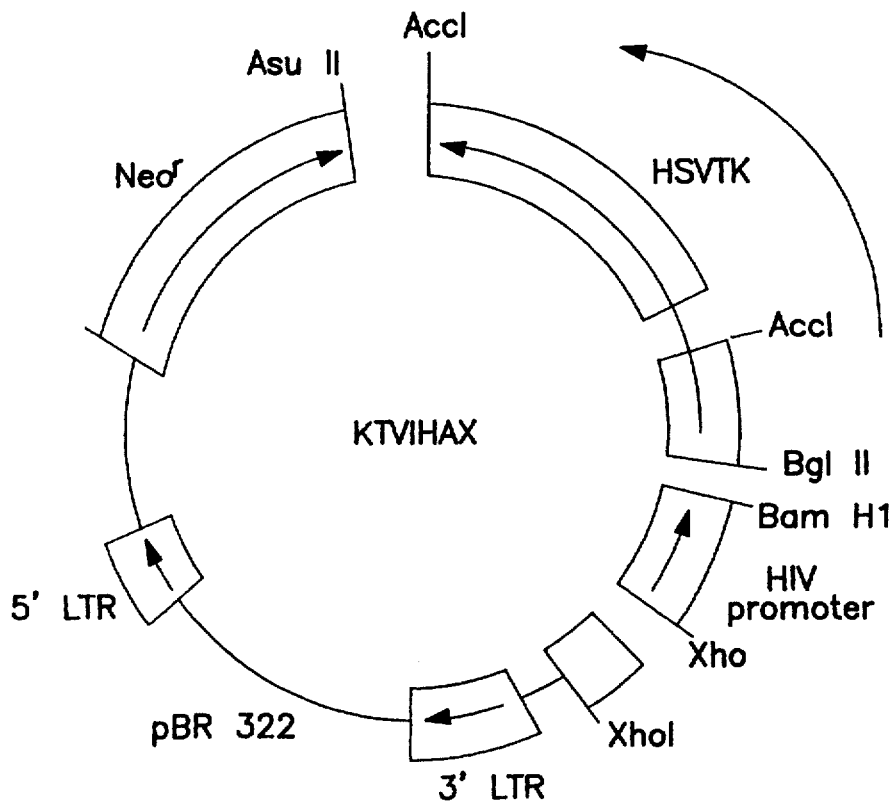

FIG. 7

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

Figures 1, 4F:
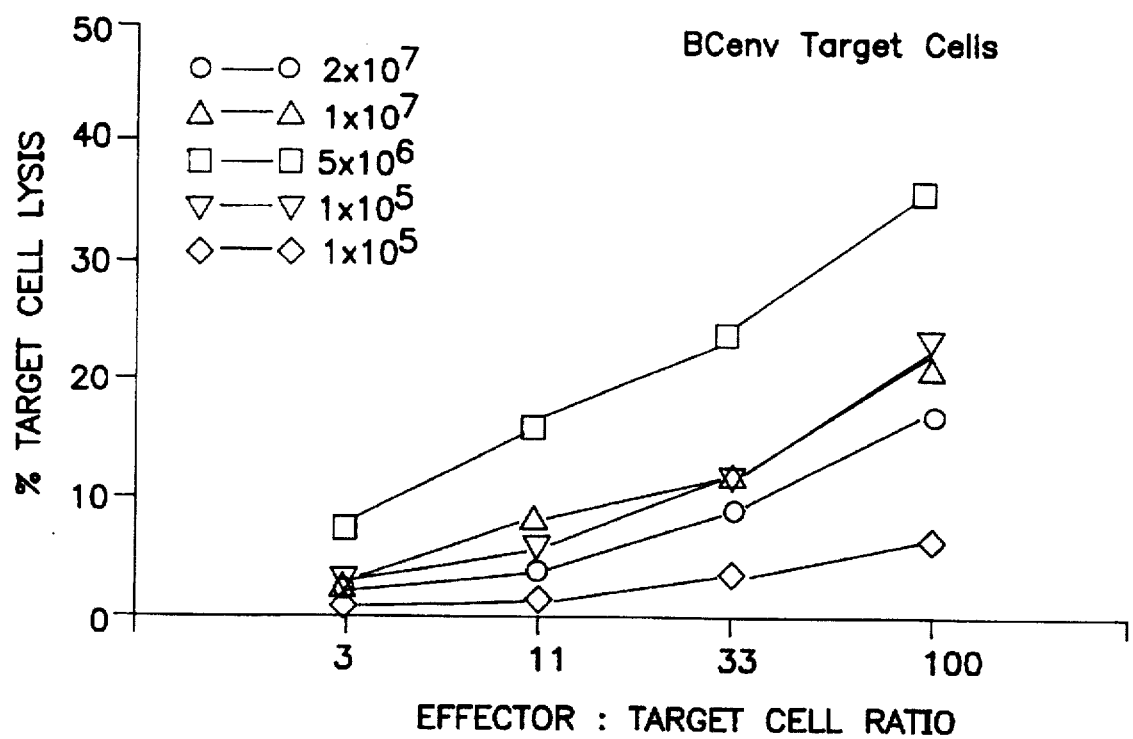
Figures 2, 4F:
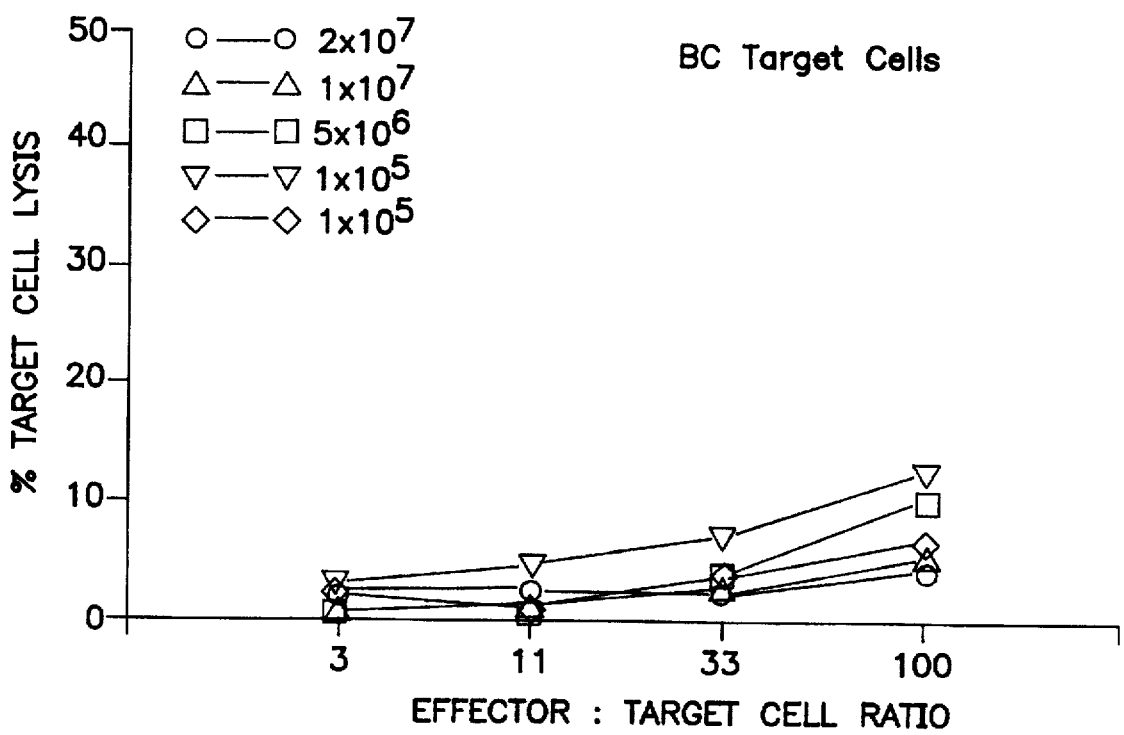
Figures 1, 4G:
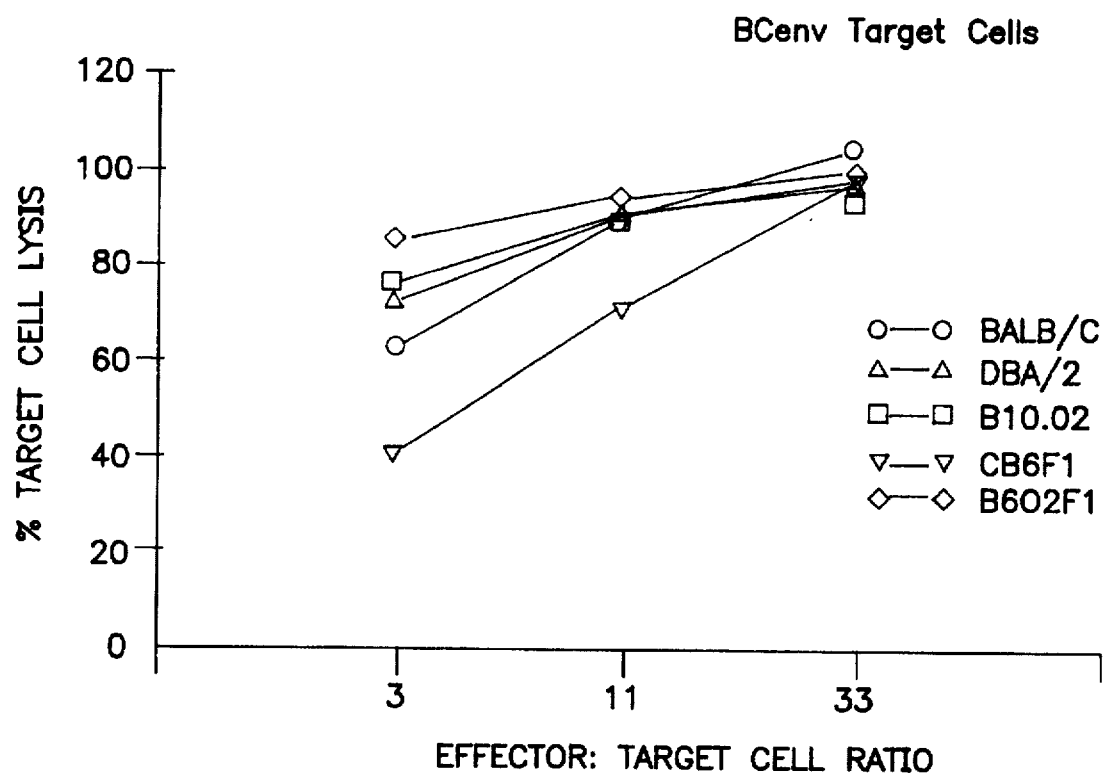
Figures 2, 4G:
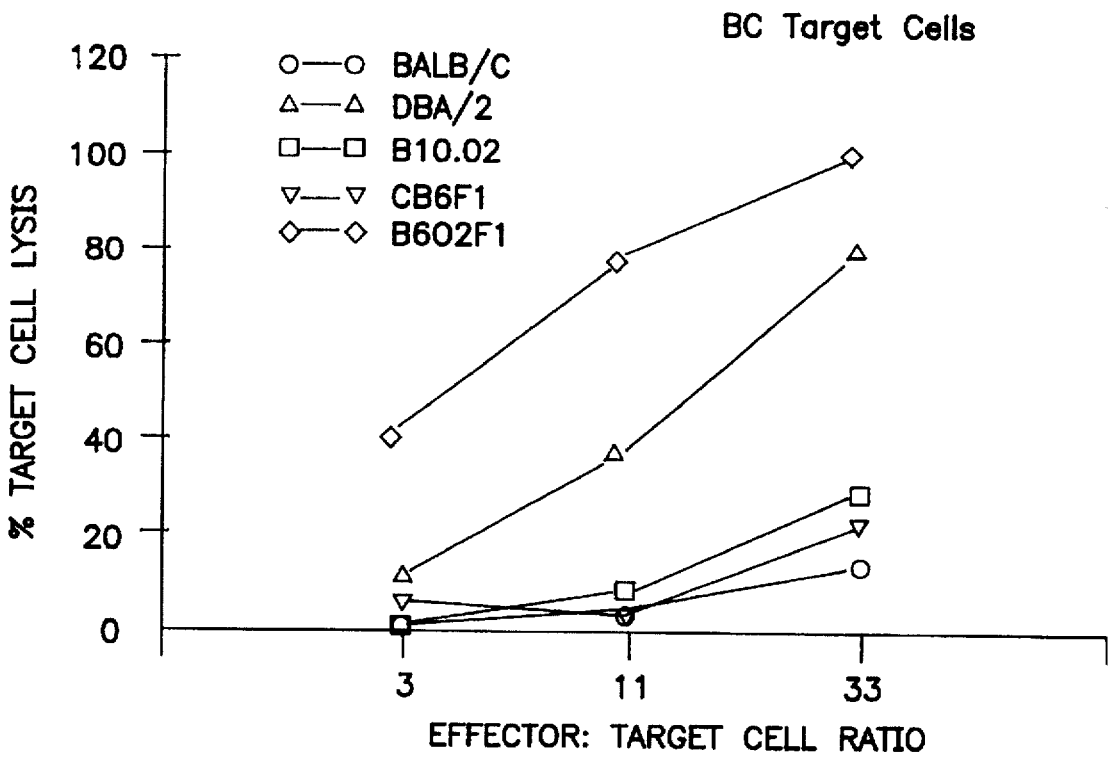

It is certified that error appears in the above-identified patent and that said Letters Patent is hereby corrected as shown below:

In the drawings, Sheet 9, Figs. 4F-1 and 4F-2, across from "∇--∇" delete "$1 \times 10^5$" and substitute therefor --$1 \times 10^6$--, as shown below:

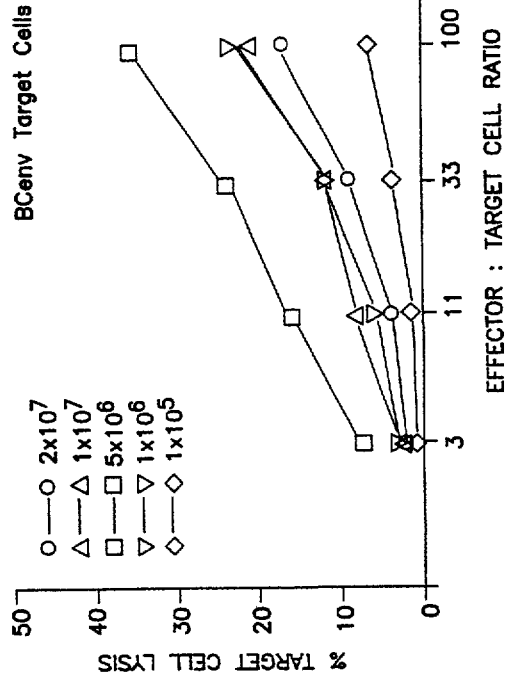

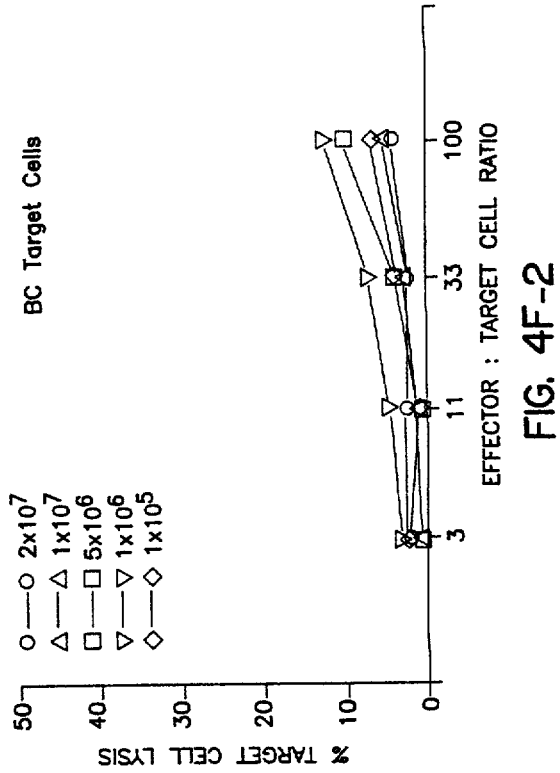

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

It is certified that error appears in the above-identified patent and that said Letters Patent is hereby corrected as shown below:

In Fig. 14, at the right hand side delete "0.7KB" and substitute therefor --0.7kb--.

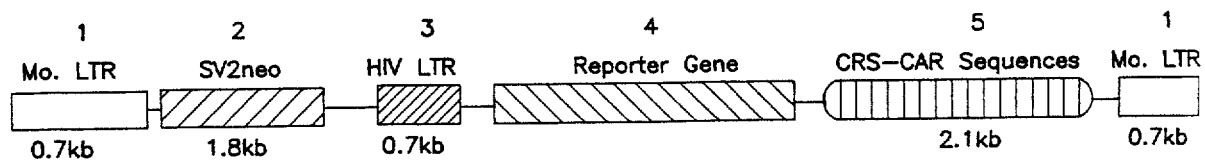

FIG. 14

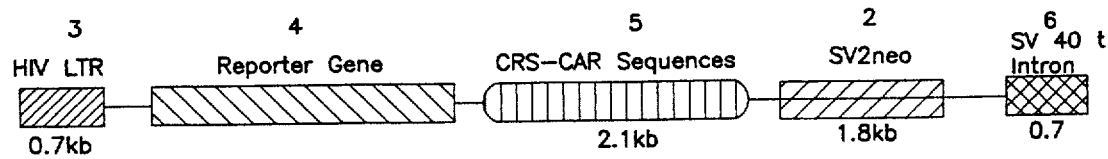

FIG. 15

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

Page 10 of 11

It is certified that error appears in the above-identified patent and that said Letters Patent is hereby corrected as shown below:

In Fig. 16, please adjust the days on the x axis as indicated below:

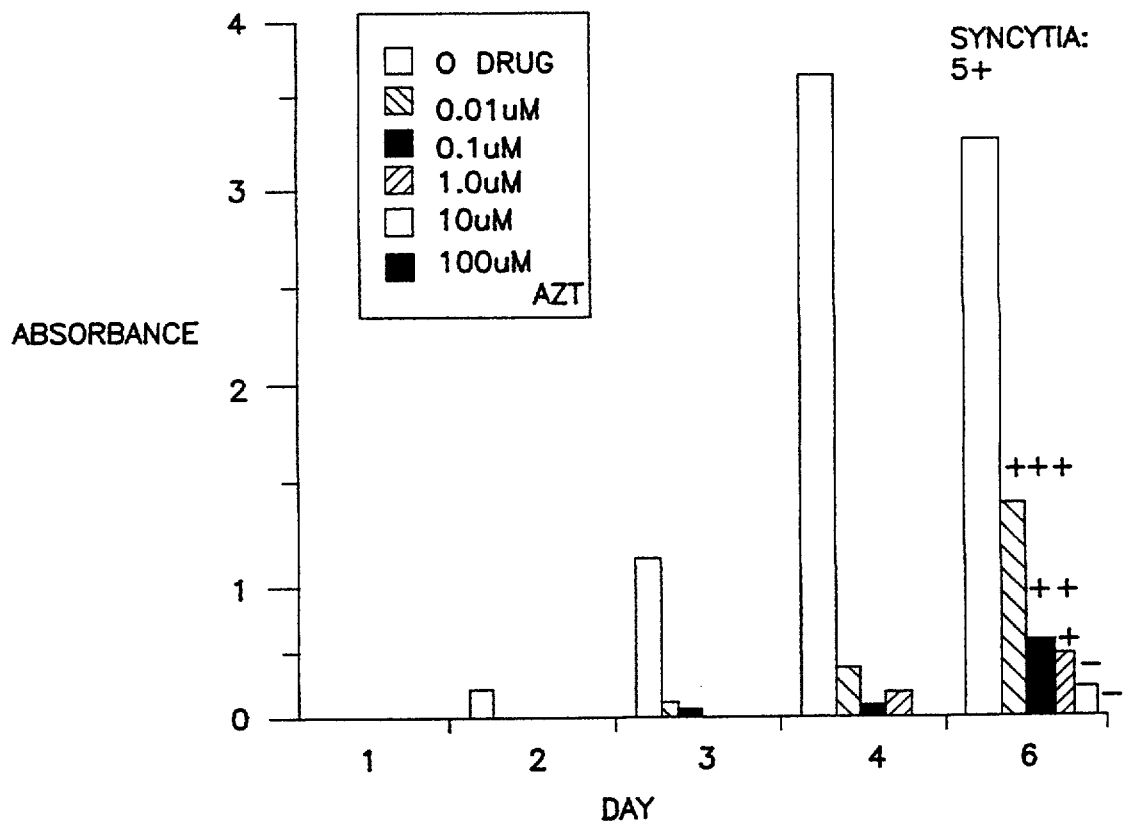

FIG. 16

UNITED STATES PATENT AND TRADEMARK OFFICE
CERTIFICATE OF CORRECTION

PATENT NO. : 5,691,177

DATED : November 25, 1997

INVENTOR(S) : Gruber, et al.

It is certified that error appears in the above-identified patent and that said Letters Patent is hereby corrected as shown below:

In Fig. 19, in the bottom vector, delete "phlea" and substitute therefor --phleo--.

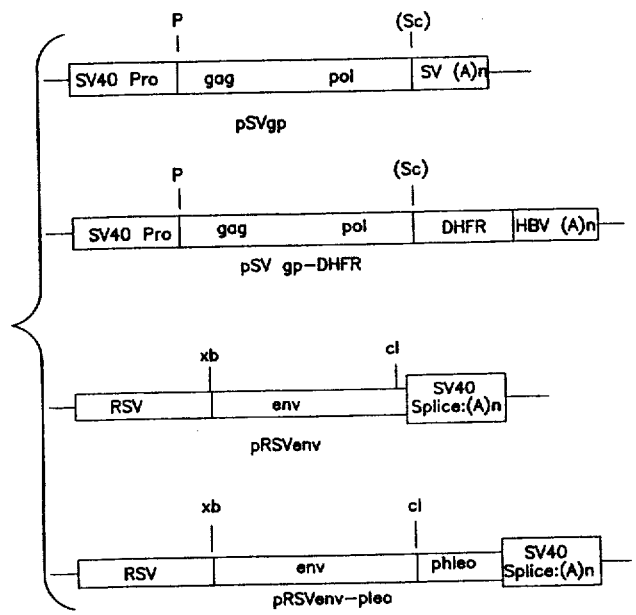

FIG. 19

UNITED STATES PATENT AND TRADEMARK OFFICE
CERTIFICATE OF CORRECTION

PATENT NO. : 5,691,177
DATED : November 25, 1997
INVENTOR(S) : Gruber et al.

It is certified that error appears in the above-identified patent and that said Letters Patent is hereby corrected as shown below:

At col. 42, lines 64 and 65, between "FIAC," and "DHPG" insert --or--.

At col. 44, line 5, between "FIAC," and "DHPG" insert --or--.

Signed and Sealed this

Twenty-second Day of May, 2001

Attest:

NICHOLAS P. GODICI

Attesting Officer     Acting Director of the United States Patent and Trademark Office